United States Patent [19]
Georgi

[11] Patent Number: 4,592,365
[45] Date of Patent: * Jun. 3, 1986

[54] ELECTRONIC SPHYGMOMANOMETER

[75] Inventor: Heinz W. Georgi, Del Mar, Calif.

[73] Assignee: Ivac Corporation, San Diego, Calif.

[ * ] Notice: The portion of the term of this patent subsequent to Feb. 2, 1999 has been disclaimed.

[21] Appl. No.: 291,849

[22] Filed: Aug. 10, 1981

[51] Int. Cl.$^4$ ............................................. A61B 5/02
[52] U.S. Cl. .................... 128/680; 128/682; 364/417
[58] Field of Search ............... 128/672, 679, 680, 681, 128/682, 683; 364/417

[56] References Cited

U.S. PATENT DOCUMENTS

| | | | |
|---|---|---|---|
| 3,885,551 | 5/1975 | Massie | 128/682 |
| 3,939,824 | 2/1976 | Arneson et al. | 128/672 |
| 4,058,117 | 11/1977 | Kaspari et al. | 128/682 |
| 4,105,020 | 8/1978 | Matsuoka et al. | 128/682 |
| 4,144,879 | 3/1979 | Nakayama et al. | 128/680 |
| 4,216,779 | 8/1980 | Squires et al. | 128/682 |
| 4,245,648 | 1/1981 | Trimmer et al. | 128/680 |
| 4,313,445 | 2/1982 | Georgi | 128/682 |

Primary Examiner—Kyle L. Howell
Assistant Examiner—Francis J. Jaworski
Attorney, Agent, or Firm—Fulwider, Patton, Rieber, Lee & Utecht

[57] ABSTRACT

An electronic method and apparatus for automatically determining systolic and diastolic blood pressures and heart rate by accurately detecting, verifying and evaluating the full stream of korotkoff sounds produced as electrical signals from a microphone in a cuff occluding the brachial artery of a patient and the corresponding blood pressure pulse signals which accompany and are precursors to genuine korotkoff sound signals. Blood pressure is measured with the aid of a programmed data processor such as a microprocessor. Waveform analysis is first performed upon the incoming signal waveforms to initially separate true pressure pulses and korotkoff sound signals from a variety of artifact and noise signals and to provide digital pulse streams in memory correctly indicating proper pressure pulse and korotkoff sound occurrences in the time and blood pressure domains, with each pressure pulse proportional in amplitude to the amplitude of the corresponding detected precursor input pressure signal represented and each korotkoff pulse proportional to the negative slope amplitude of the corresponding detected korotkoff sound. The output pulse signal streams are then further analyzed by the digital processing subsystem and compared with each other to additionally remove any noise and artifact signals passed as otherwise misleading genuine signals, to modify and certify the resultant data as either reliable or suspect, to determine heart rate and the most probable values of systolic and diastolic blood pressure levels indicated by the pulse signal streams detected during the measurement cycle.

100 Claims, 54 Drawing Figures

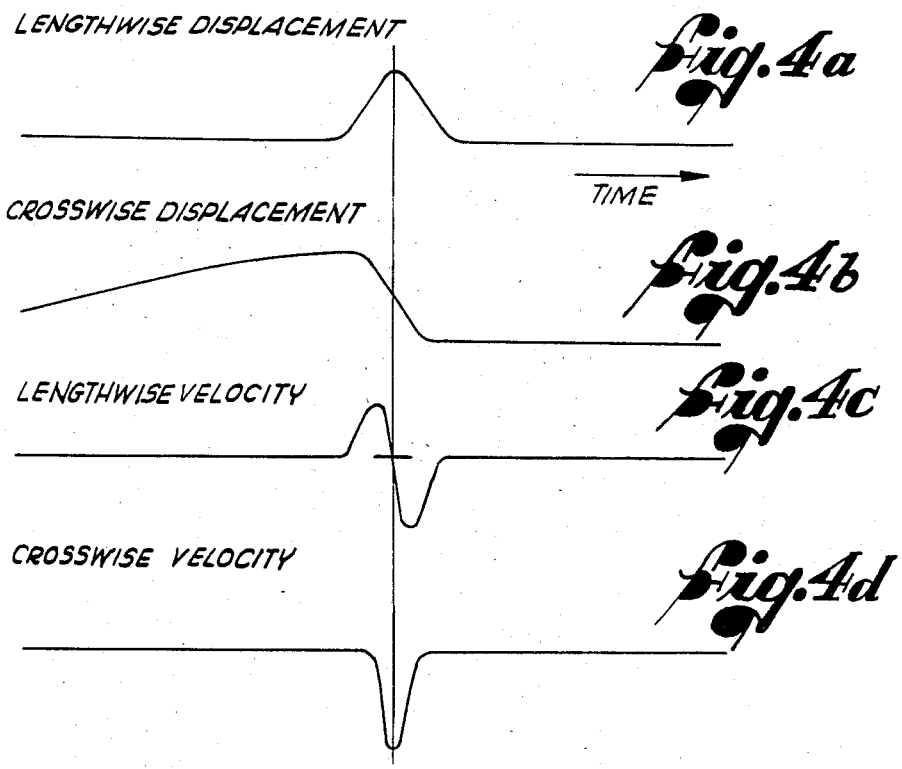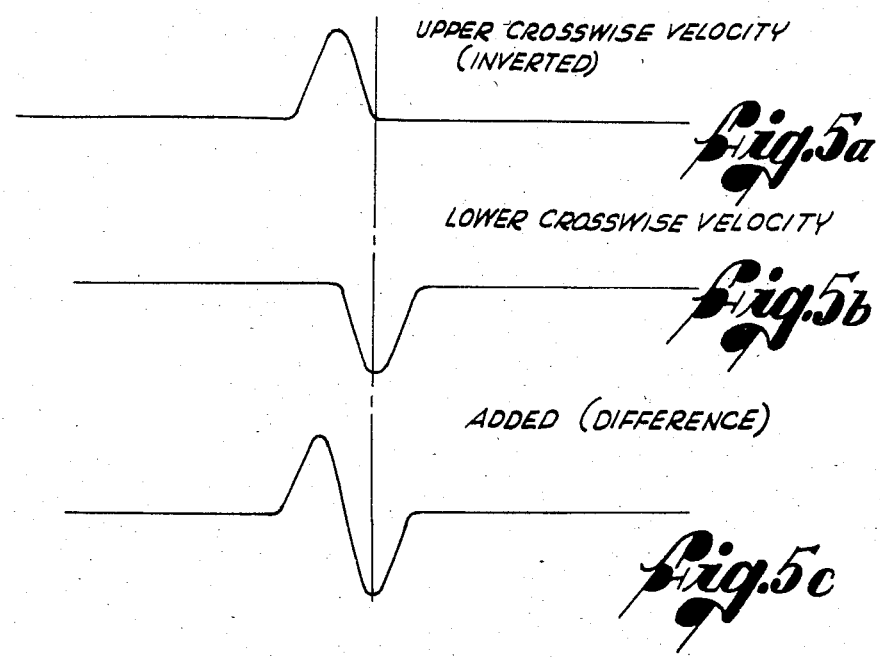

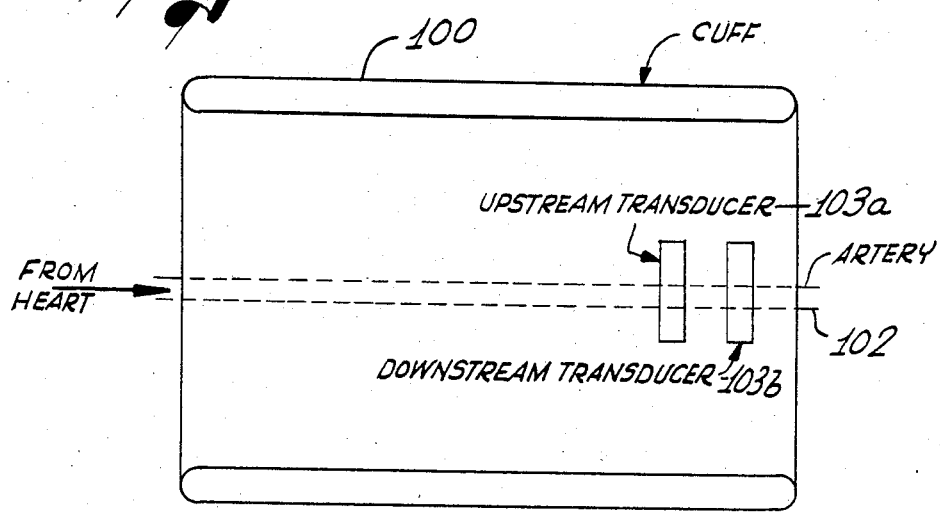
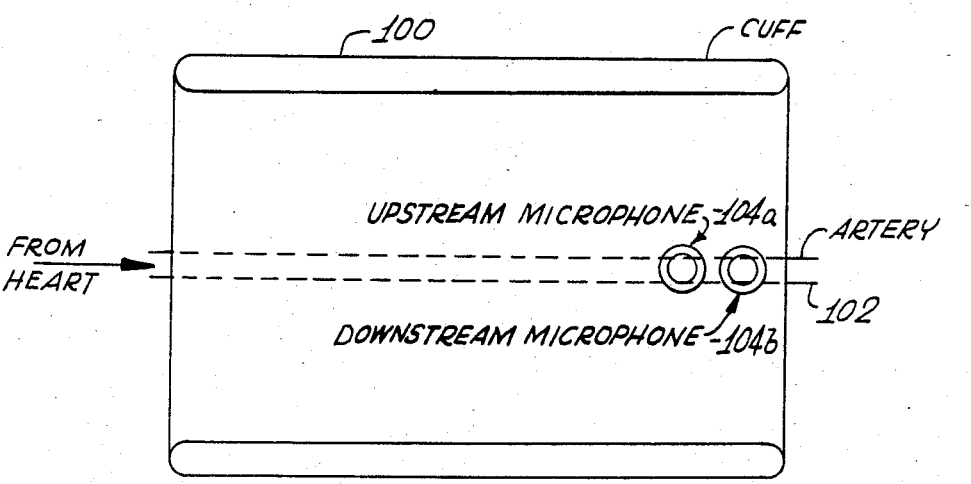

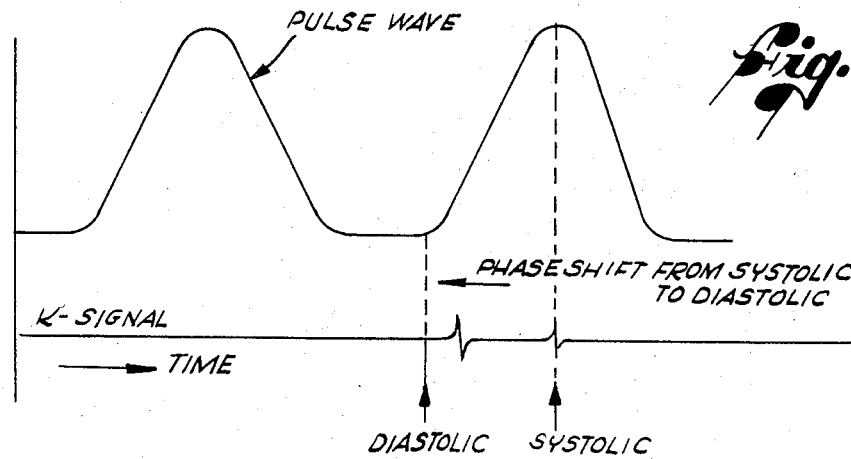
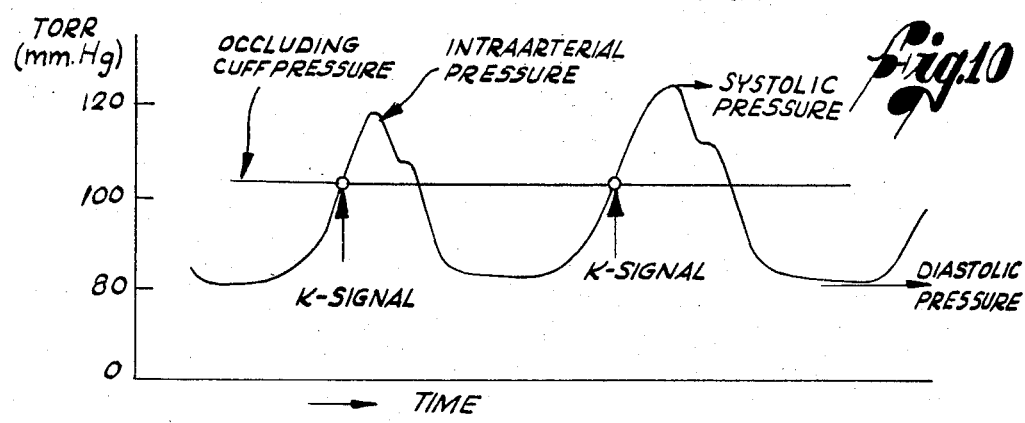
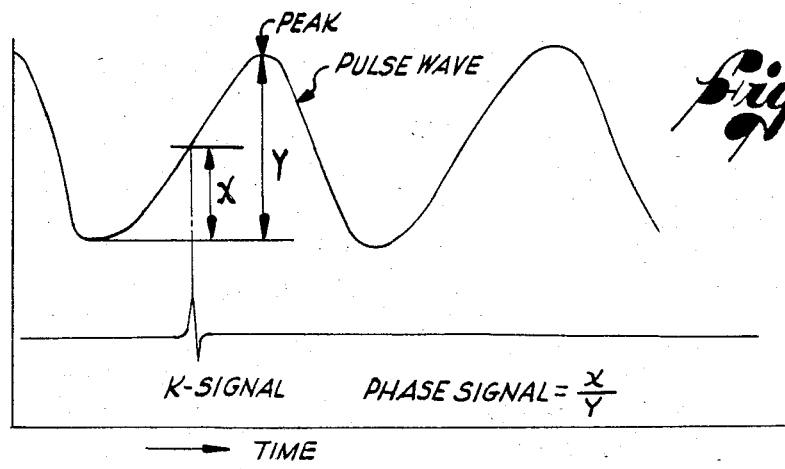

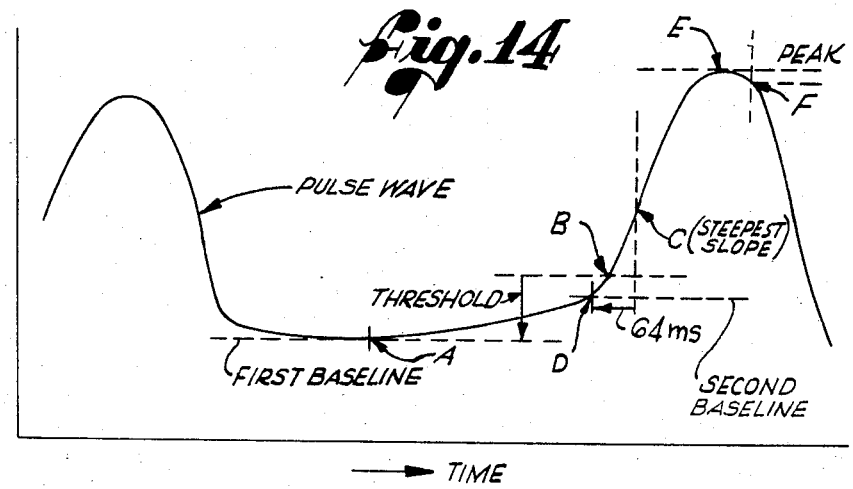
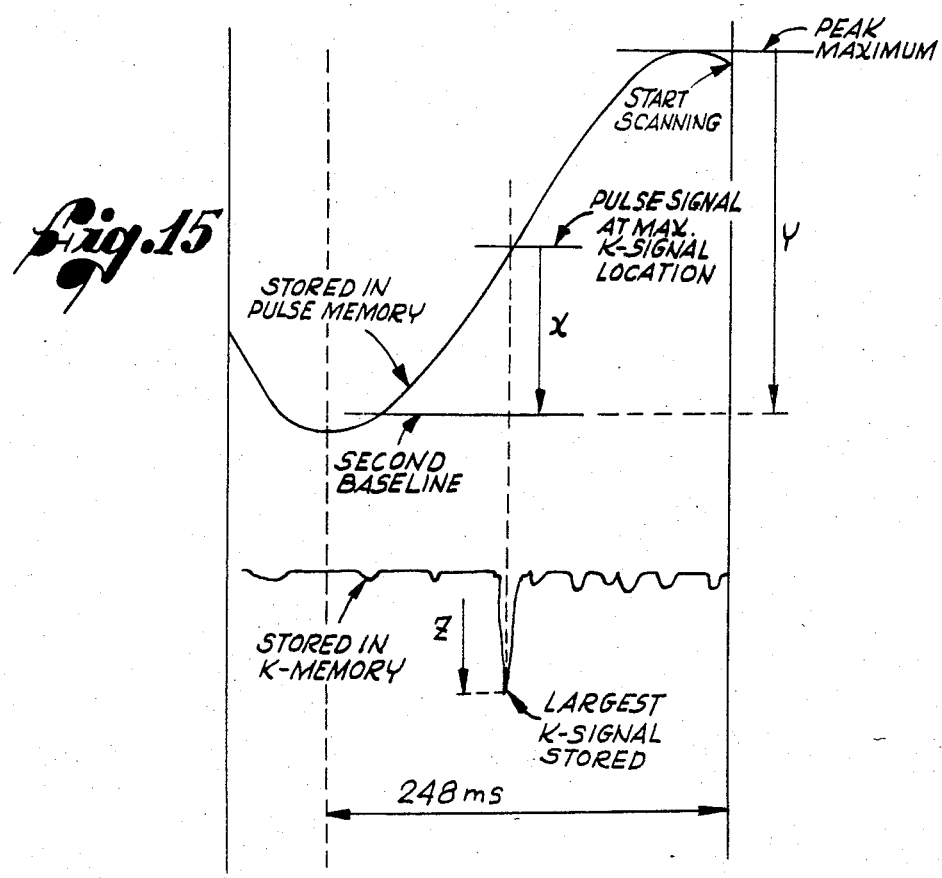

ELECTRONIC SPHYGMOMANOMETER

BACKGROUND OF THE INVENTION

This invention relates generally to improvements in methods and apparatus for the measurement of blood pressure and heart rate and, more particularly, to a new and improved electronic sphygmomanometer system enabling very rapid, accurate, reliable and easily obtained blood pressure and heart rate measurements.

It is common practice in the medical arts, as in hospitals and doctor's offices, to employ an auscultation technique for measuring the blood pressure of a patient by using the characteristics of the so-called korotkoff sounds to determine the systolic and diastolic values of the patient's blood pressure.

The kortkoff method typically makes use of an inflated cuff surrounding a portion of the patient's upper arm. Sufficient inflation of the cuff closes off or completely occludes the brachial artery of the patient. As air is released and the cuff is slowly deflated, a point is reached at which the occluded artery begins to open for a very brief period during each cardiac cycle. At this point, the cuff pressure, which is assumed in using this process as being approximately equal to the blood pressure in the brachial artery, will be that of the peak pressure obtained during the cardiac cycle, this pressure being known in the medical arts as the systolic blood pressure.

Detection of the point at which the artery first opens may be made by any suitable listening device such as a stethoscope or microphone applied to the arm over the artery, usually at the downstream end of the inflated cuff. As the artery opens, auscultatory sounds caused by the pulsating blood flow or tubulence in the blood stream below the occlusion are sensed as a sudden rush of blood by the listening device, and these sounds are referred to in the medical arts as the well known korotkoff sounds. At the point of first detection, where the decreasing cuff pressure is matched by the maximum blood pressure, medical personel skilled in the auscultation technique can detect the sudden blood flow in the artery and the onset of korotkoff sounds, and thereby determine the systolic blood pressure.

As the pressure in the cuff continues to drop, the korotkoff sounds continue substantially in synchronization with the blood pressure pulses produced during successive cardiac cycles. Eventually, however, a point is reached at which the artery remains open during the entire cardiac cycle and, at this point, the korotkoff sounds appear to cease entirely. The cuff pressure at this point approximates the lowest blood pressure reached during the cardiac cycle, with the heart essentially at rest, and this is known as the diastolic blood pressure.

Hence, it will be apparent that, if values of the decreasing cuff pressure are correlated with the korotkoff sound output of the stethoscope or microphone, the cuff pressure at the time the first korotkoff sound occurs is approximately equal to the systolic blood pressure, while the cuff pressure at the time the last korotkoff sound occurs is approximately equal to the diastolic blood pressure encountered during the measurement process.

It will be apparent from the foregoing that conventional blood pressure measurement procedures using an inflatable cuff and a suitable listening device are prone to a number of significant deficiencies. In this regard, medical personnel making such measurements are required to make rather difficult and sometimes highly subjective determinations regarding the presence or absence of korotkoff sounds which may be of relatively low and difficult to detect amplitudes and are often intermixed and easily confused with ambiguous signals generated by artifacts and both internal and external noise. Such artifacts and noise may be due to cardiovascular irregularities and even to the inadvertent bumping of the blood pressure cuff or the movement of the patient while the blood pressure is being measured. Moreover, noise and artifact signals generally appear to be produced more frequently in sick patients than in healthy patients, so that the process is oftentimes more difficult to perform accurately in those instances where the very requirement for a high degree of accuracy is greatest. In addition, the determination of the end points for the onset and cessation of the korotkoff sound pulse train is somewhat uncertain and, therefore, subject to further inaccuracy in the absence of considerable training and much experience on the part of skilled medical personnel.

Accordingly, blood pressure measurements by the conventional sphygmomanometer are subject to a number of human measurement errors such as bias from past medical records, poor hearing, poor operator technique, distractions, improper operator training, missing an auscultatory gap, confusion by artifacts as may be due to bigeminal pulse biqniny, arrhythmias, and other cardiovascular irregularities, misinterpretation of the diastolic pressures, particularly for those cases where the fourth and fifth phases of the korotkoff sounds are indistinct and, as previously noted, misinterpretation of the presence or absence of a heart beat where the heart beats may be weak. The need to eliminate these human measurement errors, as well as the need to increase the speed and decrease the difficulty of blood pressure measurement has resulted in a continuing search for new and improved methods for the automatic non-invasive measurement of blood pressure.

Since there are relatively few persons possessing the requisite high levels of skill and experience to obtain consistently accurate blood pressure measurements using conventional manual auscultation techniques, various attempts have been made in the prior art to eliminate the aforedescribed deficiencies by mechanizing and automating the measurement process, so that the subjective factors introduced when an untrained person attempts to measure blood pressures can be eliminated and, further, to provide some discrimination against artifacts and noise. However, such automatic systems for measuring blood pressure and, typically, associated heart rate, have generally proven to be overly sensitive to spurious signals generated by artifacts and noise and have proven, therefore, to be in many instances less accurate than medical personnel using tried and true manual procedures. As a consequence, automatic korotkoff sound monitoring systems for determining blood pressure by the auscultation method have experienced only limited acceptance by the medical profession.

A number of techniques, other than auscultatory, have also been employed in the prior art to measure blood pressure, such as volumetric methods, Doppler or impedance techniques, and oscillometric techniques wherein the blood pressure waveform is analyzed. In the latter oscillometric method, the fluctuations in cuff pressure are used to measure blood pressure. Through comparison with other methods of blood pressure measurement, it has been determined that a correlation exits between the relative amplitudes of the blood pressure oscillations and the systolic, diastolic and mean pressures. The mean pressures are said to occur at the point where the pressure oscillations are at a maximum, the systolic and diastolic where they are at some percentage, typically about one-half, of the peak amplitude. However, these points can only be considered approximations, at best, and can vary considerably from individual to individual.

Hence, notwithstanding the recognition of the need for methods and apparatus which would be capable of automatically or semi-automatically measuring blood pressure, and the effort which has theretofore been exerted in attempts to fulfill that need, a reliable and effective method, which can be implemented in an instrument of reasonable cost, has not been provided by the prior art.

In recent years, efforts by the inventor of the present invention have provided substantial improvements in automated sphygmomanometer systems and have relied upon the detection of specified korotkoff sound precursors to certify genuine korotkoff sound signals and reject artifacts and noise. Such a blood pressure measuring system is described in co-pending application Ser. No. 845,081, filed Oct. 25, 1977, entitled "Electronic Sphygmomanometer", inventor Heinz W. Georgi, now U.S. Pat. No. 4,313,445, issued Feb. 2, 1982. Efforts by the inventor have continued to further refine and enhance the basic system and techniques set forth in the aforementioned application and to thereby substantially improve the accuracy, reliability and practicality of the blood pressure and related measurements obtainable.

Hence, those concerned with the development and use of automatic sphygmomanometers in the medical field have long recognized the continuing need for further improvements in sphygmomanometer systems which would enable more accurate and reliable blood pressure and heart rate measurements to be made and which would obviate the need for a high degree of skill and subjective expertise on the part of medical personnel making such measurements. The present invention clearly fulfills these needs.

SUMMARY OF THE INVENTION

Briefly, and in general terms, the present invention provides a new and improved sphygmomanometer system embodying novel methods and apparatus for accurately and reliably detecting, analyzing, verifying and evaluating blood pressure pulse and korotkoff sound signal streams, from separate signal sources, and accurately and reliably determining systolic and diastolic blood pressures and heart rate for a patient being monitored during a measurement cycle.

Basically, the present invention is directed to an improved electronic method and apparatus for verifying and certifying the genuineness of korotkoff sound signals and blood pressure pulses with a high degree of reliability, and separating such true korotkoff sound signals and pressure pulses from a variety of artifact and noise signals intermixed with the korotkoff sound signals and blood pressure pulses in the pair of incoming data streams. This is accomplished by performing waveform analysis on all of the individual korotkoff sound signals and the accompanying blood pressure pulse signals associated with each of those korotkoff sound signals. In this regard, it has been discovered by the present Applicant that true korotkoff sound signals produced as incoming data from a transducer always have unique signatures in the form of associated precursor waveforms which can be used to identify true korotkoff sound signals from noise and artifacts and which otherwise have the appearance of false and misleading quasikorotkoff sound signals.

The key waveform characteristics used to certify genuine korotkoff sound signals and to separate such signals from artifacts and noise, are all subject to prescribed analysis and recognition by the system of the present invention. These waveform characteristics include waveform shape, size and direction as measured by polarity, amplitude, slope, phase and timing.

In Applicant's co-pending application, Ser. No. 845,081, filed Oct. 25, 1977, entitled "Electronic Sphygmomanometer", now U.S. Pat. No. 4,313,445, issued Feb. 2, 1982, Applicant describes a basic system for detecting and utilizing specified korotkoff sound precursors to certify genuine korotkoff sound signals and reject artifacts and noise. This earlier system was a predecessor design to the system of the present invention which provides substantial and novel improvements.

In the earlier system of the aforementioned patent, the auscultatory korotkoff sounds are detected by a single microphone having isotropic characteristics which are responsive not only to the sudden rush of blood through the artery indicative of a korotkoff event, but also responsive to arm expansion indicative of the cardiac cycle blood pressure pulse, so that both korotkoff and pressure pulse information are superimposed in each korotkoff sound signal produced as output from the microphone transducer. Hence, in the aforementioned earlier system, electrical signal output from the microphone was first filtered and analyzed in an analog prescreening subsystem providing three analysis channels for processing all incoming signal waveforms. The prescreening subsystem filtered the incoming data and provided as electrical output a pulse train correctly correlating and marking the locations of korotkoff sound signals in the time and blood pressure domains. The analog prescreening subsystem performed waveform analysis upon all the incoming signal waveforms, based upon the discovery of certain unique characteristics associated with those waveforms correctly depicting true korotkoff sound signals, in contrast with those waveforms representing a variety of artifact and noise signals. In this connection, it had been discovered that waveform characteristics of the incoming signals, as opposed to mere frequency characteristics, provided the most reliable means for accurately separating korotkoff sound signals from an electrical signal environment which also included artifact and noise signals falling within the typical frequency domain associated with true korotkoff sound signals.

Since, in the aforementioned patent, the blood pressure and korotkoff sound signals are superimposed, the signals from the signal input data stream were initially separated into a korotkoff sound signal channel and two associated precursor analysis channels. In this regard, the analog prescreening subsystem provided a first spike channel to measure the amplitude of the korotkoff sound signal and produce an output pulse proportional to that amplitude, a so-called diastolic channel which correlated the incoming signal waveform with certain generalized diastolic waveform precursor characteristics to indicate the occurrence of a true korotkoff sound signal, and a systolic analysis channel which correlated all the incoming signal waveforms with a generalized systolic waveform precursor characteristic to likewise certify the occurrence of a true korotkoff sound signal.

The present invention further refines and enhances the basic system and techniques set forth in the aforementioned patent, and substantially improves the accuracy, reliability and practicality of the blood pressure and heart rate measurements obtainable.

In accordance with one aspect of the present invention, the korotkoff sound signals, and associated precursors in the form of blood pressure pulses, are obtained, at the outset from separate signal sources to provide a pair of input data signal streams through separate channels for the pressure wave precursor and the korotkoff sound signals, rather than providing a single signal stream with combined or comingled information as obtained from a single isotropic microphone transducer. Waveform analysis is then performed separately on both the korotkoff sound signals and the pressure pulse waveforms, and subsequently further performed in comparing the korotkoff signals with the precursor waveforms. Korotkoff sound signals are certified as genuine if they possess sufficient magnitudes of slope, occur in proper phase with associated genuine precursor pressure pulses and on the positive slope portion of a precursor waveform.

In order to provide korotkoff sound signals which minimize the superposition of blood pressure pulse information by an isotropic signal microphone transducer, Applicant has also developed, as another aspect of the present invention, a special purpose "longitudinal" bender transducer, or flex sensor, which is positioned in the inflatable cuff with its longitudinal axis parallel to the brachial artery in the arm of the patient being monitored and which provides enhanced response to the wavefront of the traveling wave representing the sudden forward motion of the blood rushing through the brachial artery during each korotkoff event. This new and improved korotkoff sound signal transducer is relatively insensitive to expansion motion of the arm as a whole which occurs during each cardiac cycle.

In addition, Applicant has discovered that a pair of conventional microphone transducers may be substituted for a single longitudinal transducer, if suitably spaced apart along the longitudinal axis of the brachial artery to provide an upstream transducer and a downstream transducer acting in unison.

Sensing of the blood pressure pulse signal from the pressure fluctuations in the cuff, together with obtaining separate korotkoff sound signal information, provides enhanced signal to noise ratios and much better separation of the two signals to be analyzed, namely the korotkoff sound signals and the precursor blood pressure pulse waveforms. In this regard, each signal channel can be optimized for the frequency content of the particular signal to be handled by that particular channel. Sensing of the pulse signal from the pressure in the cuff also provides signals of considerably larger amplitude above the systolic pressure, since the whole arm expands and contracts with the pressure fluctuations. In contrast, a typical microphone, located at the downstream end of the inflatable cuff does not sense much arm expansion above systolic levels, because the cuff holds off all of the blood flow.

As previously indicated, the specialized microphone transducer has been optimized to be most sensitive to the change in artery dimensions caused by the sudden rush of blood flowing at the moment that the artery pressure exceeds the maximum cuff pressure to create a korotkoff event. This has been achieved by making the transducer long and narrow and placing it parallel to the brachial artery. Such an arrangement also tends to minimize the sensitivity of the microphone to blood pressure pulse fluctuations, so that the latter signals must be obtained from a different signal source and fed to a separate channel. The vast improvement in channel separation enhances the sensing of noise levels on the korotkoff sound signal channel. The clean blood pressure pulse signal enables the gating of korotkoff sound signals and noise signals into reliable time segments. Hence, the system of the present invention provides substantially better signal-to-noise ratios, in addition to the use of new precursor characteristics and criteria for certification of genuine korotkoff sound signals, than the system set forth in Applicant's aforementioned patent.

The system of the present invention determines the blood pressure by inflating a cuff on the arm of a patient to a pressure above the systolic level and then deflating at a slow, relatively constant rate to a pressure below the diastolic pressure level. During the deflation cycle, the korotkoff sound signals from a specialized microphone and the precursor blood pressure pulse signals from the cuff are analyzed in real time and subsequently reanalyzed after storage. When the real time analysis indicates that a genuine heart pulse has occurred, the following data is stored in memory for subsequent analysis, after the deflection process has been completed:

1. Time elapsed from last precursor blood pressure pulse (for determination of pulse rate).
2. Maximum amplitude of the precursor pulse waveform.
3. Korotkoff sound signal slope amplitude.
4. Relative phase between the korotkoff sound signal and its associated pressure pulse precursor.
5. Occluding pressure in the cuff.

The real time analysis of the precursor pressure pulse and korotkoff sound signals also provide noise detection criteria which protects against artifact signals caused by arm motion, muscle twitching or the like. If any of these noise criteria are met, the deflation is stopped and no further data is stored. When the noise signal disappears, deflation is resumed after the cuff has first been re-pumped to the pressure where the deflation process was interrupted, if necessary.

The precursor blood pressure pulse waveform is generated as the difference signal between the output of a suitable cuff pressure transducer and the control signal controlling deflation of the cuff. The precursor pulse waveform is analyzed continuously in real time during deflation. The decision to store data in the data memory is based on the result of this analysis which determines when a true heart pulse (contraction, systole) has occurred. When the latter event is detected, the microphone signal spectrum previously stored is examined for the existence of a possible genuine korotkoff sound signal. The pressure pulse precursor waveform is analyzed for slope, polarity and slope magnitude, as well as amplitude, to determine not only the genuineness of the pulse pressure precursor, per se, in contrast to artifacts and noise, but also to locate the peak of the genuine precursor. The korotkoff sound signal memory can then be subsequently scanned to determine whether or not any genuine korotkoff sound signals have occurred in the appropriate "window" period defined by a fixed time period preceding the peak of the pressure pulse on the positive slope region of the precursor. Hence, it is necessary to store in memory all of the signals from the korotkoff sound signal transducer which have occurred for a specified time period before the occurrence of the precursor waveform peak.

The korotkoff sound signal, as received from the specialized longitudinal bender microphone, or equivalent, is differentiated digitally, and only slopes (either positive or negative, depending upon signal polarity) exceeding a minimum amplitude threshold are stored. In addition, the korotkoff sound signal memory and the blood pressure pulse precursor signal memory are scanned to determine the phase of the korotkoff sound signal relative to the pressure pulse signal. The output korotkoff sound signal pulse stream and the blood pressure precursor pulse signal stream is further analyzed by the digital processing system to additionally remove any noise and artifact signals passed as otherwise misleading quasi-korotkoff sound pulses and genuine blood pressure pulses, to modify and certify the resultant data as either reliable or suspect, to determined heart rate and the most probable values for systolic and diastolic blood pressure levels.

The digital processing system, in accordance with the invention, not only performs further analysis upon the korotkoff sound pulse stream and the precursor blood pressure pulse stream, but also performs other new and improved control functions relating to start-up of the system and conditioning of the system to enable the measurement process to proceed. This includes control of the inflation of the cuff upon the arm of the patient, the determination that the inflation has reached a proper level to enable proper data to be obtained, prevention of over-inflation, and initiation and control of deflation, as well as dumping of the remaining pressure in the cuff after sufficient information has been obtained to make all of the required blood pressure and heart rate determinations. The latter dumping of cuff pressure minimizes extended occlusion of the patient's brachial artery beyond the time needed to complete the measurement process.

The pulse rate is computed by taking the average of all pulse periods that occurred when the cuff pressure was between the oscillometric systolic and diastolic approximate pressures, pulse periods occurring outside of these limits being ignored. After the average is computed, all periods that were used to compute the average are compared with that average. If one is found that is less than one half of the average, the number of periods used to compute the average is reduced by one, but the sum is held the same. This prevents short periods caused by an artifact from giving a false additional period. After this correction, the average period is recomputed and stored for subsequent display. If the number of periods found is less than a prescribed number, the computation is abandoned and a "low signal" indication is generated.

Determination of the blood pressure, based upon the korotkoff sound signal amplitudes stored in memory, consists of the following steps:
1. Computing a korotkoff threshold level.
2. Locating the korotkoff sound signal above the threshold level which corresponds to the highest cuff pressure.
3. Extrapolating, in accordance with the invention, to compensate for resolution errors, and determining the systolic pressure.
4. Locating the korotkoff sound signal above the computer threshold which corresponds to the lowest cuff pressure.
5. Extrapolating, in accordance with the invention, to compensate for resolution errors, and thereby determining the diastolic blood pressure.

The new and improved electronic sphygmomanometer system of the present invention is extremely accurate, reliable and easy to use. The system provides enhanced precision in separating true korotkoff sound signals and precursor blood pressure signals from artifact and noise signals and is quick to inform medical personnel of any conditions which indicate the presence of unreliable data. Hence, the system of the present invention minimizes the time consuming and error-prone aspects of manual techniques for measurements of human blood pressure and heart rate, obviates the need for a high degree of skill and subjective expertise on the part of medical personnel required to make such measurements, and provides substantially improved speed, accuracy, reliability and practicality of blood pressure and related measurements obtainable with automated instrumentation.

The above and other objects and advantages of the invention will become apparent from the following more detailed description, when taken in conjunction with the accompanying drawings of illustrative embodiments.

DESCRIPTION OF THE DRAWINGS

FIG. 4a illustrates the waveform for physical displacement with time of the longitudinal flex sensor shown in FIGS. 3a–3c, as the brachial artery passes from the fully occluded state to the fully open state;

FIG. 4b illustrates the physical displacement for a similar transducer which is mounted crosswise of the brachial artery rather than parallel to the artery;

FIG. 4c is a waveform illustrating the velocity sensed by a longitudinal sensor parallel to the brachial artery, obtained by differentiating the waveform of FIG. 4a;

FIG. 4d is a waveform illustrating the velocity sensed by a crosswise transducer, obtained by differentiating the waveform of FIG. 4b;

FIGS. 5a and 5b illustrate crosswise velocity waveforms for a pair of spaced apart crosswise transducers, one located upstream and another located downstream of the brachial artery;

FIG. 5c is a velocity waveform which combines the electrical outputs from the pair of transducers represented by the waveforms in FIGS. 5a and 5b;

FIG. 6 illustrates a pair of spaced apart longitudinal transducers positioned to provide the waveforms of FIGS. 5a–5c;

FIG. 7 is a diagram similar to FIG. 6 and illustrating the use of a pair of spaced apart conventional microphones for use in obtaining the signals of FIGS. 5a–5c;

FIG. 9 illustrates idealized waveforms for the blood pressure pulses occurring during each cardiac cycle, and further illustrates the variable location of the korotkoff sound signal (K-signal), indicative of phase shift between the korotkoff sound signal and the pulse waveform as the occluding pressure moves from systolic to diastolic levels;

FIG. 10 illustrates the waveform for intraarterial pressures occurring in the brachial artery, during each cardiac cycle, superimposed upon the occluding cuff pressure to indicate the location of korotkoff events, and further illustrates the functional basis for the phase shift in the korotkoff signal relative to the pulse waveform detected by a cuff transducer and shown in FIG. 9;

FIG. 11 illustrates an idealized pulse waveform from the cuff and korotkoff sound signal, and further illustrates the manner in which relative amplitudes of the pulse waveform are used to obtain a measure of the relative phase between the pulse waveform and the korotkoff signal;

FIG. 14 is a diagram illustrating a typical pulse waveform and showing various criteria used in the waveform analysis of the pulse waveform;

FIG. 15 illustrates the pulse waveform and korotkoff signal spectrum stored in memory for subsequent scanning and relative phase determinations;

FIG. 41b is a plan view of the transducer shown in FIG. 41a;

FIG. 42b is a plan view of the transducer shown in FIG. 42a;

FIG. 43b is a plan view of the transducer shown in FIG. 43a.

DESCRIPTION OF THE PREFERRED EMBODIMENT

The present invention is directed to an improved electronic method and apparatus for verifying and certifying the genuineness of korotkoff sound signals and precursor blood pressure pulses, both obtained from separate signal sources, with a high degree of reliability, and separating such true korotkoff sound signals and pressure pulses from a variety of artifact and noise signals intermixed with the korotkoff sound signals and blood pressure pulses in the incoming data streams. This is accomplished by performing waveform analysis on all of the individually detected korotkoff sound signals and accompanying blood pressure pulses associated with each of those korotkoff sound signals. In this regard, it has been discovered that true korotkoff sound signals produced as incoming data from a sensing transducer always have unique signatures in the form of associated precursor waveforms, which are very effectively and uniquely utilized, in accordance with the present invention, to identify such true korotkoff sound signals from misleading noise and artifact signals which otherwise have the appearance of quasi-korotkoff sound signals.

The key waveform characteristics used in certify genuine korotkoff sound signals and to separate such signals from artifacts and noise, are all subject to the prescribed analysis and recognition by the system of the present invention. These waveform characteristics include waveform shape, size and direction, as measured by polarity, amplitude, slope, phase and timing.

In accordance with the invention, the korotkoff sound signals, and associated precursors in the form of blood pressure pulses, are obtained initially from separate signal sources to provide a pair of input data signal streams through separate channels for the precursor pressure waveforms and the korotkoff sound signals, rather than providing a single signal stream with combined information as would be obtained from a single isotropic microphone transducer. Waveform analysis is then performed on both the korotkoff sound signals and the pressure pulse waveforms, both individually and as matched pairs between the korotkoff sound signals and their associated precursor waveforms.

Figure 1:
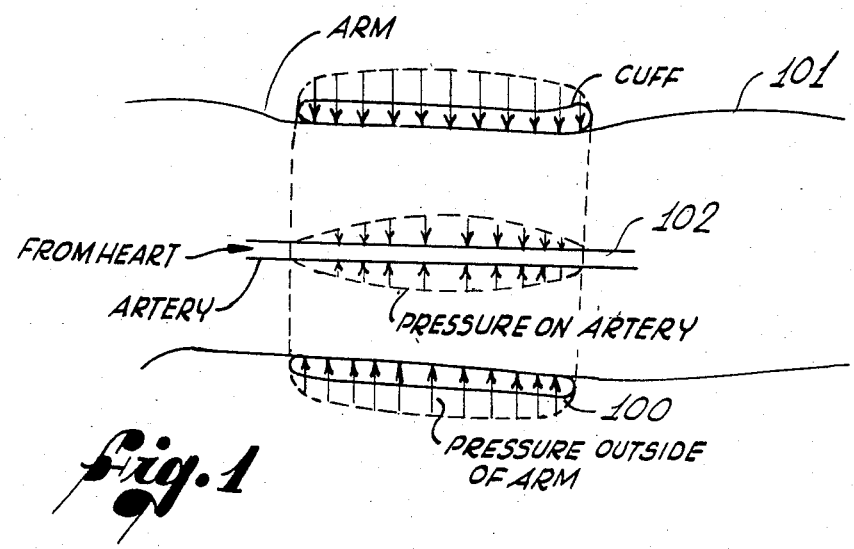
FIG. 1 is a longitudinal, cross-sectional view through the arm of a patient, showing an inflated pressure cuff on the arm applying pressure to the brachial artery inside the arm, and illustrates the pressure distribution over the surface of the arm as well as the internal pressure on the artery.
Figure 2:
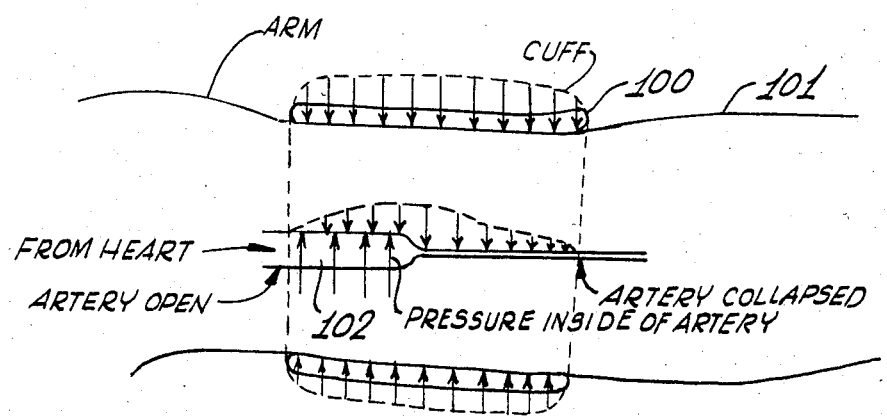
FIG. 2 is a diagram similar to FIG. 1, but showing an occluded artery about to open fully as it overcomes the maximum occluding pressure of the cuff.

Referring now to the drawings, and particularly to FIGS. 1 and 2 thereof, for background regarding the auscultation process utilized in the practice of the present invention, the korotkoff sound detected by a microphone transducer is believed to be generated by the rapid movement of the artery wall when the increasing blood pressure from the contracting heart of the patient overcomes the maximum occluding pressure applied by an inflatable cuff 100 wrapped around the upper arm 101 of the patient. The opening of the previously occluded brachial artery 102 for the korotkoff event is extremely rapid, particularly at the downstream end of the cuff 101, because of the sudden rush of blood flowing into the collapsed portion of the artery.

As best observed in FIG. 1, the occluding pressure on the brachial artery 102 caused by the cuff 101 is non-uniform, even though the pressure applied to the surface of the arm by the cuff is substantially uniform. The occluding pressure on the brachial artery 102 is highest at the center of that portion of the artery located between the edges of the cuff 100 and drops off toward the edges, where it finally goes to substantially zero magnitude. The latter non-uniform pressure distribution upon the brachial artery 102 is caused by the so-called "border" effect occurring as a result of the combination of a finite length of the cuff 100 acting in concert with the flexible tissues in the arm 101.

As best observed in FIG. 2, when the rising upstream blood pressure in the brachial artery 102 exceeds the maximum occluding pressure on the artery at the cuff center, a sudden rush of blood will rapidly occur, because the initial location where the artery finally opens to induce a korotkoff event is at the point of maximum pressure in the center of the cuff 100. Once the maximum occluding pressure has been overcome, the high pressure blood can readily empty downstream, since the occluding pressure progressively diminishes in magnitude in proceeding further downstream and finally drops off to zero at the edge of the cuff. This causes the artery 102 to open very rapidly and generate a traveling wave which can be readily detected as the traditional korotkoff sound by a suitable microphone transducer.

The sudden opening of the brachial artery during the korotkoff event essentially results in a single transient which generates a broad spectrum of frequencies, with a maximum frequency in the region of 50 Hz. to 100 Hz. Typically, microphones used by known available instruments, as well as the common stethoscope, are isotropic or nondirectional in their sensing characteristics. Such microphones tend to be most sensitive to vertical motion or vibration, i.e., perpendicular to the arm 101 and artery 102 in FIG. 2.

Figure 3A:
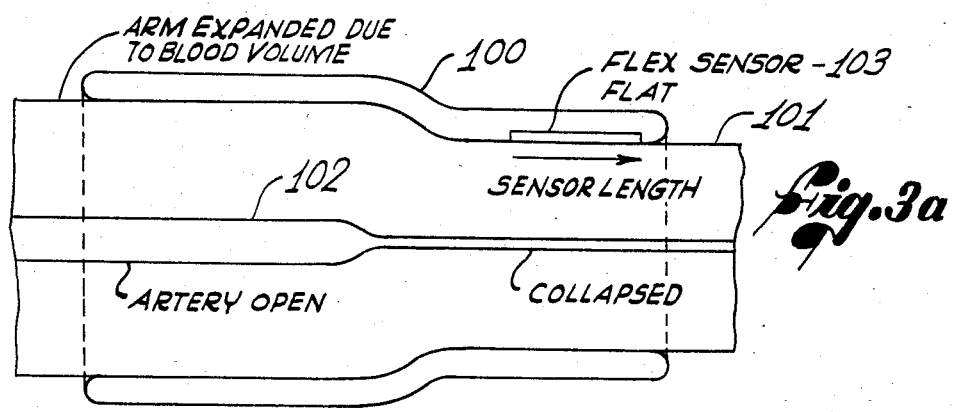
FIG. 3a is a longitudinal, cross-sectional view through the arm of a patient with an inflated blood pressure cuff on the arm, and illustrates the physical state of a korotkoff signal, longitudinal flex sensor, parallel to the brachial artery, at the moment when the blood pressure in the artery first exceeds the maximum occluding pressure applied by the cuff.
Figure 3B:
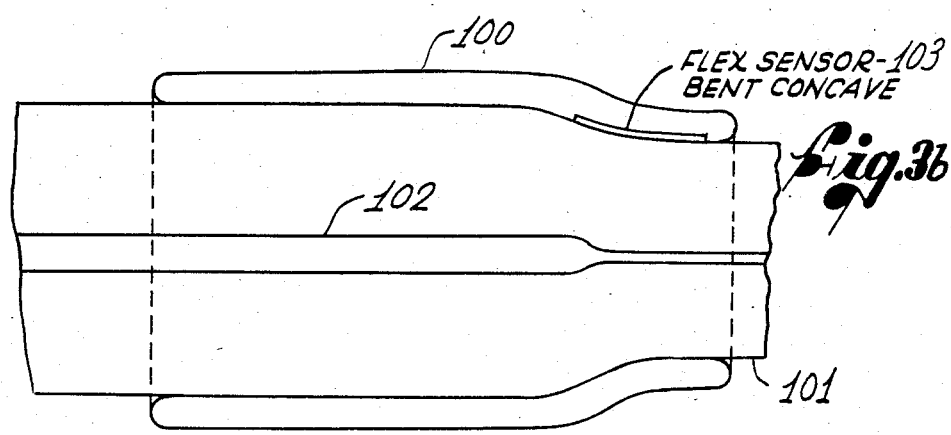
FIG. 3b is a view similar to FIG. 3a, and illustrates the state of the flex sensor as the arm expands in response to the sudden rush of blood through the rapidly opening brachial artery.
Figure 3C:
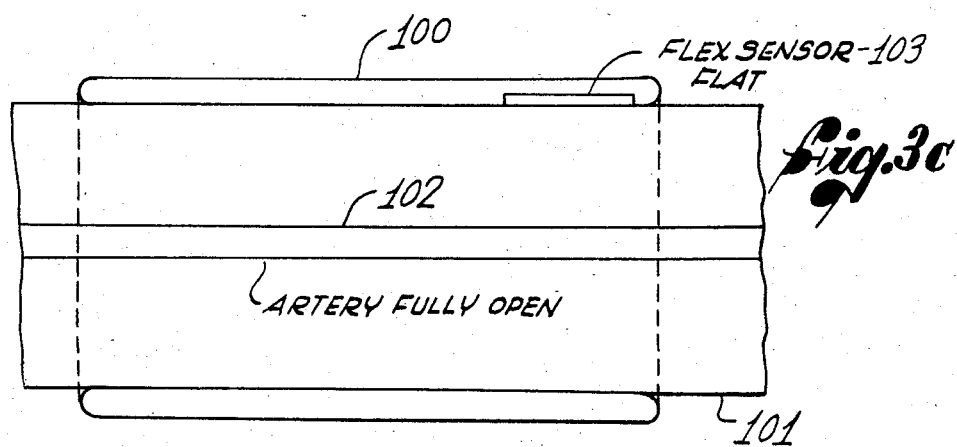
FIG. 3c is a view similar to FIGS. 3a, 3b, and illustrates the physical state of the flex sensor after the artery has fully opened.

Referring now more particularly to FIGS. 3a–3c of the drawings, the use of a longitudinal flex sensor or bender transducer 103, which is located beneath the inflatable cuff 100 at the downstream end of the cuff, and lies with its elongated dimension parallel to the brachial artery 102, very accurately senses the "shockwave" of the blood rushing through the artery under the transducer to depict the occurrence of a korotkoff event. In this regard, and as best observed in FIG. 3a, the flex sensor 103 initially lies flat over the collapsed portion of the brachial artery 102 and, when the blood pressure upstream exceeds the occluding pressure in the cuff, as indicated by the opening artery at the left side of FIG. 3a, the traveling wave caused by the opening artery induces corresponding rapid expansion of the arm 101 just ahead of the traveling wave.

It will be evident in FIG. 3b that the arm expansion induced by the opening brachial artery 102 causes the flex sensor 102 to go from its flat state in FIG. 3a to the concave state shown in FIG. 3b, as the upstream edge of the flex sensor is physically displaced perpendicularly relative to the arm 101 and artery 102.

As best observed in FIG. 3c, once the artery is fully open and the traveling wave has passed, the flex sensor 103 returns to a flat state. Hence, with each korotkoff event, the korotkoff signal generated by the rapidly opening brachial artery 102, causes the flex sensor 103 to go through a physical deflection or deformation cycle which starts out flat, bends concave and then returns to the flat state.

The flex sensor 103, while being very sensitive to the type of arm expansion which reflects the traveling wave induced by rapid opening of the brachial artery 102, and, hence, possesses the requisite high sensitivity suitable for detection of korotkoff sound signals, displays substantial insensitivity to overall arm expansion indicative of the cardiac cycle pulse pressure waveform. The reason for this insensitivity to overall arm expansion is that such overall expansion simultaneously affects all portions of the flex sensor 103 in the same way and, therefore, moves the sensor as a whole, rather than deflecting one portion of the sensor relative to another to induce a bending type distortion productive of a transducer output signal.

The same bender or flex sensor 103, with its longitudinal dimension placed crosswise or perpendicular to the artery 102, as opposed to parallel with the artery, will, in contrast, sense the expansion of the arm 101 due to the increase in overall diameter, such a crosswise configuration being shown in FIG. 6.

Commonly used microphone transducers will usually pick up a combination of both the arm expansion signal and the korotkoff sound signal, but primarily the arm expansion signal.

Referring now more particularly to FIGS. 4a–4d, the signals produced by a longitudinal flex sensor positioned "lengthwise" (parallel to the artery) and "crosswise" (perpendicular to the artery) will be apparent. All transducer systems ultimately make use of some form of differentiation of the signal so that the systems are responsive to the velocity of the motion, rather than the displacement signal.

FIG. 4a illustrates the waveform for physical displacement with time of the longitudinal flex sensor 103 shown in FIGS. 3a, 3b and 3c. The vertical axis in FIG. 4a indicates concave deflection. It will be apparent that, as the brachial artery passes from the fully occluded state to the fully open state, the waveform rises to a maximum and then falls off to zero when the sensor returns to its flat state.

FIG. 4b shows the physical displacement for a similar longitudinal transducer which is mounted crosswise or perpendicular to the brachial artery 102, rather than parallel to the artery, and primarily shows the dominant arm expansion signal, due to the cardiac cycle blood pressure variation, as a slowly rising waveform which then drops off.

FIG. 4c illustrates the velocity sensed by the flex sensor 103 parallel to the brachial artery 102 and is obtained by differentiating the waveform of FIG. 4a. The waveform shown in FIG. 4c is considered to be the idealized waveform for a korotkoff sound signal.

FIG. 4d illustrates the velocity sensed by a crosswise transducer, likewise obtained by differentiating the waveform of FIG. 4b, and shows a single negative peak rather than the quasi-sine wave or double spike signature of the typical korotkoff sound signal illustrated in FIG. 4c.

Artifact signals which are caused by arm motion and muscle flexing appear to affect a crosswise flex sensor much more than a lengthwise positioned flex sensor parallel to the brachial artery. This can be explained by the fact that the flexing of the arm muscles causes more of a diameter change over the whole length of the muscle, as compared with a change over a very short segment which would cause a lengthwise transducer to flex and generate the signals of FIGS. 4a and 4c.

The same result as a single lengthwise placed flex sensor 103 can be achieved by using two crosswise transducers (FIG. 6) separated, for example, by about 1.5 inches. In this regard, FIGS. 5a and 5b illustrate crosswise velocity waveforms for a pair of spaced apart crosswise transducer in an inflatable cuff, one located upstream and the other located downstream of the brachial artery. FIG. 5a shows the upstream crosswise velocity signal, electrically inverted, while FIG. 5c shows the downstream crosswise velocity signal, the two signals being shifted in phase because of the physical spacing between the transducers.

By adding the two transducer velocity signals illustrated in FIGS. 5a and 5b, to produce the combined waveform shown in FIG. 5c, it will be apparent that the two signals produce a a very similar waveform to that obtainable from a single lengthwise positioned flex sensor, as illustrated in FIG. 4c. Hence, the combination of a pair of crosswise transducers can be used to obtain a suitable korotkoff sound signal waveform. This combination of two crosswise transducers is, therefore, also sensitive to the moving wavefront in the brachial artery, and is less sensitive to diameter changes in the muscle because the two arm expansion signals will cancel whenever they coincide in time. Thus, the waveforms of FIG. 5a and FIG. 5b are displaced in time for a korotkoff sound signal produced by a traveling wavefront, but those waveforms are not displaced in time for an overall arm expansion signal which would affect both crosswise transducers simultaneously and thereby eliminate any phase shift in the signal output from the two transducers.

In other words, the use of a pair of spaced apart transducers, as illustrated in FIGS. 6 and 7, enhances the sensitivity to the directional aspects of the signals detected, as in a traveling wavefront, and mitigates the sensitivity to the nondirectional aspects of the detected signals, as characterized by whole arm expansion signals and artifacts, thus enhancing the electrical output signal-to-noise ratio.

FIG. 6 illustrates a pair of crosswise flex sensors spaced apart along the brachial artery 102 and located at the downstream end of the cuff 100, the upstream transducer 103a producing the waveform of FIG. 5a, and the downstream transducer 103b producing the waveform of FIG. 5b for each korotkoff event, the combination producing the waveform of FIG. 5c.

In addition, and as best observed in FIG. 7, it has been determined that a pair of conventional microphone transducers 104a and 104b may be substituted for a single longitudinal flex sensor 103 and used in the same manner as the pair of crosswise transducers 103a, 103b, respectively, shown in FIG. 6, if suitably spaced apart along the longitudinal axis of the brachial artery 102. The microphone 104a is used as an upstream transducer, while the microphone 104b is used as a downstream transducer, acting in unison to provide a korotkoff sound signal such as that illustrated in FIG. 5c.

Essentially, the use of two crosswise transducers or two conventional microphone transducers simulates the longitudinal flex sensor 103 by providing a pair of short rigid portions which are spaced apart by a pivot point.

Utilizing the aforedescribed korotkoff signal transducer configurations, the system of the present invention determines the blood pressure by inflating the cuff 100 on the arm 101 of the patient to a pressure above the systolic level and then deflecting at a slow, relatively constant rate of approximately 5 mm Hg/sec. to a pressure below the diastolic pressure level. During the deflation cycle, the korotkoff sound signals and the blood pressure pulse signals from the cuff are analyzed in real time and subsequently reanalyzed after storage.

As previously indicated, the specialized flex sensor 103 has been optimized to be most sensitive to the change in the dimensions of the brachial artery 102 caused by the sudden rush of blood flowing at the moment that the artery pressure exceeds the maximum cuff pressure to create a korotkoff event. This has been achieved by making the flex sensor or bender transducer long and narrow and locating it in the cuff 100 parallel to the brachial artery 102. Such an arrangement, while it enhances the sensitivity to korotkoff sound signals, also minimizes the sensitivity of the transducer to blood pressure pulse fluctuations, making a separate channel and transducer necessary for obtaining the pulse pressure waveform. However, the vast improvement in channel separation further enhances the sensing of noise levels which appear on the korotkoff sound signal channel. The enhanced "clean" blood pressure pulse waveform enables precise gating of the korotkoff sound signals and noise signals into reliable time segments for appropriate analysis. Hence, the system of the present invention, utilizing separate channels for the korotkoff sound signal and the precursor pulse waveform provides substantially better signal-to-noise ratios, as well as enhanced capability in the utilization of precursor characteristics for certification of genuine korotkoff sound signals.

The real time analysis of the pressure pulse and korotkoff sound signals also provides noise detection criteria which protects against artifact signals caused by arm motion, muscle twitching or the like. If any of these noise criteria are met, the deflation process is stopped and no further data is stored. When the noise signal disappears, deflation is resumed after the cuff 100 has first been repumped to the pressure where the deflation was first interrupted, if that should be necessary.

The precursor pulse waveform is generated as a difference signal between the output of a suitable cuff pressure transducer and the control signal controlling deflation of the cuff 100. The pulse waveform is sensed by picking up the small pressure fluctuations in the bladder of the cuff 100. These pressure pulse waveform fluctuations are caused by the change in the volume of the arm 101 under the cuff 100 due to the pressure fluctuations during each heart cycle.

The amplitude of the blood pressure pulse waveform fluctuations changes considerably, depending upon the pressure in the cuff. If the cuff 100 is inflated above systolic pressure and then slowly deflated, the pulse pressure waveform amplitude rises to the maximum, somewhere between the systolic and diastolic pressure levels (usually closer to the diastolic level) and then drops off again, but never falls to zero.

The explanation for the aforedescribed change in pulse waveform amplitude is as follows: On every systole or heart contraction, the blood pressure rises upstream of the cuff 100. If the pressure in the cuff 100 is above the systolic level, the artery is collapsed almost to the upstream edge of the cuff. However, the rising blood pressure will always cause some blood to flow and open the artery at least a small distance, because the pressure applied to the brachial artery 102 by the cuff is nonuniform and drops to zero at the edges of the cuff, as previously indicated in connection with the discussion of FIGS. 1 and 2. This intrusion of blood into the region below the cuff 100 causes the arm 101 to expand somewhat and, therefore, the pressure in th cuff rises.

As the cuff is slowly deflated, the distance of the intrusion by blood on each cardiac cycle gets larger and larger, causing the pressure pulse fluctuation in the cuff to increase. At some point between the systolic and diastolic pressure levels, the brachial artery 102 will open all the way on every cardiac cycle, and also collapse again almost completely. As the pressure in the cuff diminishes further towards the diastolic level, the collapsing section of the brachial artery gets progressively shorter, causing the volume changes in the cuff to become correspondingly smaller.

Below the diastolic pressure level, the brachial artery 102 will remain open all the time, and the only volume change sensed by the cuff is due to the flexibility of the artery wall which causes small expansions and contractions, but no artery collapse.

Figure 16:
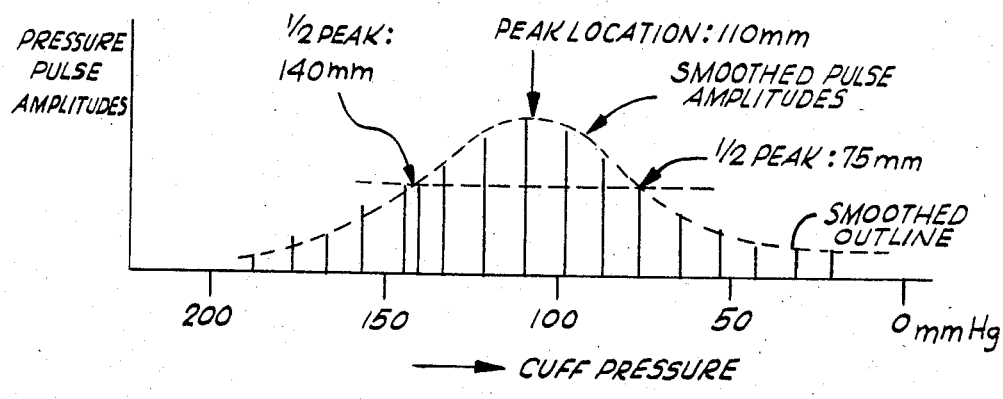
FIG. 16 is a graphical representation illustrating the distribution of pressure pulse amplitudes over the pressure spectrum.

The aforedescribed fluctuations in the cuff pressure are used in the so-called oscillometric method of blood pressure measurement. Through comparison with other methods of blood pressure measurement, it has been found that a correlation exists between the relative amplitudes of the pulse waveform oscillations and the systolic, diastolic and mean pressure levels. The mean pressures are said to occur at the point where the pulse waveform oscillations are at a maximum, the systolic and diastolic levels being where the oscillations are about one-half of the peak amplitude. One example of this type of pulse waveform amplitude spectrum is illustrated in FIG. 16 of the drawings and will be discussed subsequently in connection with the digital analysis of the precursor waveforms. However, in accordance with the present invention, it is recognized that the systolic and diastolic levels located in the oscillometric technique of blood pressure measurement are only approximations and can vary considerably from individual to individual. Hence, the present invention utilizes the pulse pressure waveforms as a precursor for the certification of genuine korotkoff sound signals, and the primary method of blood pressure measurement relies upon the auscultation process using korotkoff sound signals certified as genuine.

Figure 8:
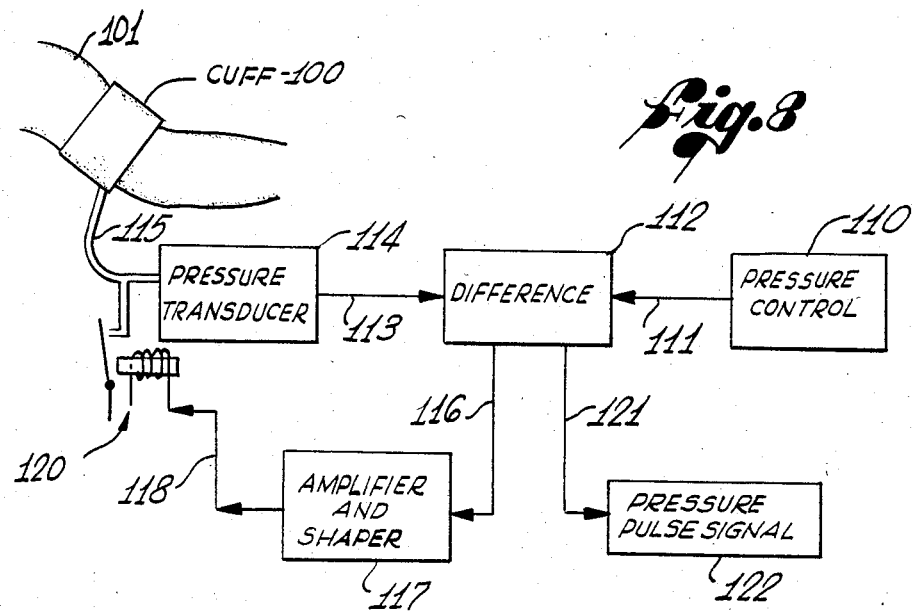
FIG. 8 is a block diagram of the subsystem for deriving the pressure pulse waveform.

Referring now to FIG. 8, the pulse waveform is generated as a difference signal between the output of the pressure transducer and the control signal controlling the deflation of the cuff. Essentially, this is the same as the error signal controlling the opening and closing of a leaker valve in the pumping system, except that the signal for the leaker has some frequency sensitive components in it for stabilizing the control loop.

As best observed in FIG. 8, the pressure in the cuff 100 on the arm 101 of a patient, is controlled by a suitable input signal from a pressure control 110, the signal being in the form of a linear ramp provided over line 111 and representing a pressure drop of approximately 5 mm. Hg./sec. This signal is compared at an error junction 112 with the electrical output over line 113 from a suitable pressure transducer 114 measuring the actual pressure in the cuff 100 transmitted via a fluid conduit 115.

If the electrical output from the pressure transducer is higher than the control signal, indicating that the pressure in the cuff is too high, the signal over line 116 to the amplifier and shaper 117, produces a control output over line 118 to open a leaker valve 120 wider and, therefore, release more air per second from the bladder of the cuff 100.

Fluctuations in the cuff pressure caused by the heart pulse i.e., the precursor pulse waveform, appear at the output of the error junction difference circuit 112, over line 121, to provide the pressure pulse signal 122 which is the desired precursor waveform.

The pressure pulse signal obviously also affects the leaker subsystem 120 in such a way that the latter tries to counteract the fluctuations in the pulse waveform. However, the mechanical time response of the leaker subsystem 120 is too slow to smooth out the pulse waveform to any significant extent.

Essentially, the same pressure pulse waveform signal could be generated by simply A.C. coupling the electrical output of the pressure transducer 114, thereby suppressing the large cuff pressure offset and only amplifying the pulse waveform component. Hence, the pulse waveform is essentially a small ripple signal on a large DC offset which is the pressure in the cuff, and the time constant of the servo loop is such that it tends to compensate for the large DC offset, but will not track the ripple, so that the ripple signal is preserved as the precursor pulse waveform.

In accordance with the invention, it has been discovered that the pair of signals detected, i.e., the korotkoff sound signal and the precursor pulse wave are interrelated with respect to their relative appearance in the time domain.

The pulse waveform is analyzed continuously in real time during deflation. The decision to store data in the data memory is based on the result of this analysis which determines when a true heart pulse in a cardiac cycle has occurred. When the latter event is detected, the flex sensor signal is examined for the existence of a possible genuine korotkoff sound signal. The pressure pulse precursor waveform is analyzed for slope, polarity and slope magnitude, as well as pulse wave precursor, per se, in contrast to artifacts and noise, but also to locate the peak of the genuine precursor so that the korotkoff sound signal memory can be subsequently scanned to determine whether or not any genuine korotkoff sound signals have occurred in the appropriate "window" defined by a fixed time period preceding the peak of the pressure pulse on the positive slope region of the precursor. Hence, it is necessary to store in memory all the signals from the korotkoff sound signal transducer which have occurred for a specified time period before the occurrence of the pressure pulse precursor peak, as well as to store the precursor waveform itself.

The korotkoff sound signal always appears on the rising portion of the pulse wavefrom. FIG. 9 illustrates idealized waveforms for the blood pressure pulse waveform occurring during each cardiac cycle, and also shows the variable location of the korotkoff sound signal (K-signal), indicative of phase shift between the korotkoff sound signal and the pulse waveform as the occluding pressure on the brachial artery diminishes from systolic to diastolic levels.

The pulse wave, as detected in the fluctuating cuff pressure an derived as the output precursor pressure pulse signal 122 in FIG. 8, is directly related to the intra-arterial blood pressure which induces the pulse wave in the cuff, and is a direct result of the intra-arterial waveform. In this regard, FIG. 10 illustrates the waveform for the intra-arterial pressures, occurring in the brachial artery during each cardiac cycle, and shows the waveform superimposed upon the occluding cuff pressure. FIG. 10 indicates the location of the korotkoff events at the crossover points between the two waveforms on the rising portion of the intra-arterial waveform, and further illustrates the functional basis for the phase shift in the korotkoff signal relative to the pulse waveform in the cuff shown in FIG. 9.

Referring to both FIGS. 9 and 10, the pulse pressure in the cuff, represented by the pulse wave in FIG. 9, increases whenever the intra-arterial pressure in FIG. 10 increases, and the pulse wave falls whenever the intra-arterial pressure falls. Hence, the pulse pressure waveform and the intra-arterial pressure waveform are substantially interrelated, but their precise relationship is not predictable, because of the many variables of arm geometry, cuff bladder size, tightness of the cuff, patient tissue tone, and the like. However, all korotkoff sounds do appear in the time period of rising pressure in the cuff.

In addition to the foregoing, there is a definite phase shift which takes place between the pulse wave in FIG. 9 and the korotkoff sound signal as the cuff pressure is reduced by slow deflation. At the systolic pressure level, the korotkoff sound signal appears later on the rising pressure waveform, near or at the peak of the waveform. As the pressure is decreased, the korotkoff sound signal appears earlier and earlier until, at the diastolic level, it appears near the bottom of the rising waveform in FIG. 9.

The reason for the phase shift between the pulse wave in FIG. 9 and the korotkoff sound signal is best explained by reference to FIG. 10. As previously indicated, the korotkoff sound signal appears when the intra-arterial pressure exceeds the occluding pressure on the brachial artery during the rising portion of the intra-arterial pressure waveform. If the occluding pressure is high, toward the systolic pressure level, which would be nearer the peak of the intra-arterial pressure waveform, the korotkoff sound signal would appear closer to the peak of both the intra-arterial pressure waveform in FIG. 10 and the pulse waveform in FIG. 9. As the occluding pressure in the cuff diminishes, the korotkoff sound signal appears earlier and earlier on both waveforms. In other words, the phase shift of the korotkoff sound signal is to the left in FIG. 10 as the occluding pressure diminishes, moving gradually towards the waveform valley represented by the diastolic pressure.

In accordance with the invention, the aforedescribed phase relationship between the korotkoff sound signal and the precursor pulse waveform is used for artifact rejection. There are several ways to obtain a measure of this phase relationship. The preferred method of measuring the phase between the korotkoff sound signal and the pulse wave is to measure the amplitude of the pulse wave at the point where the korotkoff sound signal occurs and determine the ratio of that amplitude to the peak amplitude of the precursor pulse wave. This phase measurement method provides a dimensionless number between zero and one, independent of slope and pulse amplitude. In this regard, FIG. 11 illustrates an idealized pulse waveform from the cuff and korotkoff sound signal and shows the preferred manner in which the relative amplitudes X and Y are used to obtain a measure of the relative phase between the pulse waveform and the korotkoff signal to provide a dimensionless phase signal in the form of the ratio X/Y for use in subsequent korotkoff signal analysis.

Figure 12:
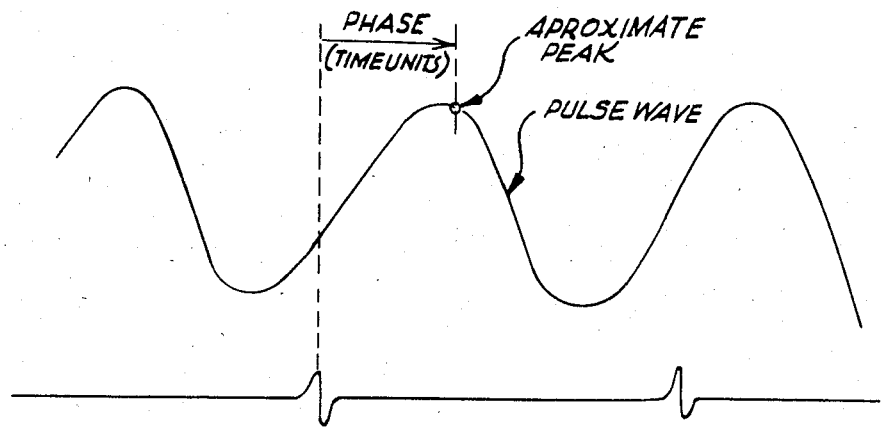
FIGS. 12 and 13 are waveform diagrams similar to FIG. 11, illustrating alternate methods for measuring the phase of the korotkoff signal relative to the pulse waveform.
Figure 13:
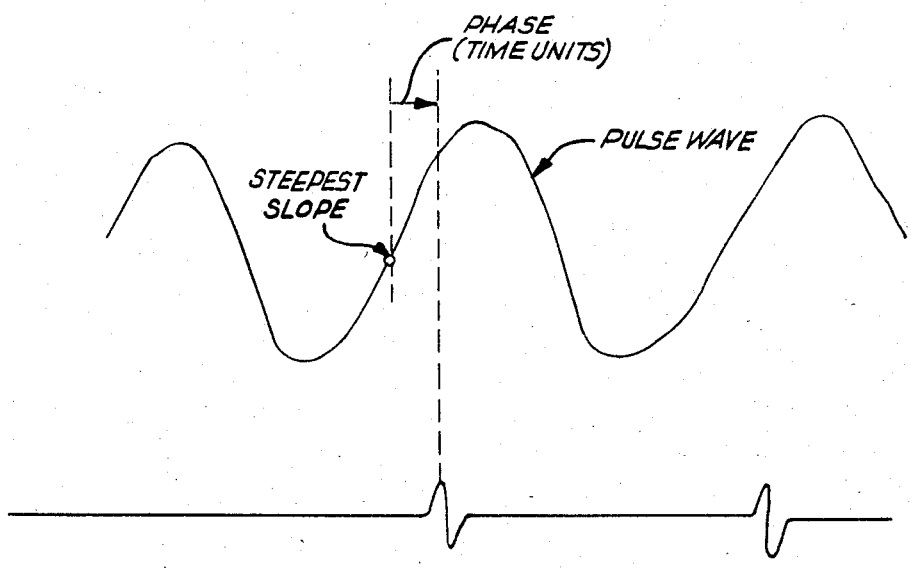

FIGS. 12 and 13 are waveform diagrams, similar to FIG. 11, and illustrate alternate methods for measuring the phase of the korotkoff signal relative to the pulse waveform. FIG. 12 illustrates a method of relative phase measurement by measuring the absolute time on the rising pressure waveform from the occurrence of the korotkoff sound signal to the peak of the pulse wave. FIG. 13 illustrates relative phase measurement in terms of the absolute time from the point of the steepest slope of the pulse wave to the occurrence of the korotkoff sound signal. However, as previously indicated, the ratio phase measurement technique illustrated in FIG. 11 is preferred.

The system of the present invention, in determining blood pressure and heart rate, records all of the korotkoff sound signals and precursor pulse waves received from the korotkoff signal flex sensor 103 (FIGS. 3a–3c) and the pressure pulse signal output 122 (FIG. 8). During the deflation cycle, all of these signals are analyzed in real time and subsequently reanalyzed after storage. When the real time analysis indicates that a genuine heart pulse has occurred, the following data are stored in memory for later analysis after the deflation process has been completed:

1. Time elapsed from last blood pressure pulse (for determination of pulse rate).
2. Maximum precursor pressure pulse amplitude.
3. Korotkoff sound signal slope amplitude.
4. Relative phase between the korotkoff sound signal and its associated pressure pulse precursor.
5. Occluding pressure in the cuff.

The real time analysis of the precursor pressure pulses and the korotkoff sound signals also provide noise detection criteria which protects against artifact signals caused by arm motions, muscle twitching or the like. If any of these noise criteria are met, the deflation process is temporarily aborted and no further data is stored. When the noise signal disappears, the deflation process is resumed.

An additional function of the real time signal analysis is the determination of the time in the measurement cycle where enough data has been collected to provide reliable blood pressure and heart rate determinations. This allows the termination of the deflation process before the pressure in the cuff has gone all the way to zero, i.e., as soon as pressure has dropped a sufficient amount below the diastolic pressure level.

The precursor pulse wave is analyzed continuously in real time during the deflation portion of the measurement cycle. The decision to store data in the data memory is based upon the result of this pulse wave analysis. The latter analysis determines when a true heart pulse or systole has occurred and, when this happens, the differentiated output from the flex sensor 103 in the cuff 100 (FIGS. 3a–3c) is examined in memory for the occurrence of a possible genuine korotkoff signal.

FIG. 14 illustrates a typical precursor pulse wave and illustrates the various criteria used in the waveform analysis of the precursor pulse waveform. In this regard, the pulse wave signal in FIG. 14 is first differentiated and the polarity of the waveform slope is determined. Whenever the slope of the precursor waveform turns positive from a previous negative or zero slope, the absolute value of the slope is held in memory for a determination of the valley bottom, as indicated by point A in FIG. 14, to establish a first baseline amplitude reference level.

When the pulse wave signal goes positive, the difference in amplitude between the updated present value and the first baseline value (A) is continuously tested against an amplitude threshold value. If this amplitude threshold is exceeded, the pulse wave will be considered a real heart beat, unless the slope of the waveform subsequently becomes too steep. The amplitude threshold is indicated as the level at point B on the pulse wave in FIG. 14.

The steepness of the slope of the pulse waveform is also monitored and, if the amplitude of the differentiated wave exceeds a maximum threshold, a pulse wave is then considered an artifact and no data is stored. The steepest slope detected establishes the location of point C in FIG. 14.

The slope amplitude of the pulse wave in FIG. 14 is continuously compared with the previous values during the monitoring process, and the latest value of slope amplitude is only stored if it is larger than all of the previous values, to establish a new location for point C. Whenever a larger value of slope is found, indicating a steeper rise of the waveform, a waveform amplitude that has occurred a prescribed period of time before the maximum slope is then stored as a new second baseline value, indicated as point D in FIG. 14.

A time period of 64 ms. has been empirically determined in the practice of the invention as a suitable time period preceding point C for location of the second baseline at point D. The latter process is a form of bottom clipping for standardization which prevents a slow positive rise or pedestal in the precursor waveform signal, that oftentimes occurs and can be several hundred milliseconds in duration before the actual heartbeat occurs, from producing an erroneous pulse amplitude. Hence, the standardization procedure minimizes the scattering of amplitudes in the data field.

The amplitude of the precursor pulse wave in FIG. 14 is also continuously updated to the highest value detected, to locate the peak amplitude of the pulse wave at point E. If the pulse wave signal drops a very small, prescribed amount in amplitude below the maximum at point E, to point F (which is only a few milliseconds away in the time domain) it is determined that the pulse wave peak has actually occurred and data will be stored. The purpose of confirmination of the peak at point E by a subsequent detection at point F is to avoid false peak detections which might occur if there were jiggles in the precursor waveform.

From FIGS. 9, 11 and 14, it becomes obvious that, by the time the decision to store data has been made at point F in FIG. 14, the korotkoff sound signal has already occurred. Hence, it is necessary to store in memory all of the signals from the flex sensor that have occurred for a given time period prior to the verification of a genuine precursor pulse waveform at point F. This storage time period has beem empirically determined, in accordance with the invention, to be approximately 250 ms. The phase determination between the korotkoff sound signal and the precursor pulse waveform, illustrated in FIG. 11, also mandates the storage of the pulse wave signals for the same time period.

FIG. 15 of the drawings illustrates the pulse waveforms stored in the pulse memory and the korotkoff signal spectrums stored in the K-memory for subsequent scanning and relative phase determination. In this regard, the korotkoff signal, as received from the flex sensor 103 (FIGS. 3a–3c) is first differentiated digitally by computing the difference between the present value and the value that occurred a short time previously, such as 8 ms. This differentiating computation is typically performed every 2 ms., and these difference values, representing korotkoff signal slope, are stored in memory for 248 ms. Only negative slope values of the korotkoff sound signals, exceeding a minimum amplitude threshold, are stored.

Figure 17A:
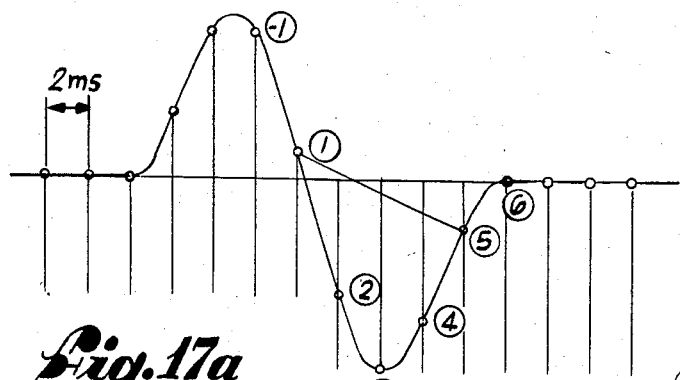
FIG. 17a depicts an idealized korotkoff sound signal waveform and illustrates the manner in which the waveform is scanned for digital analysis.
Figure 17B:
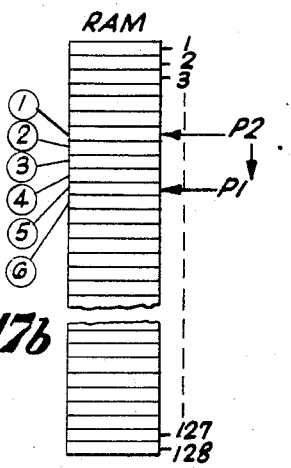
FIG. 17b schematically illustrates the data storage register for recording the location and amplitude of detected korotkoff sound signals and digitally differentiating and storing the values of such signals.

Referring now more particularly to FIGS. 17a and 17b, there is shown in FIG. 17a an idealized korotkoff sound signal waveform, as received from the flex sensor 103, and illustrating the manner in which the waveform is scanned every 2 ms. for digital analysis to determine maximum negative slopes. It will be appreciated that, while negative slope is used in the preferred embodiment of the invention, reversal of polarity may result in the use of positive slope for korotkoff signal analysis. In any event, the choice of negative slope monitoring was determined by the portion of the korotkoff signal waveforms providing the best signal-to-noise ratio.

FIG. 17a shows the idealized korotkoff signal waveform divided into a plurality of 2 ms. time slots for the periodic sampling of waveform amplitude, the points −1, 1, 2, 3, 4, 5 and 6 indicating seven successive amplitude samplings. In this regard, the 2 ms. resolution on the korotkoff sound signal waveform is much greater than that shown in FIG. 17a, which should be considered as exemplary for explanation purposes only.

FIG. 17b schematically illustrates the data storage register or RAM for recording the location and amplitude of the detected korotkoff sound signals and digitally differentiating and storing the values of those signals. In this regard, the RAM is illustrated, by way of example, as a vertical stack of 128 memory slots. The digital processor with which the RAM is associated, contains a pointer P1 which is another register somewhere in memory and scans the RAM stack.

As the korotkoff sound signal in FIG. 17a is sampled, the values of amplitude are stored in the memory locations corresponding to the position of the pointer P1 in FIG. 17b. A second pointer P2 lags 8 ms. or four memory locations behind the pointer P1 in the RAM.

The system operates by subtracting the amplitude stored at the location of pointer P1 from the amplitude 8 ms. earlier at the location of the pointer P2, and storing the difference value, which is a measure of average slope over the 8 ms. time period between the two pointers, in the memory slot adjacent the pointer P2. This is illustrated in FIG. 17a by the line drawn between point 1 and point 5 on the korotkoff signal waveform. Hence, only the four memory slots between P1 and P2, namely points 5, 4, 3 and 2 in FIG. 17a will contain amplitude information in the RAM, while all of the other 124 memory slots will contain slope data which is continuously updated as the pointers P1 and P2 repetitively scan the memory stack in the RAM. Thus, slope data is included in the RAM for 124 locations at 2 ms. per location, yielding a total scan period prior to the peak of the pulse pressure waveform of 248 ms. of the korotkoff sound signal spectrum, as previously shown in FIG. 15.

When the decision to store data has been made, at point F in FIG. 14, a heart beat is certified as having occurred, and the korotkoff signal memory of 248 ms. is scanned to find the largest negative slope amplitude, and its location, among the korotkoff signal spectrum during the scan period. This slope amplitude, indicated as the value Z in FIG. 15, is read out and stored. In addition, the amplitude of the precursor pulse wave at the same point in the time domain is also read out from the pulse wave signal storage to provide the value X in FIGS. 11 and 15. Value X is determined by taking the difference between the precursor pulse wave amplitude at the point where the largest korotkoff sound signal slope is encountered and the previously determined second baseline value at point D in FIG. 14. The value Y in FIGS. 11 and 15, representing the maximum amplitude of the precursor pulse waveform, is determined by taking the difference between the maximum pulse wave amplitude at point E in FIG. 14 and the second baseline value at point D.

At the conclusion of the precursor pulse waveform and korotkoff sound signal scanning process, the following data is stored for subsequent analysis after the deflation process has been completed:

1. The time period from last storage command.
2. Pulse wave amplitude (value Y, FIGS. 11, 15).
3. Maximum korotkoff signal negative slope amplitude (value Z, FIG. 15).
4. Phase signal (ratio X/Y).
5. Pressure in the cuff 100 at point F in FIG. 14.

In addition to the real time measurements for determining the occurrence of genuine precursor pulse waveforms and korotkoff sound signals, additional tests are performed, in accordance with the invention, to monitor both pulse wave and korotkoff sound signal channels for the occurrence of artifacts.

Figure 18:
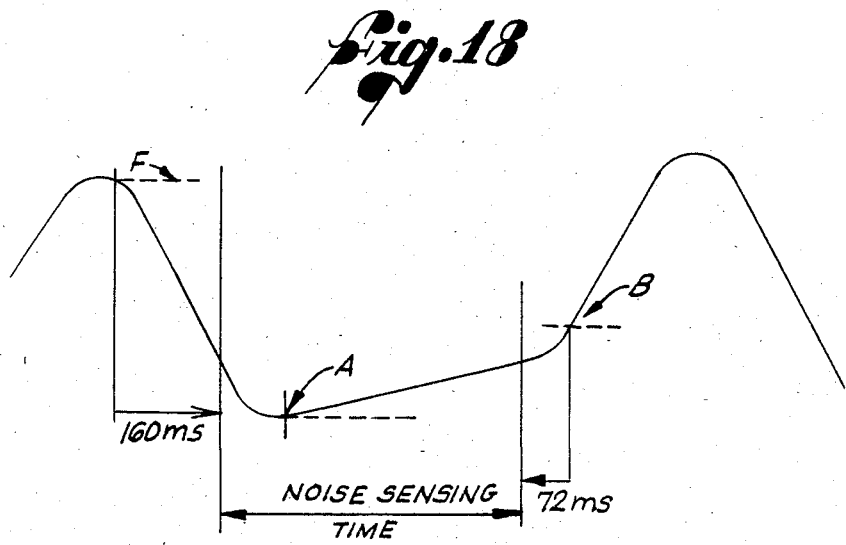
FIG. 18 illustrates a pulse pressure waveform and further defines the period for noise sensing.

Referring now more particularly to FIG. 18, there is shown a pulse pressure waveform including the peak certifying point F, the first baseline A and the amplitude threshold B from FIG. 14. In addition, a pair of guard times, one period 72 ms. prior to the threshold B and a second period 160 ms. after the point F on the previous pulse wave, define a noise sensing time period for determination of a noise threshold, without interference from genuine korotkoff sound signals which might alter the threshold. The fact that the korotkoff sound signals can occur only during the positive slope portions of the precursor pulse waveform thus allows the monitoring of the korotkoff signal channel for noise caused by artifacts, such as arm movement or muscle twitches, during the time between precursor pulse waves. This time separation allows a clear separation of the noise signals from the korotkoff sound signals, making feasible a noise threshold essentially independent of the amplitude of the korotkoff sound signals.

During the time that the pulse waveform has a negative slope, or the amplitude threshold B has not been exceeded, all korotkoff signal channel signals (differentiated and negative) are averaged with a time constant of approximately 1 second, so that very short spikes and high peaks get averaged and have a minimal effect upon the overall noise threshold. The guard time of 160 ms. after the last previous pulse wave peak and 72 ms. before the first amplitude threshold level of the next pulse waveform is utilized to prevent ringing of the korotkoff sound signal or very early korotkoff sound signals at diastolic pressure levels from interfering with the threshold determination.

During the offtime of the noise detector, the 1 second time constant does not operate to reduce the threshold level, so that the noise threshold is simply held constant.

If the computed noise threshold level exceeds a maximum amplitude threshold for noise, the digital system issues a command to stop further deflation of the cuff and temporarily freezes the data collection, until such time as the noise threshold drops to a satisfactory level so that deflation can be resumed, or the measurement cycle is aborted.

In addition to the korotkoff sound signal noise routine, the precursor pulse waveform is also monitored for artifacts and noise. In this regard, both positive and negative slope thresholds are applied to the pulse wave to detect sudden changes in cuff pressure due to motion or muscle twitches or the like. In addition, positive and negative amplitude thresholds on the precursor waveform signal are also applied for detection of large pressure offsets between actual and desired cuff pressure. If any of these thresholds for the precursor pulse waveform are exceeded, cuff deflation is aborted until the noise drops to acceptable levels.

The digital processing system, in accordance with the invention, not only performs further analysis upon the korotkoff sound pulse stream and the precursor blood pressure pulse stream, but also performs other new and improved control functions relating to start-up of the system and conditioning of the system to enable the measurement process to proceed. This includes control of the inflation of the cuff upon the arm of the patient, the determination that the inflation has reached a proper level to enable proper data to be obtained, prevention of over-inflation, and initiation and control of deflation, as well as dumping of the remaining pressure in the cuff after sufficient information has been obtained to make all of the required blood pressure and heart rate determinations. The latter dumping of cuff pressure minimizes extended occlusion of the patient's brachial artery beyond the time needed to complete the measurement process.

The measuring of blood pressure, in accordance with the present invention, is accomplished during a measurement cycle which consists of three basic segments:

(1) The pump-up phase,
(2) The deflation and data collection phase, and
(3) The data analysis and computation of blood pressure and pulse rate phase.

To begin the pump-up phase, an external "start" signal, or an internally generated automatic time base, initializes the system for a measurement cycle. The automatic pump is started and the pressure in the inflatable cuff is monitored until it reaches a preselected value which is typically set by a front panel switch (not shown) for 150, 200, 250 and 300 mm hg. When the preselected value of maximum pressure is reached, the automatic pump is then stopped. The cuff pressure is then monitored for about 3 seconds for possible leaks in the cuff or cuff tubing. If the pressure drops below a minimum prescribed level, the pump is again energized and the leakage test is repeated. If the system fails the leakage test the second time, the measurement is abandoned and an "artifact" signal is generated to inform the user of the situation. If the leakage test is passed, the system is initialized for the deflation phase of the operation during the measurement cycle.

The deflation control is divided into several sequential phases which determine the decisions that have to be made.

During the first 3.5 seconds of deflation, the system tests for the occurrence of korotkoff sound signals. If no korotkoff sound signals are detected, the deflation control switches to the data collection phase. If the system detects a korotkoff sound signal, the 3.5 second time period is reset to zero and a new test period is started. If more than two korotkoff sound signals are detected, the deflation is stopped and the pump is started again to pump to a pressure level 50 mm. Hg. higher than the selected starting pressure. If the system attempts to pump to a higher pressure a second time, the measurement cycle is abandoned and an "artifact" condition is indicated to the user. This prevents a measurement from proceeding if the starting pressure level in the cuff is not above the systolic blood pressure level.

In the data collection phase, the actual data collection and storage begins. At the same time, the pressure in the cuff is monitored. The digital control system remains in this phase until the cuff pressure drops below one-half of the starting cuff pressure for the measurement cycle.

When the pressure in the cuff has diminished to a level below one-half of the cuff starting pressure, the system searches for termination of the deflation segment, while it continues to analyze the precursor pulse waveforms and the korotkoff sound signals. While in this phase, the system first counts the number of korotkoff signals stored. If the number of signals stored is less than five, deflation continues until the pressure has been reduced to one-fourth of the cuff starting pressure. If, at this latter pressure level, less than five korotkoff sound signals have been detected, the measurement cycle is terminated and a "low signal" condition is indicated to the user. If, on the other hand, the number of korotkoff sound signals detected is five or more before deflation to the level of one-fourth of the cuff starting pressure, the system then tests the amplitudes of the precursor pulse waveforms. A weighted average of pulse pressure amplitudes is computed for the purpose of amplitude testing. This weighted average consists of an amplitude that is computed from the last three pulse waves, the present pulse wave and the two previous pulse waves. The weighting is accomplished by taking the average of the present pulse wave with a weight of unity and the previous two pulse waves with a weight of one-half for each pulse wave. If the current average is above one-half of the maximum average found previously, a three-second timer is started. If, in three seconds, another precursor pressure pulse signal is detected, the system continues to deflate. However, if no pressure pulse is detected, the deflation phase is terminated, the remaining cuff pressure is dumped, and the computation segment of this phase is initiated.

If the weighted pressure pulse amplitude is below one-half of the maximum average previously found, the three-second timer is also started. Under these circumstances, if a korotkoff sound signal is detected within three seconds, the system continues to deflate. However, if no korotkoff sound signal is detected, the deflation process is terminated, the cuff pressure is dumped, and the computation segment initiated.

The deflation segment can be interrupted at any time during a measurement cycle by the detection of an artifact. Such artifact detection immediately stops the deflation process, and the system waits for the artifact or noise signal to disappear. If the artifact or noise signal does not disappear within a time limit of ten seconds, the measurement cycle is abandoned and the "artifact" condition is indicated. On the other hand, if the artifact or noise signal disappears before the ten-second time period has elapsed, the cuff pressure is tested. If the cuff pressure is sufficient, the deflation process is simply resumed. If the cuff pressure is not sufficient, the pump is re-energized, and the cuff is inflated to the pressure where the deflation interruption first occurred. At that point, the deflation process is resumed.

In the data analysis and computation phase of the measurement cycle, the data collected and stored in the memory is analyzed and the systolic and diastolic blood pressure levels, as well as the average pulse rate during the measurement cycle is computed and displayed or otherwise suitably indicated to the user. As previously described, data is stored in the memory based upon the precursor waveform analysis. Every time the latter analysis results in the detection of what appears to be a genuine heart beat, a set of five numbers representing various parameters is stored in memory. These numbers are stored in groups so that corresponding numbers can always be identified. The five numbers stored for each heart beat are:

(1) Time elapsed from last heart beat.
(2) Pressure pulse waveform amplitude.
(3) Korotkoff signal slope amplitude.
(4) Phase between pulse waveform and korotkoff sound signal.
(5) Pressure in cuff.

If a heart beat has occurred and no korotkoff sound signal is detected in accordance with the previously described criteria, zeros are stored for the korotkoff sound signal and phase, but elapsed time, pulse waveform amplitude and cuff pressure, i.e., items 1, 2, and 5, are still stored in memory.

The next step in the digital analysis performed by the present invention relates to the elimination of spurious korotkoff sound signals. The first analysis to be performed is the examination of the korotkoff sound signals for artifacts and noise. The analysis begins with the korotkoff sound signal corresponding to the highest cuff pressure. If the corresponding phase signal of the korotkoff sound signal, i.e., the ratio X/Y (FIG. 15) is less than a prescribed minimum threshold value, the korotkoff signal is rejected and eliminated from memory. If the phase signal exceeds the prescribed minimum threshold, the korotkoff sound signal corresponding to the the next lower cuff pressure is examined. If the magnitude of the phase signal corresponding to the latter korotkoff signal is not above the minimum threshold, the search continues to examine successive korotkoff sound signals corresponding to lower and lower cuff pressures.

If a korotkoff sound signal is found with a phase signal of acceptable magnitude, the pressure difference between the latter korotkoff signal and the first korotkoff sound signal is examined. If the pressure difference is less than 15 mm. Hg., both korotkoff sound signals are accepted and the analysis for spurious korotkoff signals on the systolic or high pressure end of the data is terminated. However, if the pressure difference is more than 15 mm. Hg., the first discovered korotkoff signal at the higher cuff pressure is eliminated and the search continues until a pair of korotkoff sound signals is located which have acceptable phase signal values and are less than 15 mm. Hg. apart in cuff pressure in the korotkoff signal spectrum.

The same type of analysis is performed at the low pressure end of the data spectrum, starting with the korotkoff sound signal that has the lowest corresponding cuff pressure and moving upward. For this analysis, the phase signal must be below a prescribed maximum threshold to be acceptable. In all other respects, the analysis for spurious korotkoff signals at the low pressure end of the data spectrum is symmetrical with the analysis performed at the high pressure end of the spectrum.

The next computation examines all of the pulse wave amplitudes stored in memory and determines the center region of the pulse wave amplitudes. As previously described, the pulse wave amplitudes start out at a relatively low value and increase to a peak between systolic and diastolic blood pressure levels, subsequently declining again as the pressure from the cuff is slowly deflated from above systolic to below diastolic pressure.

The purpose of the pulse wave amplitude analysis is to locate the conventional three oscillometric method points on the cuff pressure scale. These points are the point of peak pulse wave amplitude and a pair of points on either side of the peak amplitude, one above and one below the peak, where the pulse wave amplitudes are one-half of the peak value. This is accomplished by "modeling" an outline of pressure pulse wave amplitudes vs. cuff pressure, connecting the amplitudes with straight lines and applying a smoothing routine to generate a substantially smooth pulse wave amplitude curve, as shown in FIG. 16. The location of the peak of a smooth curve and the pair of one-half peak amplitudes are then readily determined. These three points are stored in memory for subsequent further analysis in connection with pulse rate computation and, if desired, can be displayed to correspond to the so-called oscillometric mean, systolic and diastolic blood pressure, in accordance with the conventional oscillometric method of estimated blood pressure measurement.

In accordance with the invention, the heart rate is computed by taking the average of all of the pulse wave periods, representing the time elapsed between pulse wave peaks, that occurred when the cuff pressure was between the oscillometric systolic and diastolic pressures, i.e., the one-half peak amplitude values on opposite sides of the oscillometric mean. Any pulse periods that occur outside of these limits are ignored.

After the pulse period average has been computed, all periods that were used to compute the average are compared with that average. If a period is found which is less than one-half of the computed average, the number of periods used to compute the average is reduced by one, but the sum of all the periods between the limits is held the same. The latter procedure prevents short periods caused by artifacts and noise from providing a false additional period. After this correction, the average period is recomputed and stored for later display. If the number of pulse periods found is less than four in number, the pulse rate computation process is abandoned and a "low signal" condition is appropriately indicated.

The determination of blood pressure in accordance with the invention, is based upon the korotkoff signal amplitudes stored in memory. Initially, a threshold level for the korotkoff sound signals is computed. This threshold is computed from averaged korotkoff signal amplitudes. In a first step, all of the korotkoff signal amplitudes are averaged. Then a second average is taken of all of the korotkoff signal amplitudes equal to or greater than the first computed average. The latter final average is then divided by 6 (empirically determined for use in the preferred embodiment) and stored as the computed threshold for the korotkoff signal spectrum.

Figure 19:
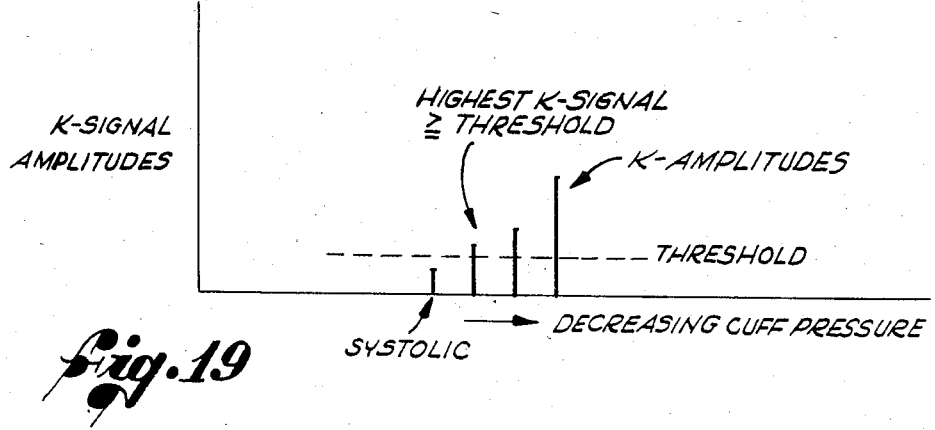
FIG. 19 is a graphical representation of a series of korotkoff signal amplitudes relative to a computed threshold level as utilized in the determination of systolic blood pressure.

In determining the systolic blood pressure, all korotkoff signal amplitudes are first compared with the computed threshold, and the korotkoff signal above the threshold associated with the highest cuff pressure is identified, as shown in FIG. 19.

The extrapolation process for systolic pressure determination consists of several steps. The first step is to inspect the next korotkoff signal associated with a higher cuff pressure. If such a korotkoff signal exists (which would be below the computed threshold) and the period between the two adjacent korotkoff signals is between 0.5 and 1.5 times the average period of the precursor pulse pressure waveform (as opposed to the korotkoff signal spectrum), then this next higher cuff pressure is determined to be the systolic blood pressure; see FIG. 19.

If no korotkoff sound at a higher cuff pressure is located, or the period is outside the limits, a second computational step is performed. First, the average pressure drop per average precursor pulse period is computed. Since the deflation rate is known to be 5 mm. Hg. per second, the pressure drop between successive pulse pressure waveforms can be readily computed. As best observed in FIG. 20, a straight line is then computed through the peaks of the first two korotkoff signal amplitudes. At the location where the straight line intersects the abscissa of the cuff pressures, a new pressure value is defined. If this latter pressure is closer to the first korotkoff signal above the computed threshold associated with the highest cuff pressure than the average pressure drop per pulse period, it is designated as the systolic blood pressure.

Figure 21:
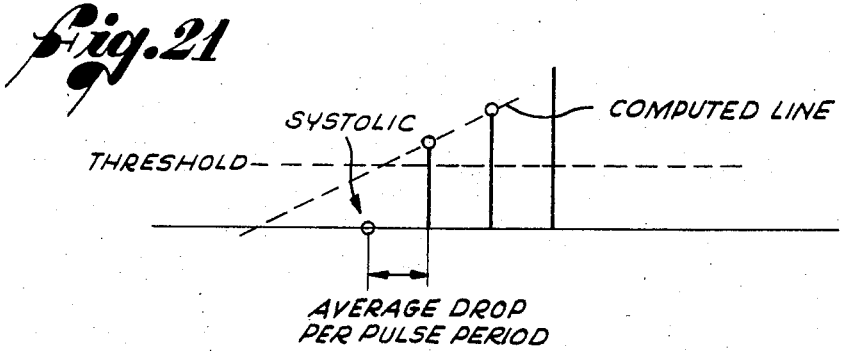
FIG. 21 is a graphical representation, similar to FIG. 20, and illustrates another aspect of the extrapolation technique used in the determination of systolic blood pressure.

If, on the other hand, as shown in FIG. 21, the intersection with the cuff pressure axis is further away from the first korotkoff sound signal above threshold associated with the highest cuff pressure than the average pressure drop per pulse period, then the average pressure drop is added to the latter cuff pressure associated with the first korotkoff signal above threshold to determine the systolic blood pressure.

The extrapolation process for determination of the diastolic blood pressure is similar to that described for the determination of the systolic blood pressure, except that extrapolation is to find a lower pressure rather than to find a higher pressure. In addition, the procedure for locating the first korotkoff sound signal above the threshold to be used as a starting point for the extrapolation process, is different than in the systolic determination. In this regard, starting at the cuff pressure associated with the peak of the pulse pressure waveform (FIG. 16) and scanning downward in cuff pressure, each korotkoff sound signal is examined in sequence to locate the first korotkoff sound signal above the computed threshold and which also satisfies the requirement that it is below the phase signal threshold previously applied in connection with the spurious korotkoff sound elimination process.

If no such korotkoff sound signal which meets both of these criteria is located, the process is abandoned and a "low signal" indicated.

If the desired korotkoff sound signal is located, scanning downward along the cuff pressure axis continues, to locate the first korotkoff sound signal that is below the computed slope amplitude threshold, or zero in value (using the occurrence of precursor pulse waves as markers for where a korotkoff sound signal can occur, including a korotkoff signal at zero amplitude). When the latter korotkoff signal location has been determined, the next korotkoff sound signal in the direction of increasing cuff pressure, which is the last korotkoff signal above the computed threshold, is used as the marker for initiation of the extrapolation process to determine diastolic blood pressure in the same manner previously described for the determination of systolic blood pressure.

The aforedescribed extrapolation routines reduce the time resolution error caused by a relatively fast deflation rate.

Figure 22:
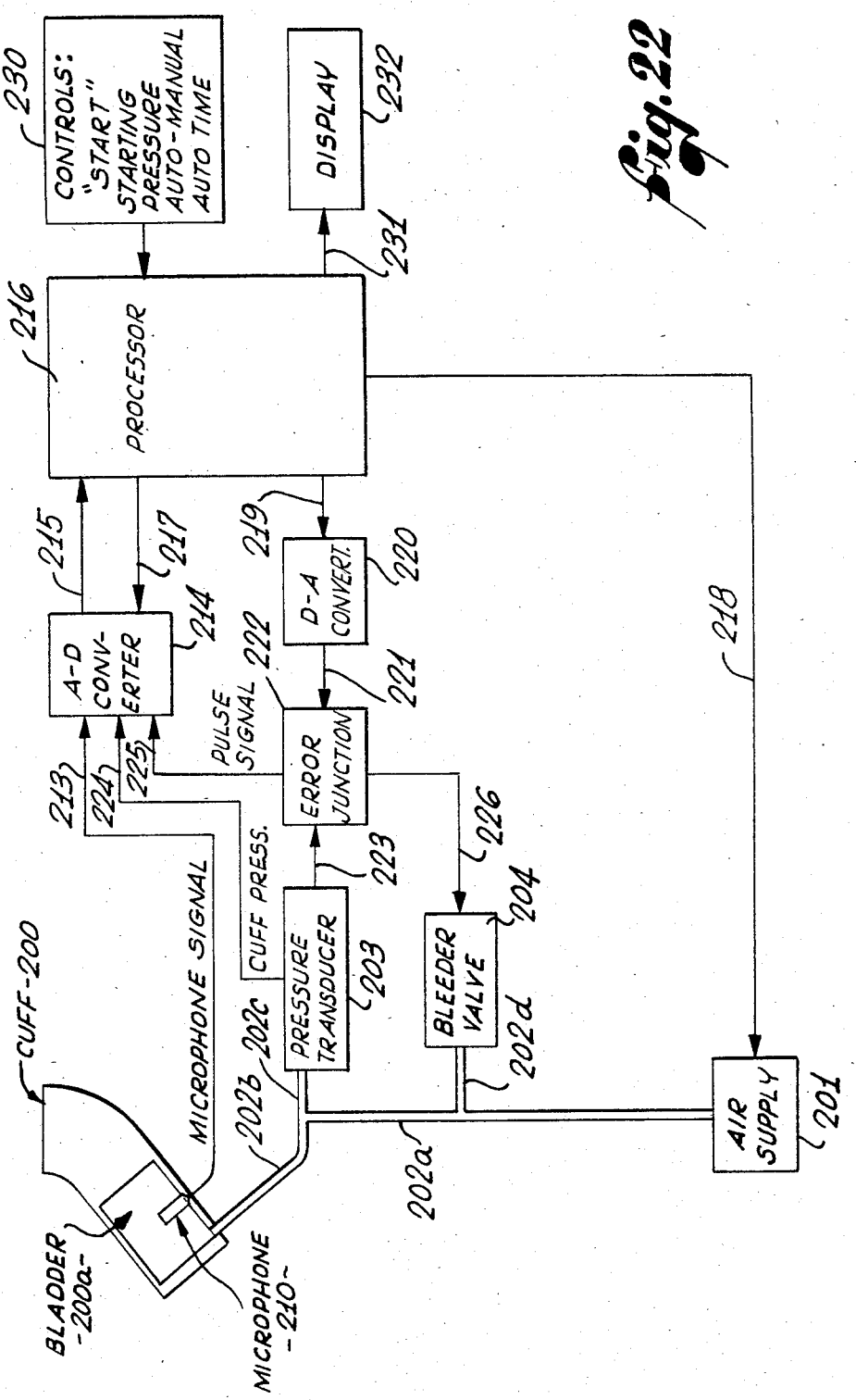
FIG. 22 is an overall block diagram of a generalized sphygmomanometer system incorporating features of the present invention.

Referring now more particularly to FIG. 22 of the drawings, there is shown an overall block diagram of a generalized sphygmomanometer system for the practice of the present invention. The system of FIG. 22 incorporates the usual sphygmomanometer inflatable cuff 200 which is inflated by filling a flexible bladder 200a with air from an automatic air supply 201, through fluid conduits 202a and 202b. The pressure in the cuff 200 and, hence, the pressure in the brachial artery of the patient upon whose arm the cuff 200 is installed, is sensed by a suitable pressure transducer 203 through fluid conduits 202b and 202c. A bleeder valve 204 is used to bleed air from the bladder 200a in the cuff 200 via fluid conduits 202a, 202b, and 202d during the deflation process in the practice of the auscultation technique to detect korotkoff sounds.

A microphone 210 (either in the configuration of FIGS. 3a–3c, FIG. 6 or FIG. 7) overlying the cuff 200 at the downstream end of the cuff, is adapted to detect korotkoff sounds and direct corresponding electrical output signals over line 213 to an analog to digital converter subsystem 214. The digital output of the analog to digital converter subsystem 214 is directed over line 215 as input to a digital processing subsystem 216, typically a digital processor, which performs further analysis upon the signals to enhance the separation of true korotkoff sound signals and pressure pulse precursors from artifacts and noise. The processor 216 also sends signals over line 217 back to the analog to digital converter subsystem 214 to control the operation of the converter subsystem, including its timing functions. In addition, the processor 216 performs a plurality of data manipulations and tests upon the remaining data in the determination of heart rate, and the systolic and diastolic blood pressure levels.

Control over inflation of the bladder 200a in the cuff 200 is effected by the processor subsystem 216 over line 218, which imposes control over the automatic air supply 201 so that the latter can be selectively turned on or off. In addition, the processor subsystem 216 controls the bleeder valve 204, in the manner previously described in connection with the description of FIG. 8, by electrical input over line 219 to a digital to analog converter 220 which, in turn, directs analog input over line 221 to a error junction 222 which also receives input over line 223 from the pressure transducer 203.

The processor subsystem 216 receives the necessary information to effect such control over the air supply 201 and the bleeder valve 204 by receiving electrical information from the pressure transducer 203 over line 224, and from the error junction 222 over line 225, to the analog to digital converter subsystem 214 and then, via line 215, to the processor. The result of this control is the generation of a linear pressure ramp in the cuff 200.

The digital to analog converter 220 sends the signal from the processor 216 to the error junction 222 representative of the desired pressure in the cuff 220 and, if the cuff pressure is higher than the desired pressure, the error junction output over line 226 to the bleeder valve 204 causes the bleeder valve to release air and bring the cuff pressure into line with the ramp signal.

The electrical output from the error junction 222, over line 225, is the precursor pressure pulse signal (corresponding to the pressure pulse signal 122 in FIG. 8).

The digital processor 216, in accordance with the invention, not only performs further analysis upon the korotkoff sound signal and pressure pulse precursors received from the analog to digital converter subsystem 214, but also performs other control functions relating to the start-up of the overall system and conditioning of the system to enable the measurement process to proceed. These conditioning and control operations include control of inflation of the cuff 200 upon the arm of the patient, determination that the inflation has reached the proper level to enable other data to be obtained, as by insuring inflation to a sufficiently high level that the starting pressure is above the pressure at which korotkoff sound signals first appear, prevention of over-inflation, initiation and control of deflation, as well as dumping of the remaining pressure in the cuff after sufficient information has been obtained to make all of the required blood pressure and heart rate determinations. This dumping of cuff pressur minimizes extended occlusion of the patient's brachial artery beyond the time needed to complete the measurement process, particularly where the patient is being continuously monitored and the measurement may be repeated on a frequent basis.

The processor 216 also includes a plurality of external controls 230 such as a "start" push button, controls for establishing the desired starting pressure, an automatic timer and the selection of automatic and manual modes. The processor 216 can also provide information over line 231 to an optional display 232. The controls 230 and display 232 may be of conventional design.

Figure 23:
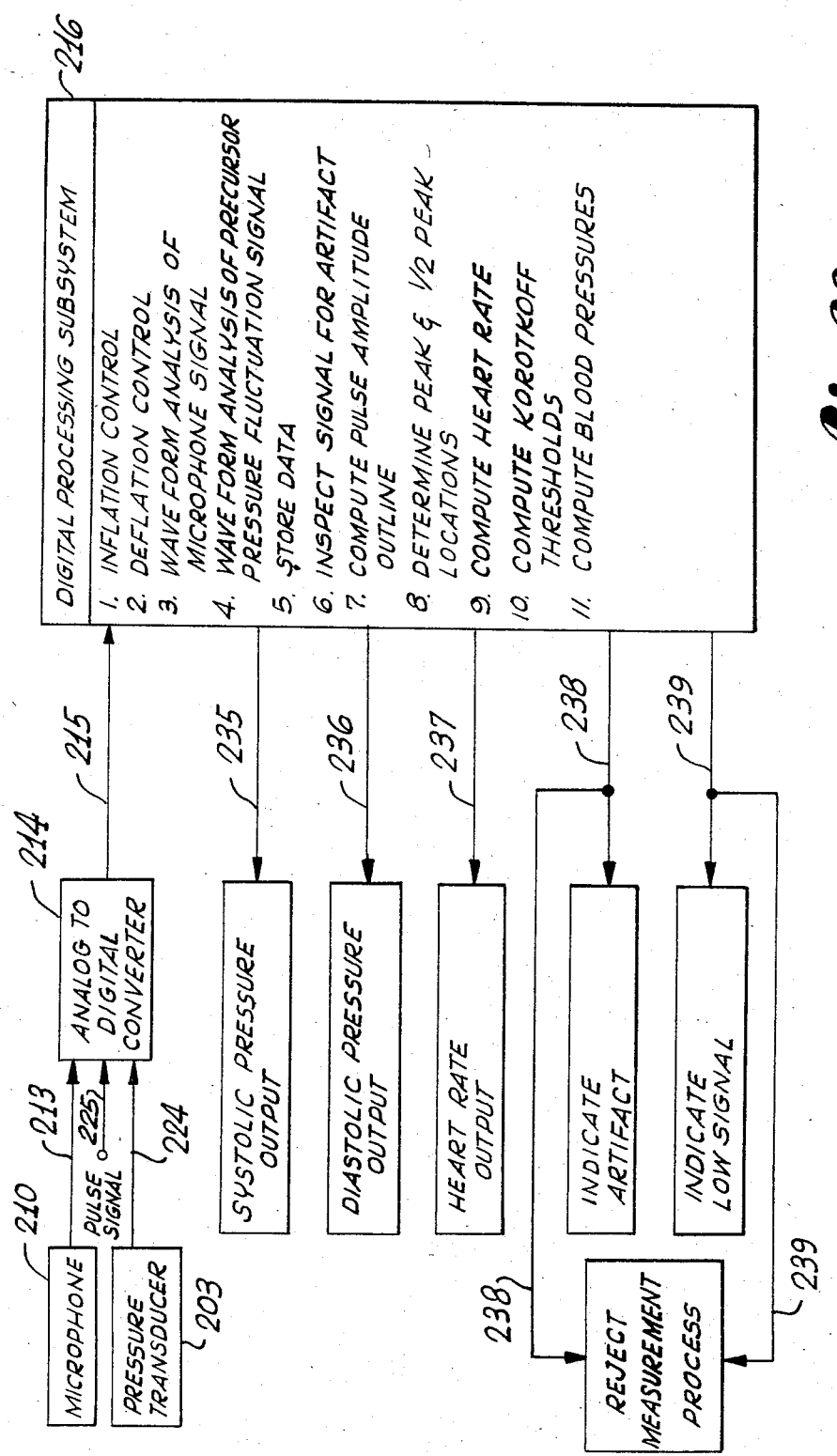
FIG. 23 is a block diagram of an overall sphygmomanometer analysis system in accordance with the invention.

FIG. 23 is a block diagram indicating in greater detail the overall sphygmomanometer analysis system, and, in particular, the functions performed by the digital processor subsystem 216.

The cuff microphone 210 directs electrical information over line 213 to the analog to digital converter subsystem 214, while the pressure transducer 203 also directs cuff pressure information, over line 224, to the converter 214. As previously indicated, in connection with FIG. 22, the analog to digital converter subsystem 214 also receives the precursor pulse waveform signal over line 225. The analog to digital converter subsystem 214, in turn, supplies digitized information over line 215, on a time shared basis, to the digital processing subsystem 216. In accordance with the invention, the digital processing subsystem 216 performs the following operations:

(1) Inflation control including initiation and termination.
(2) Deflation control including initiation, termination and dumping of cuff pressure.
(3) Waveform analysis of the microphone signals to obtain a korotkoff signal spectrum.
(4) Waveform analysis of the precursor pulse pressure waveforms.
(5) Storage of data.
(6) Inspection of korotkoff sound signals and precursor pulse wave signals for artifacts
(7) Computation of pulse wave amplitude outline.
(8) Determination of the peak and one-half peak amplitude locations in the smoothed data represented by the pulse wave amplitude outline.
(9) Computation of heart rate.
(10) Computation of korotkoff sound signal thresholds.
(11) Computation of systolic and diastolic blood pressures by extrapolation of korotkoff sound signal data.

The digital processing subsystem 216, in performing the aforementioned functions, generates a plurality of outputs in accomplishing the measurement process. Systolic and diastolic blood pressure outputs are provided over lines 235 and 236, respectively, while the heart rate computed from the average precursor pulse period is provided as an output over line 237.

In the event that the digital processing subsystem 216 determines that there are too many artifacts or too much noise in the korotkoff sound signals or the precurser waveforms, so that the measurement process is not reliable, an output is provided over line 238 which indicates the presence of an "ARTIFACT" condition and the measurement process is rejected. Similarly, if the amplitudes of the korotkoff sound signal data are too small for adequate reliability in the measurement process, then an output is provided over line 239 indicating a "LOW SIGNAL" condition and, again, the measurement process is rejected. In this way, the overall sphygmomanometer system provides accurate output indicating blood pressure and heart rate whenever the data is determined to be reliable, and will not provide misleading output when the the data is considered to be unreliable. In the latter instance, rejection of the measurement process by the system will normally inform the operator of the nature of the problem so that the process can be repeated until reliable data is obtained.

Figure 24:
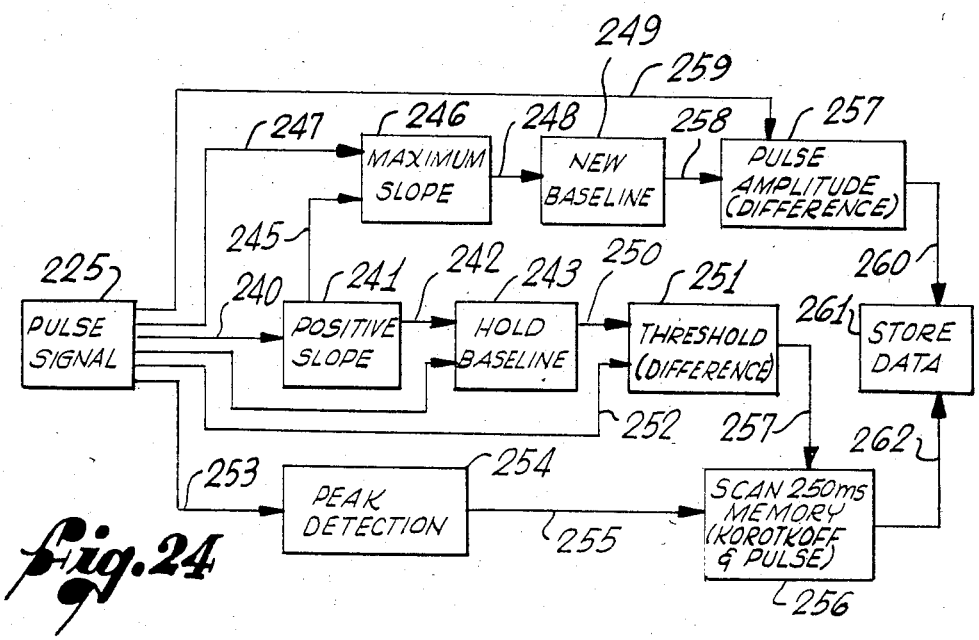
FIG. 24 is a block diagram of a subsystem for performing waveform analysis upon the incoming precursor blood pressure pulse signals.

Referring now to FIG. 24 of the drawings, there is shown a subsystem for performing waveform analysis upon the incoming precursor blood pressure pulse signals. Of course, it will be appreciated that the subsystem shown in FIG. 24 may be implemented by either hardware or software, with a programmed microprocessor being preferred for implementing the various subsystem functions.

The pulse signal 225 is directed over line 240 to a positive slope detector 241 which determines when the pulse signal waveform is on a positive rise. The output of the slope detector 241, over line 242, is directed to a subsystem 243 for holding the first baseline (the point A in FIG. 14), the baseline subsystem also receiving the pulse signal itself over line 244. The output of the positive slope detector 241 is also directed over line 245 to a maximum slope detector 246 which also receives the pulse signal 225 as input over line 247. The detector 246 locates the point C in FIG. 14 which is the steepest slop on the positive rise of the precursor pulse waveform. The maximum slope detector 246 directs input over line 248 to a subsystem 249 for determining the new baseline (point D in FIG. 14) which is 64 ms. prior to the point of steepest slope.

The electrical output from the first baseline determination is directed over line 250 to a threshold detector 251 which determines the difference between the first baseline signal at point A in FIG. 14 and the pulse signal amplitude monitored over line 252. The threshold test is represented by the point B in FIG. 14 and is one of the criteria for acceptance or non-acceptance of a pulse signal to certify the pulse signal as genuine.

The pulse signal is also directed over line 253 to a peak detector 254 which determines the location of the point F in FIG. 14 and provides input over line 255 to the control subsystem 256 for scanning approximately 250 ms. back in memory for both the korotkoff sound signals and the pressure pulse signals. The control system 256 is also enabled by output from the threshold detector 251 over line 257.

A pulse amplitude subsystem 258 measures the difference between the pulse signal waveform received over line 259 and the second baseline reference on line 263, and is constantly updated to provide a maximum reading and thereby determine the magnitude of the waveform amplitude at point E in FIG. 14, the output of the pulse amplitude subsystem being directed over line 260 as input to the data storage subsystem 261 which, of course, is scanned over line 262 by the scanning control subsystem 256.

Figure 25:
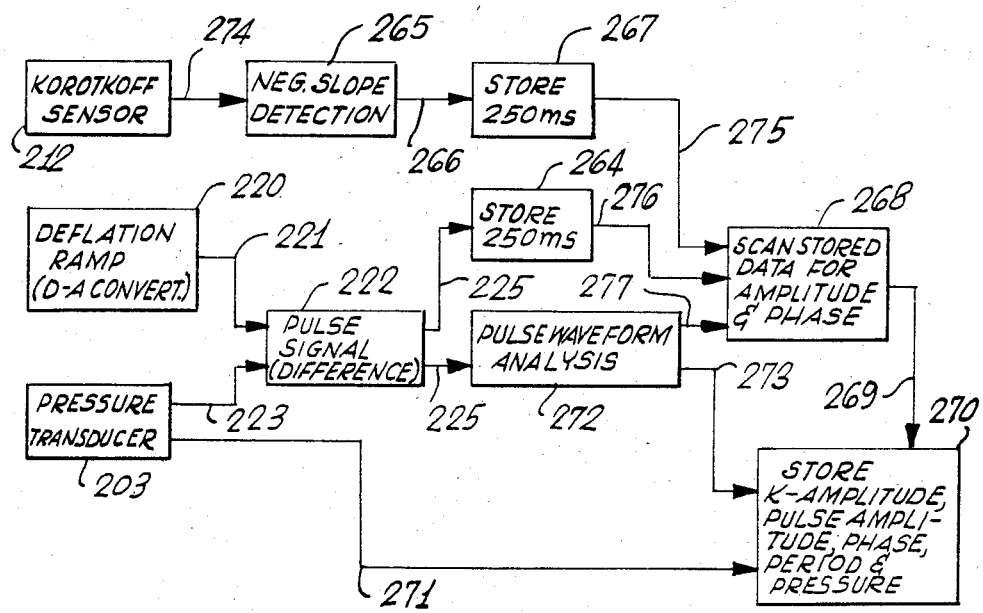
FIG. 25 is a block diagram of a subsystem for performing signal waveform analysis during the deflation process.

Referring now more particularly to FIG. 25, there is shown a block diagram of a subsystem for performing signal waveform analysis during the deflation process, immediately following the pump-up phase for inflating the pressure cuff.

In FIG. 25, the pulse waveform analysis subsystem 272 is more explicitly described in connection with the subsystem shown in FIG. 24, previously discussed. The pulse signal 255 is obtained as the difference signal, available at the output of the error junction 222 in FIG. 22, which receives as electrical inputs the deflation ramp from the digital to analog converter 220 and the electrical output from the pressure transducer 203 over lines 221 and 223, respectively.

The pulse signal 225, in addition to going through the pulse waveform analysis subsystem 263 is also directed to a memory 264 which is a first in-first out memory for storing the pulse waveforms for approximately 250 ms. Similarly, the electrical output from the korotkoff sensor 212 is directed over line 274 to a negative slope detector 265. In this regard, it will be appreciated that the slope detector may be either negative or positive depending upon the electrical polarity of the waveform.

The output of the slope detector 265 is directed over line 266 to a memory 267 which stores the korotkoff sound signal spectrum, again in a first in-first out memory so that only the last 250 ms. of information is stored, and this information is constantly updated.

Storage is done on the korotkoff sound signals at a rate of one sampling approximately every two milliseconds, whereas storage is done on the pulse wave signal approximately once every eight milliseconds, in the presently preferred embodiment of the invention.

A control system 268, for scanning stored data for amplitude and phase (the phase ratio signal X/Y) is under the control of pulse waveform analysis subsystem 272 over line 277 for scanning the data stored in the memories 267 and 264 over lines 275, 276, respectively. The scanning control system 268 feeds amplitude and phase information over line 269 to the storage subsystem 270 which also receives information over line 273 from the pulse waveform analysis subsystem 272 and over line 271 from the pressure transducer 203. Hence, korotkoff sound signal slope amplitude, pulse signal amplitude, the phase ratio signal, pulse signal period and cuff pressure are stored for subsequent analysis by the digital processing system.

Figure 26:
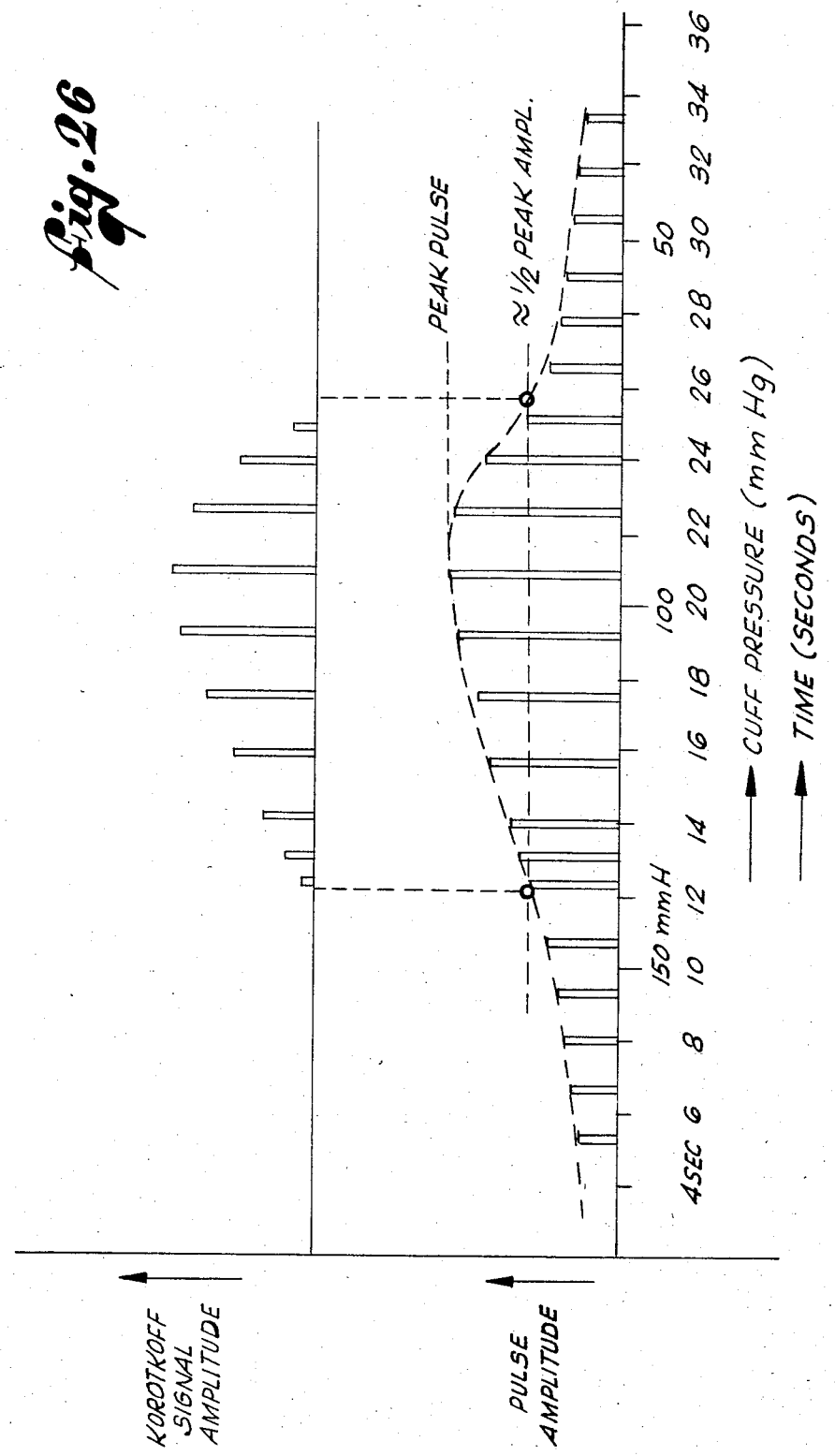
FIG. 26 is a graphical representation of pulse waveform amplitudes and korotkoff signal amplitudes, in the cuff pressure and time domains, obtained as a result of the waveform analysis and processing achieved by the subsystems of FIGS. 24 and 25.

FIG. 26 illustrates a graphical representation of the pulse waveform amplitudes and the korotkoff sound signal amplitudes (slope amplitudes) in the cuff pressure and time domains, obtained as a result of the waveform analysis and processing accomplished by the subsystems of FIGS. 24 and 25. FIG. 26 indicates the relationship between the pulse wave amplitudes and the korotkoff sound signal amplitudes and graphically illustrates the approximate correspondence between the korotkoff sound signal occurrences and the one-half peak amplitude points on the pulse amplitude outline. FIG. 26 also illustrates that the amplitude of the korotkoff sound signals and the pulse waves vary similarly in the time and cuff pressure domains, and occur almost in synchronism.

While FIG. 26 may appear to be a justification of the accuracy of the oscillometric method of blood pressure measurement, it is to be understood that the oscillometric technique using the half-peak amplitude points on the pulse amplitude outline are, at best, only approximations in determining systolic and diastolic blood pressures. In this regard, measurements on individual patients can vary widely and provide sufficient data scattering so that it becomes clear that the auscultation technique utilized in the present invention for determining blood pressures is more consistently reliable in providing accurate measurements.

Figure 27:
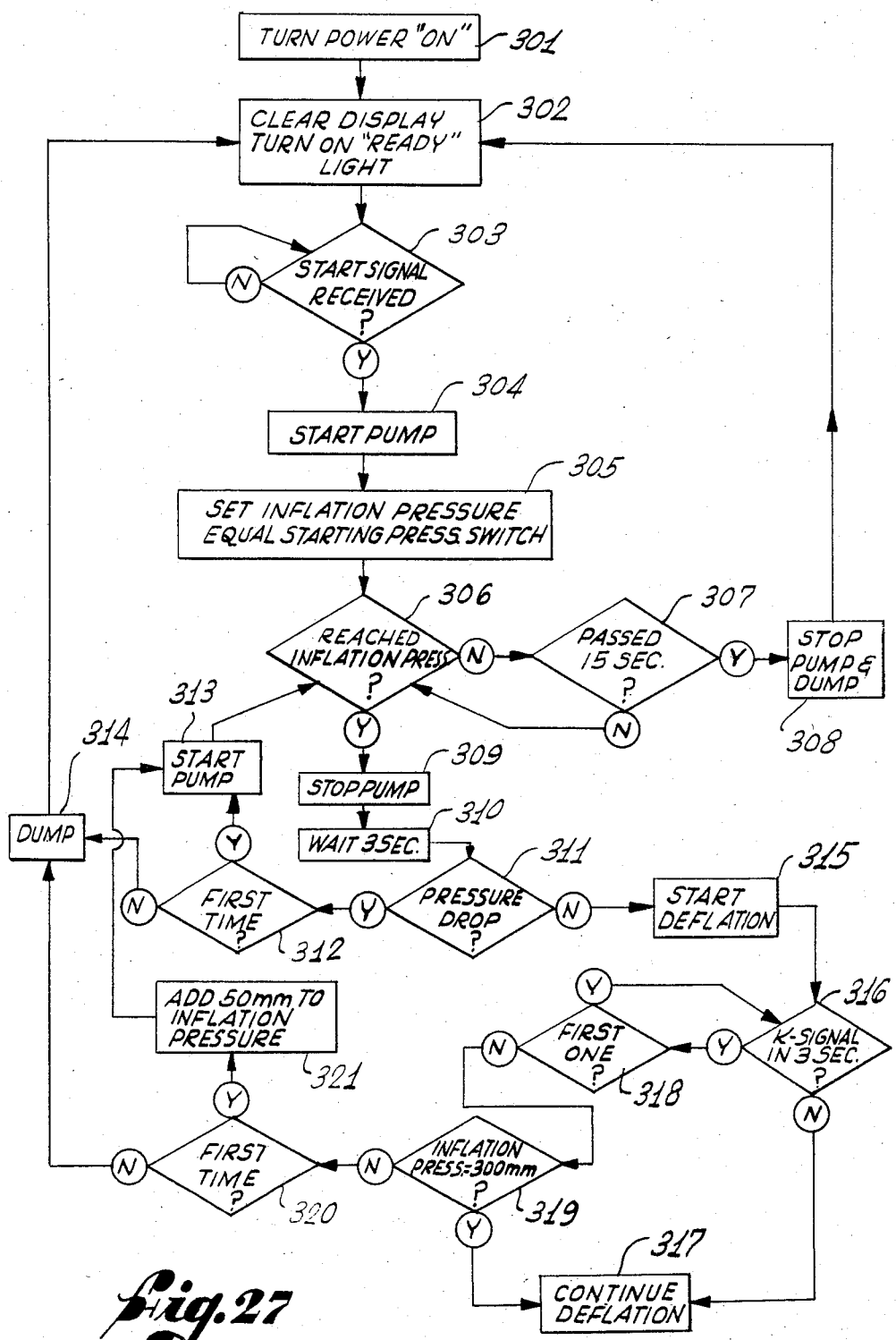
FIG. 27 is a flow chart illustrating the start-up process for inflation and deflation by the digital processing system.

FIG. 27 is a flow chart illustrating the start-up process for inflation and deflation by the digital processing system.

In step 301, system power is turned "ON", and the next step 302 clears the display system and turns on the "READY" light to indicate to the operator that the system is ready to initiate a measurement cycle. Step 303 checks for the presence or absence of the "START" signal generated when the start button (not shown) is activated. The process does not proceed further until the "START" signal is finally received. When the "START" signal has been received, the automatic air pump under the control of the digital processor system is started, in step 304, to inflate the cuff on the arm of the patient, and typically an "INFLATE" light will be energized to again inform the operator of the particular stage of the measuring process taking place.

After the inflation process has started in step 304, inflation continues to inflate the pressure cuff to the pressure value set by a starting pressure selection switch in step 305, the typical selected values being 150, 200, 250 or 300 mm. Hg. In step 306, the question is asked whether or not the inflation pressure has reached the selected inflation starting pressure. If the answer is "No", the question is asked at 307 whether or not 15 seconds have passed and, if not, the inflation pressure is again tested at 306, until either 15 seconds have elapsed, or the inflation pressure has, in fact, reached the prescribed pressure level.

If 15 seconds do elapse before the inflation pressure has reached a sufficient level, then the answer question 307 is "Yes", indicating some inflation problem exists and, therefore, the system proceeds to step 308 which stops the pump and dumps the air pressure from the cuff to abort the measurement process, the system returns to the "READY" state in step 302 to begin a new measurement cycle.

If the answer to question 306 is "Yes", indicating that the preselected inflation pressure has been reached in less than 15 seconds, the pump is turned off in step 309. The system then waits for 3 seconds in step 310 after turning off the pump. After 3 seconds, which is sufficient to allow the pump to coast to a stop and permit transients to decay away, the pressure is again measured in step 311 to determine whether or not there has been a significant pressure drop.

If the answer to question 311 is "Yes", then step 312 inquires as to whether or not this is the first time there has been such a pressure drop. If the answer is affirmative, the pump is restarted in step 313 and pumped up again to the desired inflation pressure. The need for this repumping may occur, for example, on a large arm where a great deal of air has been pumped into the inflation bladder of the cuff, so that the air is heated up during the pumping process and subsequently cooled down to cause a pressure drop. Under these circumstances, a small amount of repumping would be normal.

If the answer to question 312 is negative, indicating some problem with the inflation cycle, then step 314 is initiated to stop the pump, dump the air pressure in the cuff and return the system to the "READY" state in step 302. Essentially, the latter is a leak detection subroutine.

If no pressure drop is detected in step 311, step 315 starts the deflection process and the question is asked at 316 whether or not a korotkoff signal has been detected in the first three seconds. If the answer to question 316 is "No", the system proceeds to step 317 to continue the deflation process. On the other hand, if the answer to question 316 is "Yes", the question is asked at 318 whether or not the korotkoff signal detected was the first detected signal. If this was the first korotkoff signal, then the system returns to step 316 and waits for a second korotkoff signal. If tthere is a second korotkoff signal within the first 3 seconds, then the answer to question 318 will be "No", and the system proceeds to step 319 which inquires whether or not the inflation pressure equals 300 mm. Hg., which is the maximum inflation pressure allowed by the system. If the answer to question 319 is "Yes", deflation is continued in step 317.

If the inflation pressure is below 300 mm. Hg., the question is asked at 320 whether or not the 300 mm. Hg. test is being applied for the first time. If it is the first time, 50 mm. Hg. is added to the inflation pressure memory in step 321, the pump is restarted in step 313, and the system returns to step 306 to determine whether the inflation pressure has been reached.

If the test at 319 has been applied more than once, indicating a prior supplementary pump up of 50 mm. Hg. as determined by step 320, step 314 is again initiated to stop the pump, dump the air pressure in the cuff and return the system to step 302 for a new measurement cycle.

Figure 28:
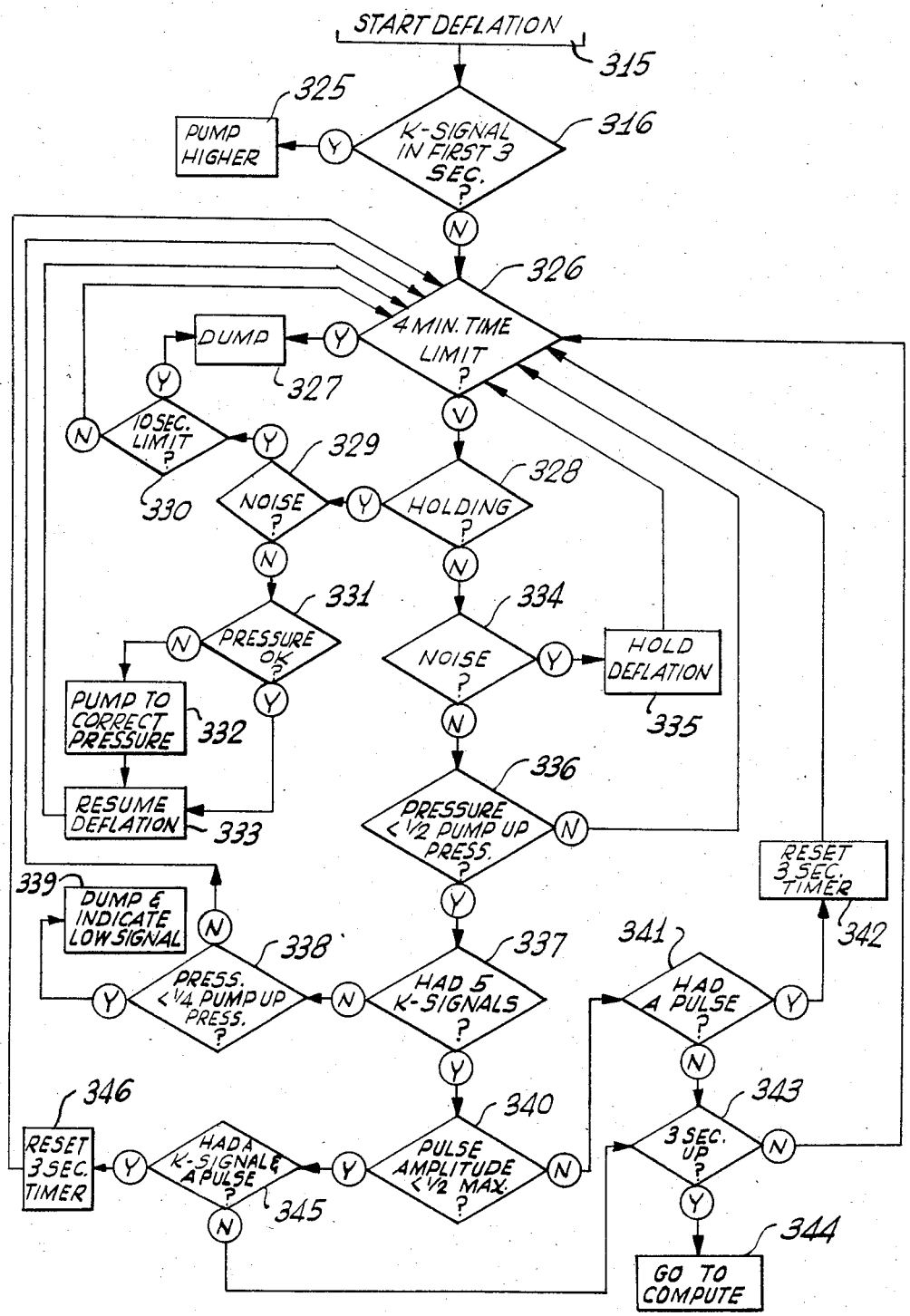
FIG. 28 is a flow chart illustrating the deflation control process implemented by the digital processing system.

FIG. 28 is a flow chart illustrating in greater detail the deflation control process implemented by the digital processing system. In step 315, the aforementioned deflation process is carried out and, of course, the korotkoff sound signals occurring in the first 3 seconds are monitored in step 316. If korotkoff signals are detected in the first 3 seconds, then step 325 is a simplified version of the procedure in FIG. 27 for determining whether or not the cuff should be pumped higher or dumped.

If the answer to question 316 is negative, indicating that no korotkoff signals have appeared in the first 3 seconds after initiation of the deflation process, the question is asked in step 326 whether or not a 4 minute time limit has been exceeded, in order to protect the patient against extended occlusion of the brachial artery which results in congestion of the arm.

It will be apparent from step 326 that the 4 minute time limit test is applied repetitively in a plurality of subroutines to protect the patient continuously against excessive occlusion from a lengthy measurement cycle. If the 4 minute time limit has been exceeded, then the answer to question 326 is "Yes" and the system proceeds to step 327 to dump the pressure in the cuff.

If the 4 minute time limit in step 326 has not been exceeded, then step 328 inquires regarding whether or not the system is in the "HOLDING" mode, which means that the deflation process has stopped but the cuff pressure has not been dumped, as where there has been a noise detected in either the korotkoff signal or the precursor pressure waveform. If the answer to the question 328 is "Yes", step 329 asks whether or not there is still a noise while the system is holding, and, if any noise exists, a 10 second time limit is applied in step 330. If the 10 second time limit for noise has been exceeded, then the system proceeds to step 327 which dumps the cuff pressure. If the 10 second time limit for noise has not been exceeded, the system recycles to the 4 minute time limit test in step 326.

If, during "HOLDING", the noise has gone away, so that the answer to question 329 is "No", the actual pressure in the cuff is compared in step 331 with the pressure at the point of entry into the "HOLDING" mode. If the pressure has dropped for some reason below that point, the system pumps up again to correct pressure in step 332, resumes deflation in step 333, and returns to the 4 minute time limit test in step 326.

If the pressure test in step 331 is okay, the system proceeds directly to step 333 to resume deflation. If it is determined in step 328 that the system is not in the "HOLDING" mode, the question is asked at 334 whether or not there is any noise, and, if there is, the system goes into the hold delfation mode in step 335 and back up to the 4 minute time limit test 326 which is central to the loop.

If step 334 determines that there is no noise, inquiry is made at 336 regarding whether or not the pressure is half of the starting pump-up pressure. If the pressure has not gone below the latter reference level, the system returns again to step 326 to repeat the loop. If, on the other hand, the pressure has gone below that level, step 337 inquires whether or not 5 korotkoff signals have been detected. If the answer is "No", the question is asked at 338 whether or not the pressure has dropped below one-quarter of the initial pump-up pressure. If the pressure has not dropped below one-quarter of the initial pump-pressure, the system returns to step 326 to go through the loop again. If, on the other hand, the pressure has dropped below one-quarter of the pump-up pressure, the system proceeds to step 339 which dumps the cuff pressure and indicates a "LOW SIGNAL".

If the answer to question 337 is "Yes", the question is asked at 340 whether or not the precursor pulse amplitude is less than half of the peak pulse amplitude that has been observed thus far in the process. If the answer is "No", the system searches for additional pulses in step 341. If additional pulses are detected, a 3 second timer is reset in step 342 and the loop is repeated through step 326. If no additional pulses are detected in 3 seconds, in step 343, the system exits to the computational phase of the process in step 344. If the 3 seconds are not yet up, the loop is repeated through step 326.

If the pulse amplitude is below one-half of the maximum amplitude, and the answer to question 340 is "Yes", an inquiry is made at 345 regarding whether or not a korotkoff signal and a pressure pulse have been detected in a 3 second time period. If the answer is "Yes", the 3 second timer is reset in step 346 and the loop is repeated through step 326. If the answer to question 341 is "No", the 3 second limit is applied in step 343 as previously described in the evaluation of additional pulses alone. Hence, if the system is below one-half of the maximum pulse amplitude and no more korotkoff signals and concurrent pressure pulses are detected within 3 seconds, the system exits the routine to the "COMPUTE" mode.

Figure 29:
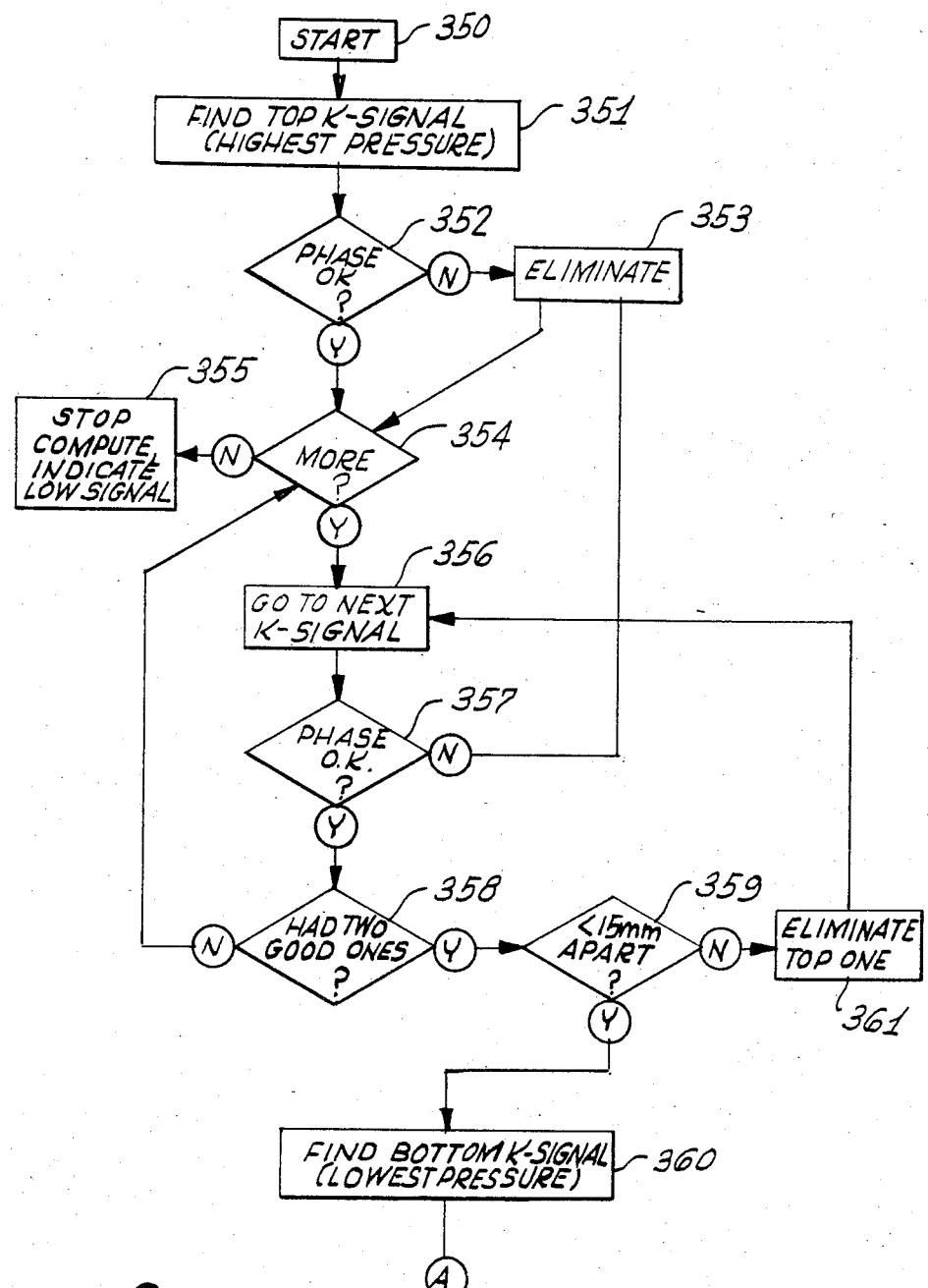
FIG. 29 is a flow chart illustrating the elimination of spurious korotkoff signals by the digital processing system.

FIG. 29 is a flow chart illustrating the elimination of spurious korotkoff signals by the digital processing system and represents the beginning of the computation process. The routine is started at 350 and, in step 351, locates in the memory records the korotkoff signal corresponding to the highest cuff pressure.

In step 352, the phase of the korotkoff signal relative to the associated precursor pulse waveform is checked and, if the phase test is failed, then that korotkoff signal is eliminated from further consideration in step 353 but not eliminated from memory.

If the phase of the korotkoff signal is okay, step 354 asks whether there are more signal records in memory. If the answer is "No", the routine is stopped in step 355 and a "LOW SIGNAL" is indicated. If there are more signals, examination proceeds to the next korotkoff signal (in the direction of decreasing cuff pressure) in step 356. Again, the phase test is applied in step 357. If the test is failed, that particular korotkoff signal is eliminated from further consideration in step 353. If the phase test is passed, the question is asked at 358 whether or not there have been two good korotkoff signals. If the answer is "No", the system returns to step 354 for determination of whether there are any more korotkoff signals.

If the answer to question 358 is "Yes", inquiry is made in step 359 whether or not the two good korotkoff signals are less than 15 mm. Hg. apart. If the answer to the latter question is "Yes", the korotkoff signals are accepted at the top end of the pressure spectrum for subsequent systolic pressure determinations. If the korotkoff signals are more than 15 mm. Hg. apart, the top korotkoff signal is rejected as a spurious signal in step 361 and the system returns to step 356 to proceed to the next korotkoff signal. This process continues until two korotkoff signals are located which pass the phase test and are less than 15 mm. Hg. apart. If an acceptable korotkoff signal pair is not located, the system passes from step 354 to step 355 to end the routine and indicate a "LOW SIGNAL".

Figure 30:
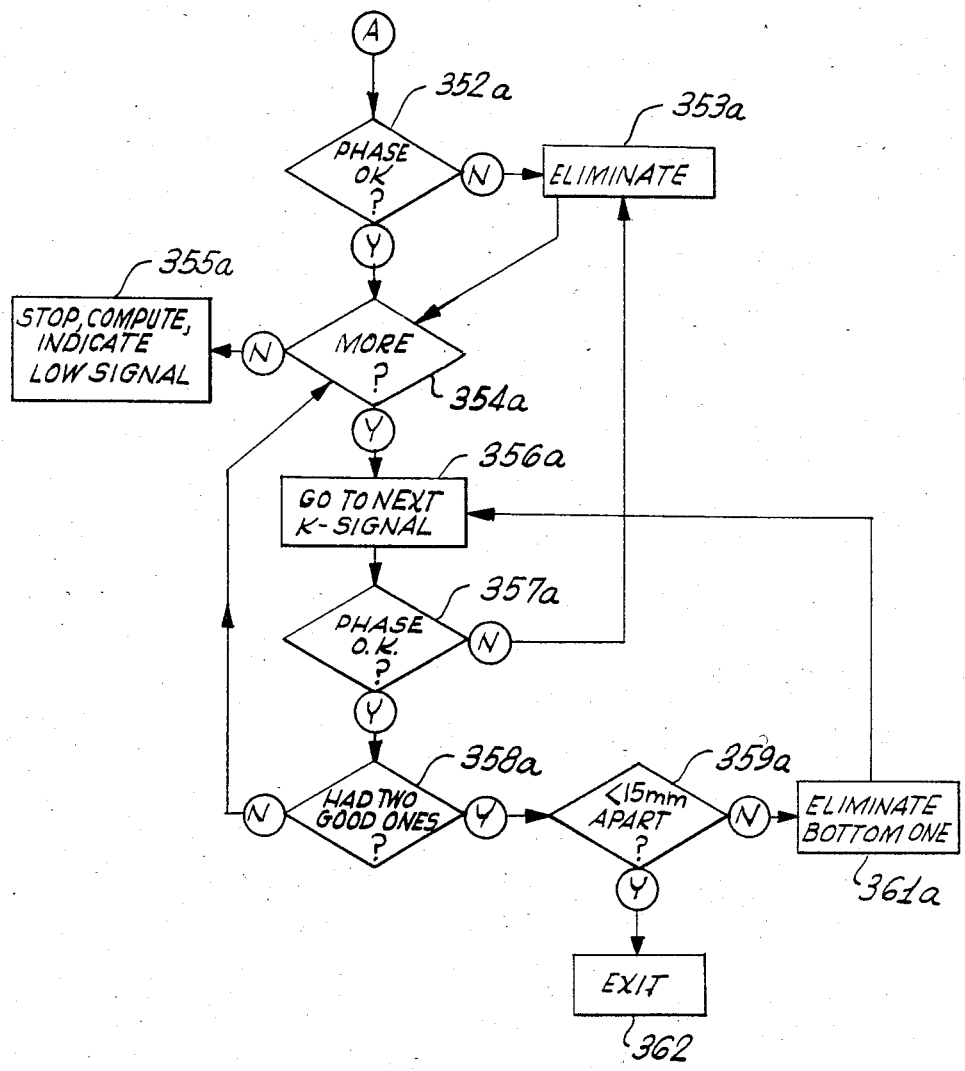
FIG. 30 is a flow chart illustrating additional steps in the elimination of spurious korotkoff signals by the digital processing system.

Once the test in step 359 has been successfully completed, the system moves on to step 360 which repeats the process shown in FIG. 29 for the diastolic or low pressure end of the pressure spectrum, as illustrated in FIG. 30.

As shown in FIG. 30, the process for the location of a pair of acceptable korotkoff sound signals less than 15 mm. Hg. apart at the diastolic end of the spectrum, is virtually identical to the process for the systolic end, except that the search is in the direction of increasing cuff pressure rather than decreasing cuff pressure, and the phase tests use different thresholds. In this regard, steps 352a–361a in FIG. 30 are counterparts of steps 352-361 in FIG. 29, recognizing the step 361a eliminates the bottom korotkoff signal (rather than the top in step 361) where two korotkoff signals are spaced more than 15 mm. Hg. apart. Once a pair of acceptable korotkoff sound signals have been found at the diastolic end of the pressure spectrum, the routine exits via step 362 for further computation.

Figure 31:
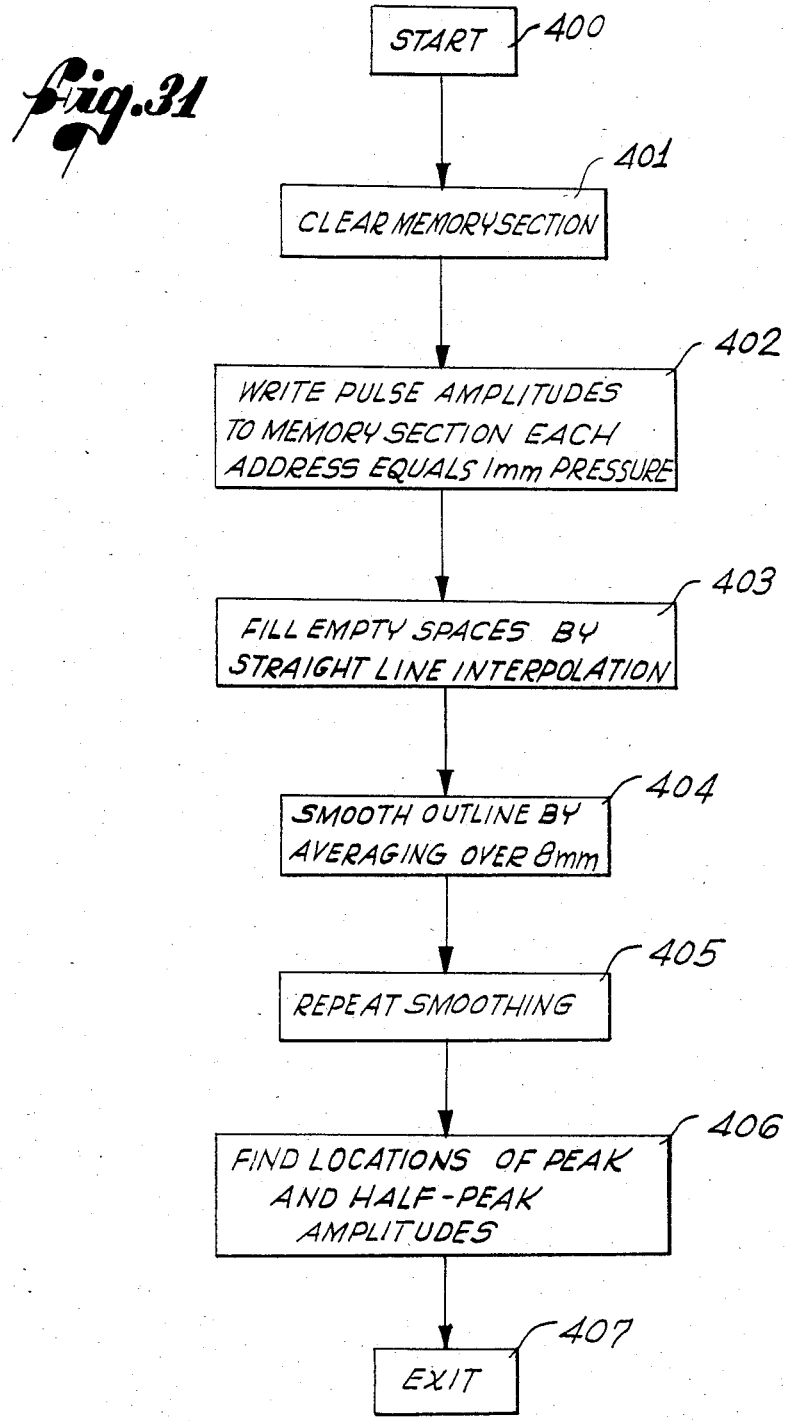
FIG. 31 is a flow chart illustrating the process of pulse amplitude data manipulation to draw the outline of the pulse amplitude spectrum, as implemented by the digital processing system.
Figure 32:
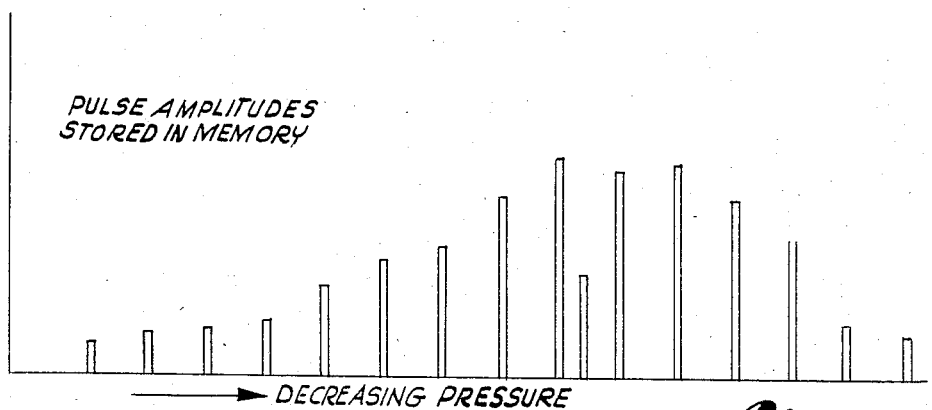
FIGS. 32, 33 and 34 are graphical representations regarding the smoothing of data and provision of a pulse amplitude outline, as implemented by the digital processing system.
Figure 33:
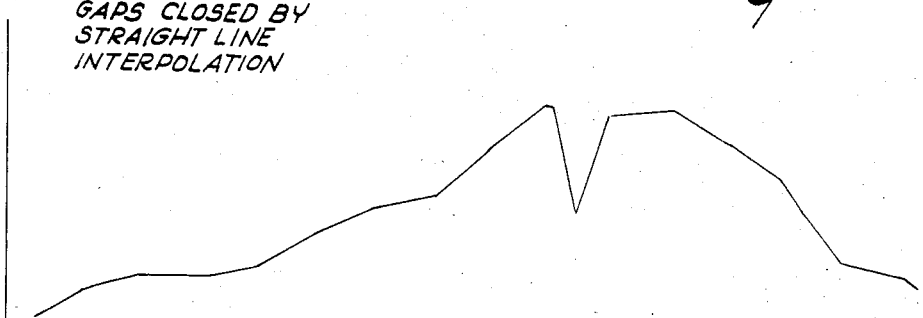
Figure 34:
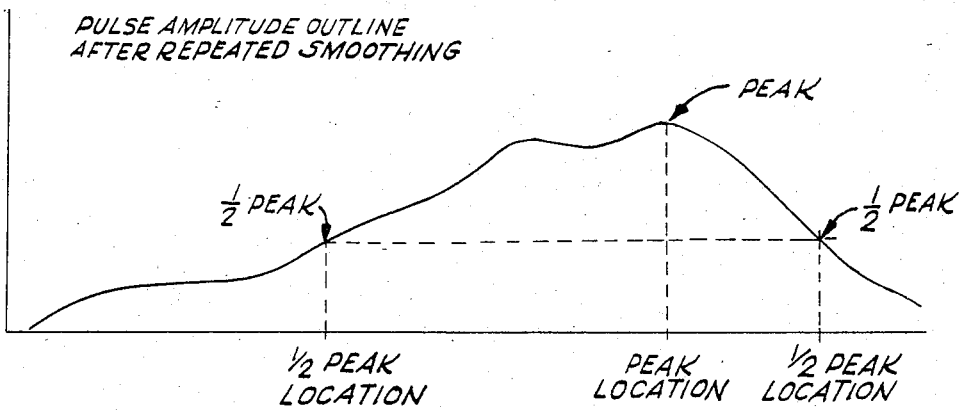

FIG. 31 is a flow chart illustrating the process of pulse amplitude data manipulation to draw the outline of the pulse amplitude spectrum, in smoothing of data and provision of a pulse amplitude outline, as shown in FIGS. 32-34.

The routine starts in step 400 and moves to step 401 which clears the memory storage locations for pressure pulse data and moves on to step 402 where the pulse amplitudes are located in locations corresponding to cuff pressure, in increments of 1 mm. Hg. pressure. Step 402 essentially produces the graphical representation of FIG. 32 regarding the pulse amplitude spectrum in the pressure domain with the abscissa having a resolution of 1 mm. Hg. pressure.

In step 403, the bar diagram of FIG. 32 is converted to the continuous curve depiction of FIG. 33 by straight line interpolation between adjacent pulses.

In step 404, the outline in FIG. 33 is smoothed by averaging over eight abscissa locations, or 8 mm. Hg., and the process of smoothing is repeated again in step 405 to produce the pulse amplitude outline, after repeated smoothing, shown in FIG. 34 of the drawings.

In step 406, the peak and half-peak amplitudes for the pulse amplitude outline in FIG. 34 are located, as in the oscillometric technique, and the routine exist at step 407.

Figure 35:
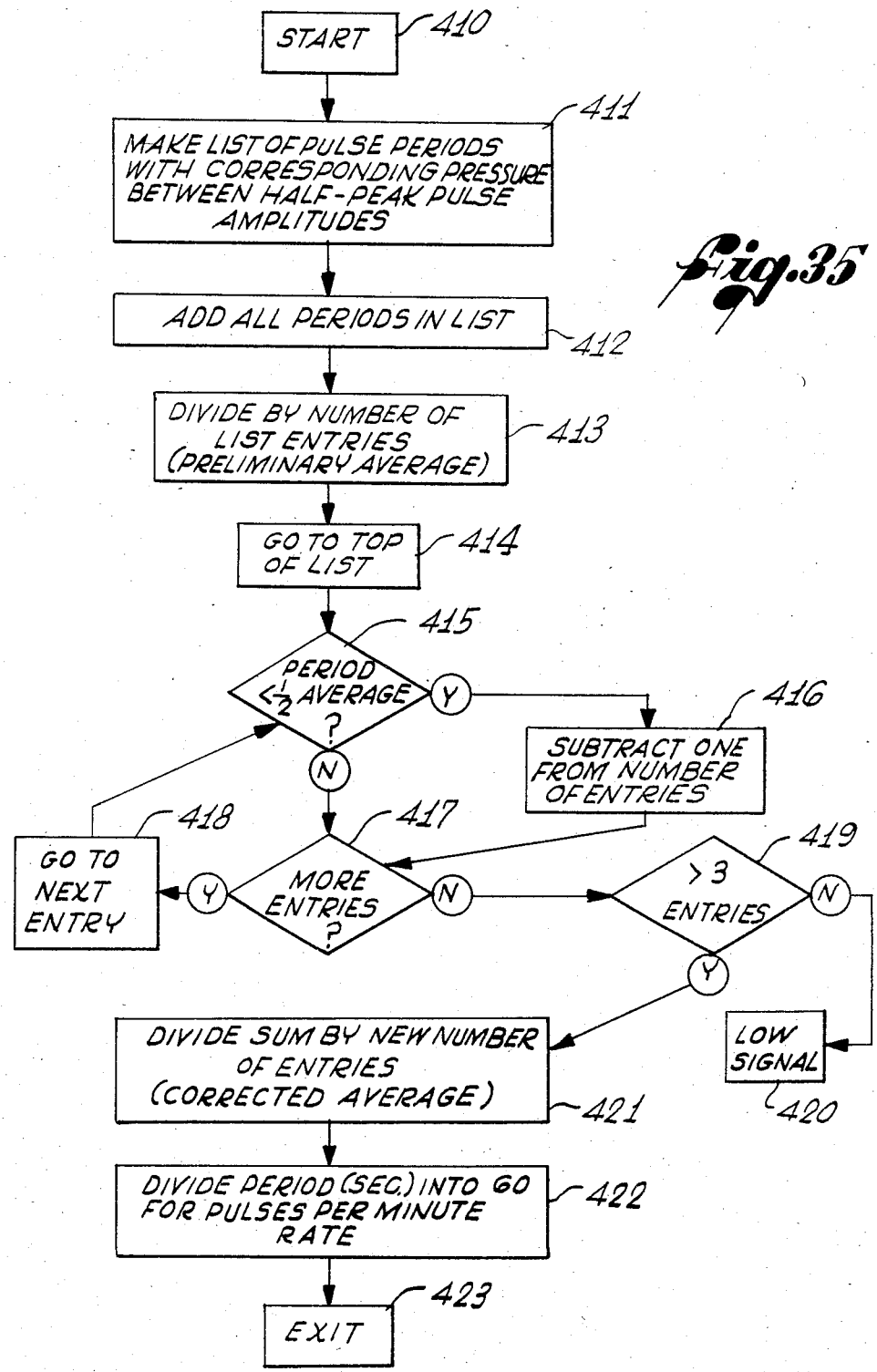
FIG. 35 is a flow chart illustrating the determination of pulse rate by the digital processing system.

FIG. 35 is a flow chart illustrating the determination of pulse rate by the digital processing system. The pulse rate determination routine begins at step 410 and moves on to step 411 which lists all of the pulse periods between the half-peak pulse amplitudes previously determined in connection with the routine of FIG. 31.

In step 412, all the periods in the list are added, and, in step 413, the sum is divided by the number of list entries to obtain a preliminary average. In step 414, the list is scanned from the top and each entry in the list is compared with the average computed in step 413. In step 415, each entry is tested to determine whether or not it is less than one-half of the previously computed average. If there are two pulses very close together, it is assumed to be an artifact and, therefore, if the answer to the question at 415 is "Yes", a single pulse period is subtracted from the number of entries on the list, in step 416. If there are more entries, determined by step 417, then the system proceeds to the next entry in step 418 and returns to the loop in step 415 to test subsequent entries.

If the answer to question 415 is "No", indicating that the particular pulse period examined is greater than one-half of the preliminary average, and there are no more entries, inquiry is made at 419 whether or not there are more than three pulse period entries remaining. If the answer is "No", a "LOW SIGNAL" indication is made in step 420.

If the answer to question 419 is "Yes", indicating that there are more than three pulse period entries, the system proceeds to step 421 where the sum of the pulse periods is divided by the new number of remaining entries to obtain a corrected pulse period average. In step 422, the corrected pulse period average is divided into the number 60 to obtain heart rate in pulse per minute, and the routine exits in step 423.

Figure 36:
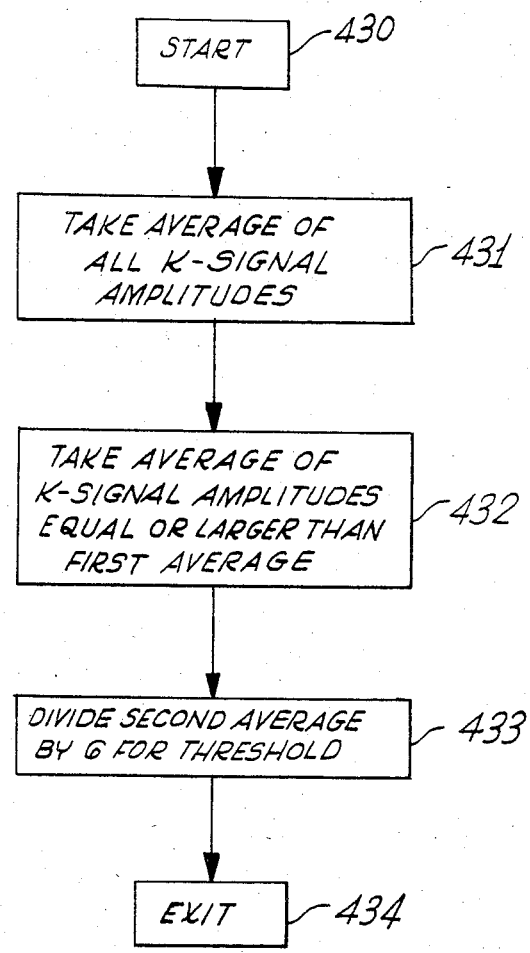
FIG. 36 is a flow chart illustrating the determination of the korotkoff signal threshold level by the digital processing system.

FIG. 36 is a flow chart illustrating the determination of the korotkoff signal threshold level by the digital processing system. The routine starts in step 430 and moves on to step 431 where all of the korotkoff signal amplitudes are averaged. In step 432, the average of all korotkoff signal amplitudes equal to or greater than the first average computed in step 431 is taken. In step 433, the second average is divided by the number 6 to determine the korotkoff signal threshold level used in the subsequent computational process for determination of systolic and diastolic blood pressures. The routine then exits via step 434.

Figure 37:
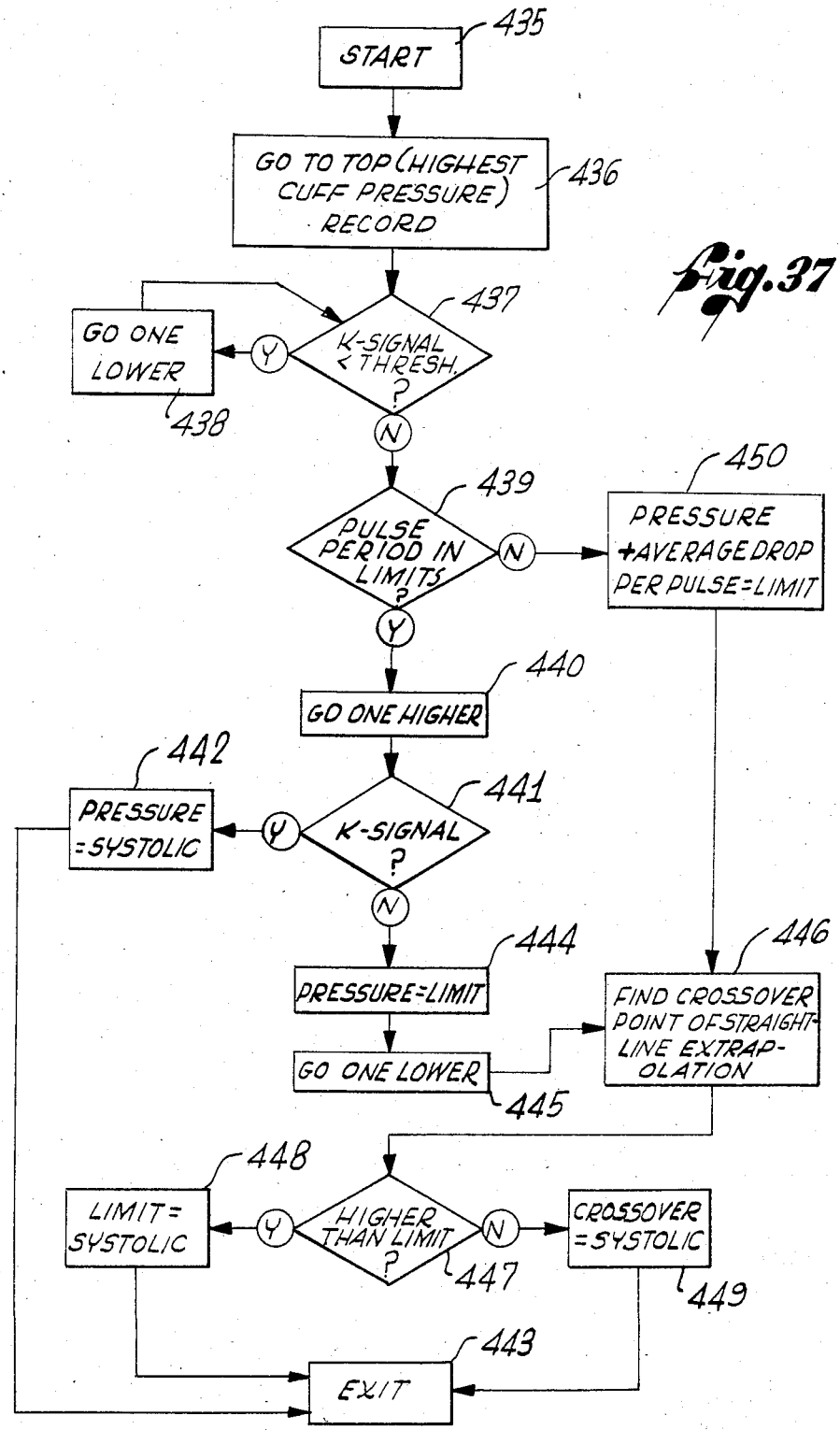
FIG. 37 is a flow chart illustrating the determination of systolic pressure by the digital processing system.

FIG. 37 is a flow chart illustrating the determination of systolic blood pressure by the digital processing system in implmenting the systolic pressure determinations previously described in connection with FIGS. 19-21 and described in additional detail in FIGS. 39 and 40.

The systolic pressure determination routine starts in step 435 and proceeds to step 436, which again locates the korotkoff signal in memory corresponding to the highest cuff pressure. Step 437 tests the korotkoff signal against the computed threshold previously described in connection with FIG. 36. If the korotkoff signal is less than the computed threshold then the system proceeds to step 438 to the next lower korotkoff sound signal and again tests that signal against the threshold.

If the korotkoff signal is above the computed threshold, the pulse period at the same location as that korotkoff signal is tested in step 439 to determine whether it is within the limits of ½ to 1½ times the average pulse period. If the test in step 439 is passed, the system looks at the data for one record position in memory higher than the korotkoff signal above threshold in step 440 and inquires at 441 whether or not a korotkoff signal exists at that memory location, regardless of the amplitude of that korotkoff signal (above or below the computed threshold). If such a korotkoff sound signal exists, and the system proceeds to step 442 which identifies that korotkoff signal location as the systolic pressure (FIG. 19) and the routine exits via step 443.

If the answer to question 441 is no, indicating that there is no korotkoff signal at the next higher record location in memory, a limit is generated in step 444 equal to the pressure of the pulse wave record at that memory location which lacks the korotkoff signal. The reasoning behind this is that the systolic pressure is believed to lie between that pressure limit and the first korotkoff signal above the computed threshold.

In step 445, the system goes to the next lower record position in memory containing the korotkoff signal above the computed threshold. Then, in step 446, a straight line extrapolation is performed between the korotkoff signal in step 445 and an adjacent korotkoff signal to locate the crossover point on the cuff pressure axis. This crossover point is tested in step 447 to determine whether it is higher or lower than the previously determined pressure limit in step 444. If it is higher than the limit, then the limit is designated the systolic pressure in step 448. If the test at 447 is negative, then the crossover point on the cuff pressure axis is deemed to be the systolic pressure.

Figure 20:
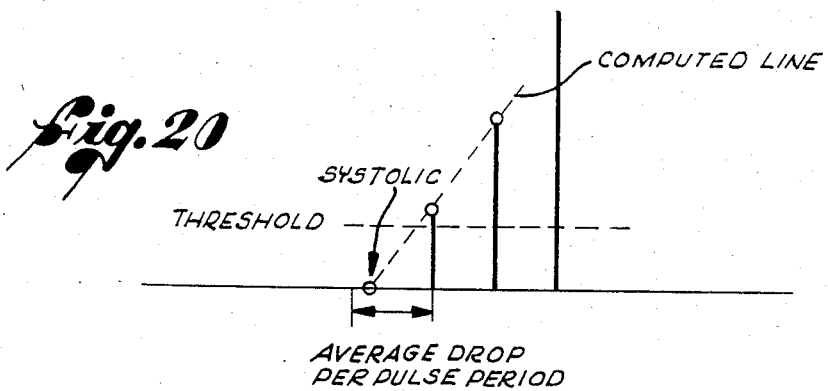
FIG. 20 is a graphical representation of typical korotkoff sound signal amplitudes which have been certified as true korotkoff sound signals by the system of the present invention, and further illustrates the extrapolation technique used in the determination of systolic blood pressure.

The systolic pressure determination in step 442 corresponds to the graphical representation of the process in FIG. 19 of the drawings, whereas the systolic pressure determinations in steps 448 and 449 correspond to the graphical representations in FIGS. 21 and 20, respectively.

If the test results in step 439 of FIG. 37 are negative, indicating that the pulse period at the location of the korotkoff signal above threshold is not within limits, then the pressure limit established in step 450 is the pressure at that korotkoff signal location plus the average pressure drop per pulse period. Thereafter, the routine proceeds to the extrapolation process in step 446 and systolic pressure is determined as previously described.

Figure 38:
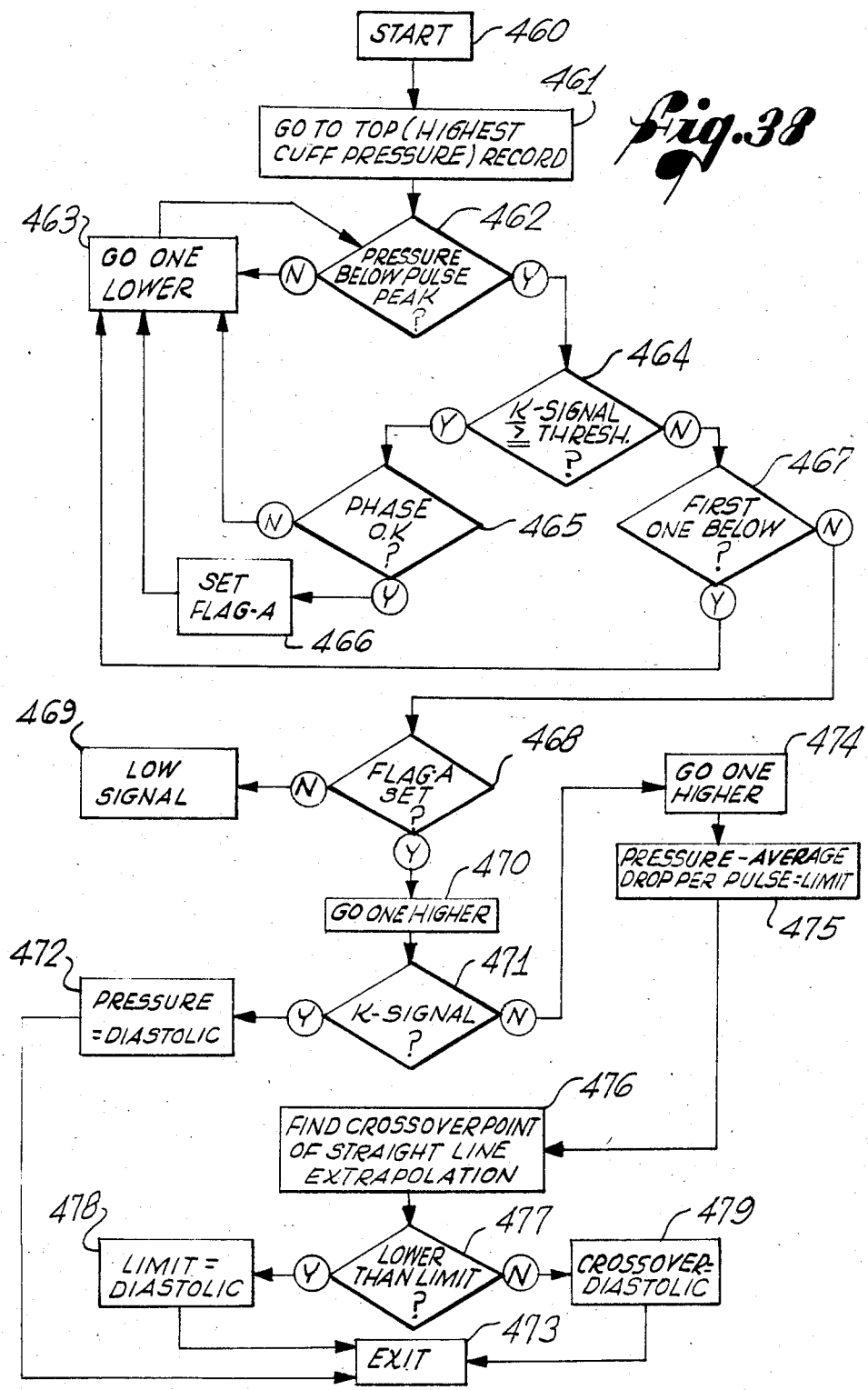
FIG. 38 is a flow chart illustrating the determination of diastolic pressure by the digital processing system.

FIG. 38 is a flow chart illustrating the determination of diastolic pressure by the digital processing system. The routine starts in step 460 and moves to step 461 which examines the pulse wave records in memory starting with the precursor pulse wave corresponding to the highest cuff pressure. These pulse pressure amplitudes are examined successively and each pulse amplitude in succession is tested at 462 to determine whether or not it is above or below the oscillometric pulse peak located on the curve of FIG. 34. If the test at 462 is negative, indicating that the pulse amplitude is above the peak, then the system passes to step 463 which moves to the next lower pulse amplitude record in the direction of diminishing cuff pressure and then tests this next pulse amplitude in step 462, until a pulse amplitude is finally located below the peak location.

When a pulse amplitude has been located which is below the pressure location corresponding to the peak amplitude, the answer to the question at 462 is affirmative and the routine moves to step 464 which asks whether or not there is a korotkoff signal at that same location which is equal to or greater than the computed korotkoff signal threshold. If the answer is "Yes", the phase of the korotkoff signal is checked at 465. If the phase of the korotkoff signal is unsatisfactory, the system returns to step 463 to move down to the next lower pressure pulse.

If the phase in step 465 is okay, then a flag A is set in step 466 before moving on to step 463 to inspect the next lower pressure pulse location. Hence, the flag A is set each time a korotkoff signal equal to or greater than the computed threshold is encountered at the location of a pressure pulse being examined, and that same korotkoff signal also passes the phase test of step 465.

The system continues to scan downward in pressure until a korotkoff signal is encountered in step 464 which is below the computed threshold. Then, in step 467, the question is asked whether or not this is the first korotkoff signal below theshold. If it is the first korotkoff signal below threshold, including a zero value at the location in memory corresponding to the asociated pulse precursor, the system goes through the loop again by returning to step 463 until a second korotkoff signal of this type below threshold is encountered. At this point step 468 inquires whether or not flag A has been set which, in essence, asks the question whether or not a korotkoff signal above threshold and with acceptable phase has been located during the diminishing pressure scan before a pair of korotkoff signals below the computed threshold were encountered. If the answer to question 468 is no, the computation is aborted and a "LOW SIGNAL" indicated in step 469.

If the test in step 468 determines that flag A had been set, the system moves up the pressure scale one record location to the next pressure pulse, via step 470. In step 471, the location determined in step 470 is tested for the presence of an actual korotkoff signal. If there is a korotkoff signal at specific location, that specific location is then determined to be the diastolic pressure in step 472, and the routine exits via step 473.

If there is no korotkoff signal at the record location in memory determined in step 470, then the system proceeds from step 471 to step 474 to the next higher record location and moves from there to step 475 which computes the lower diastolic pressure limit as the pressure at the location determined in step 474 minus the average pressure drop per pulse period. Steps 476-479 thereafter invoke the same extrapolation process for determining diastolic blood pressure as the corresponding steps 446-449, respectively, previously described in connection with FIG. 37 for determining systolic blood pressure.

Figure 39:
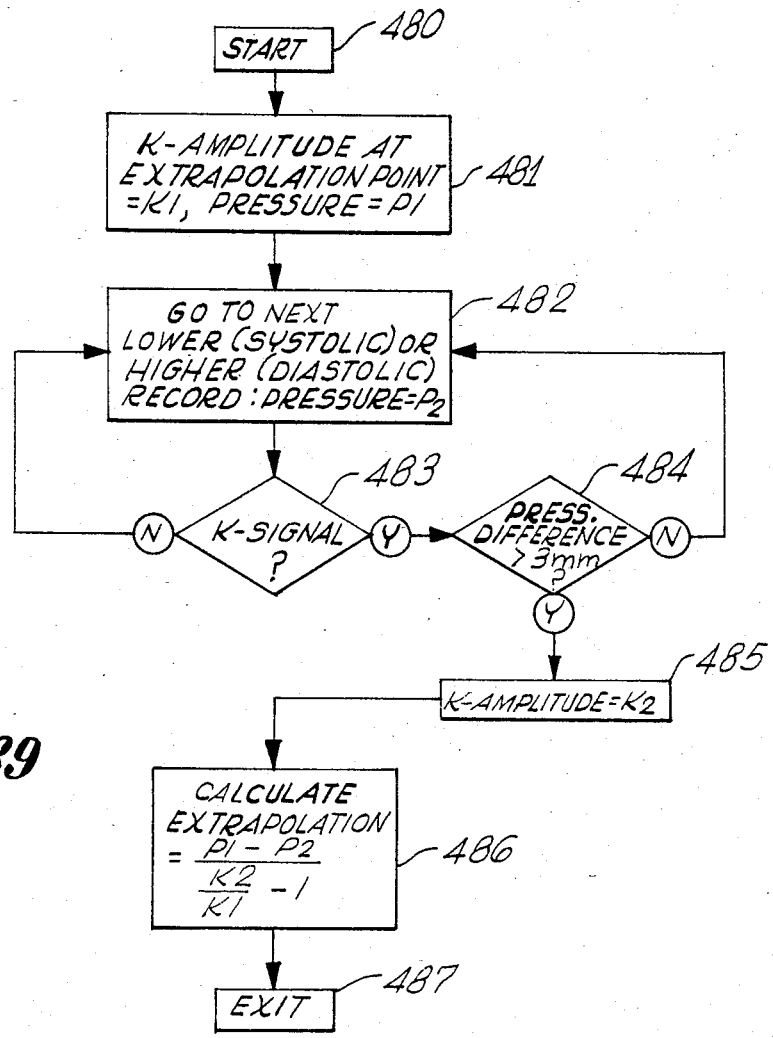
FIG. 39 is a flow chart illustrating the korotkoff signal extrapolation process implemented by the digital processing system.
Figure 40:
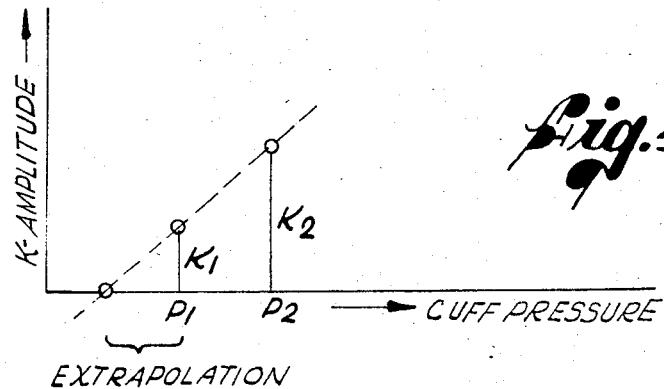
FIG. 40 is a graphical representation, further illustrating the korotkoff signal extrapolation process.

FIG. 39 is a flow chart illustrating the korotkoff signal extrapolation process utilized in determining systolic and diastolic blood pressures in the computational routines illustrated in FIGS. 37 and 38 of the drawings, and FIG. 40 is a graphical representation illustrating the korotkoff signal extrapolation process of FIG. 39.

The extrapolation routine starts at step 480 and moves to step 481 which is that step in the systolic and diastolic routines for locating the first korotkoff amplitude K1 above the computed threshold, at the cuff pressure P1. In the next step 482, the search continues to the next lower (in the case of systolic) or higher (in the case of diastolic) record in memory at the pressure peak P2. Each record location is tested at 483 to determine whether or not a korotkoff signal exists at that location and, if there is no korotkoff signal, the loop returns to step 482 until a location is obtained which does have a korotkoff signal.

When a korotkoff signal is located in step 483, it is tested in step 484 to determine whether or not the two pressures P1 and P2 are spread apart by more than 3 mm. Hg. If the pressures P1 and P2 are too close to each other, the system continues the search for a new P2 pressure value in step 482. When a location is finally found which satisfies the pressure difference test of step 484, the korotkoff signal amplitude at that location is the amplitude K2 in FIG. 37, as determined in step 485.

Step 486 calculates the extrapolation to the cuff pressure axis by drawing a straight line between the peaks of the amplitudes K1 and K2 to determine the crossover on the cuff pressure axis referred to previously as step 446 in FIG. 37 and 476 in FIG. 38.

In view of the importance of the flex sensor 103 in FIGS. 3a-3c for obtaining a clean korotkoff sound signal with a high signal-to-noise ratio and essentially devoid of blood pressure pulse and whole arm expansion signals superimposed upon the korotkoff sound signal, Applicant has designed, for the practice of the present invention, a variety of new and improved longitudinal flex sensors which are illustrated in FIGS. 41a-43b.

Figure 41A:
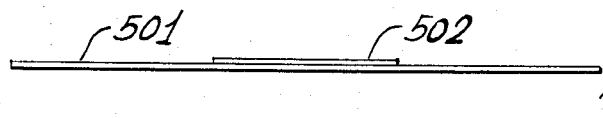
FIG. 41a is an elevational view of a longitudinal flex transducer suitable for use in sensing korotkoff sound signals, in accordance with the present invention.
Figure 41B:
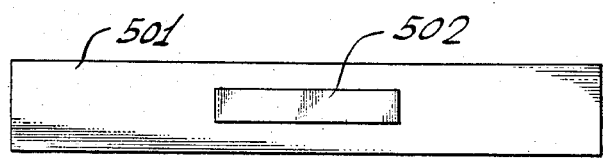

Referring now more particularly to FIGS. 41a and 41b, there is shown a flex sensor comprising a narrow strip 501 of metal or other spring material having a strain gauge 502 attached to the strip at the center of the strip where the displacement would be greatest during bending of the strip in response to the traveling wavefront of the blood rushing through the brachial artery upon the occurrence of a korotkoff event. The strain gauge 502 is directional in its response characteristics, so that response is substantially only to the lengthwise bending of the transducer.

Figure 42A:
FIG. 42a is an elevational view of an alternate embodiment of a suitable longitudinal flex transducer.
Figure 42B:
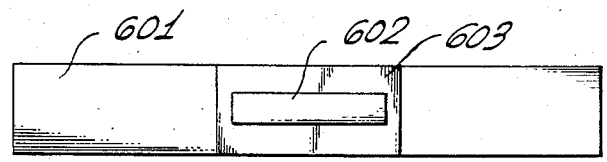

FIGS. 42a and 42b illustrate another embodiment of a flex sensor, again utilizing a strip 601 of metal or other suitable spring material upon which is mounted a piezoelectric transducer 602 at the center of the strip. Since the piezoelectric transducer 602 is typically relatively brittle, a suitable elastomeric pad 603, of rubber or the like, is positioned between the transducer 602 and the strip 601.

Figure 43A:
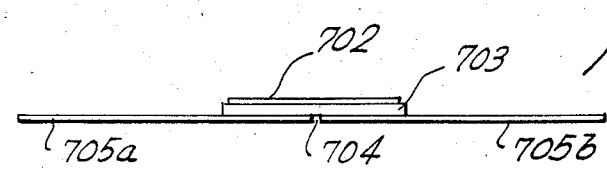
FIG. 43a is an elevational view of still another embodiment of a longitudinal flex transducer, in accordance with the present invention.
Figure 43B:
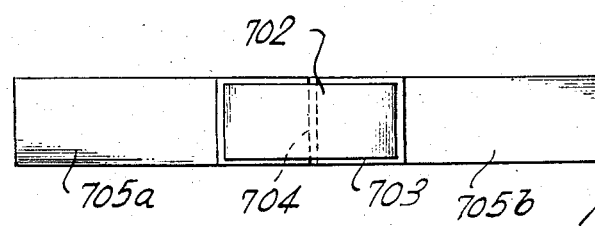

FIGS. 43a and 43b illustrate a further embodiment of a suitable flex sensor, utilizing a piezoelectric transducer 702 supported by an elastomeric pad 703 mounted over a gap 704 between two flat members 705a, 705b of metal or any other suitable structural material which combine to form a relatively elongated strip. The members 705a, 705b may, if desired, be relatively rigid rather than springy, in view of the flexibility introduced by the gap 704 at the center of the strip.

It will be apparent from the foregoing description that those of ordinary skill in the data processing art should be able to use a wide variety of computer implementations in both hardware and software to practice many of the analysis and evaluation techniques embodied within the methods and apparatus of the present invention. By way of example, the invention may be practiced on a Model No. 8085 Microprocessor Unit manufactured by INTEL Corp. 3065 Bowers Avenue, Santa Clara, Calif., supplemented by three EPROM units, Model No. 2716, two input-output ports, Model No. 8255A, and a single RAM unit (1024×8), such as those available from Mostek Corp., 1215 West Crosby Road, Carrollton, Tex.

The new and improved electronic sphygmomanometer system of the present invention is extremely accurate, reliable and easy to use. The system provides enhanced precision in separating true korotkoff sound signals and pressure pulse signals from artifact and noise signals and is quick to inform medical personnel of any conditions which indicate the presence of unreliable data. Hence, the system of the present invention minimizes the time consuming and error-prone aspects of manual techniques for the measurement of human blood pressure and heart rate and obviates the need for a high degree of skill and subjective expertise on the part of medical personnel required to make such measurements.

It will be apparent from the foregoing that, while particular forms of the invention have been illustrated and described, various modifications can be made without departing from the spirit and scope of the invention. Accordingly, it is not intended that the invention be limited, except as by the appended claims.

I claim:

1. In an electronic sphygmomanometer, the combination comprising:
   means for providing, from a first source, detected korotkoff sounds as electrical signals;
   means for providing, from a second source, associated pressure waveform korotkoff sound precursors as electrical signals, each of said korotkoff sound precursors relating solely to the indivdidual korotkoff sound signal with which that precursor is associated; and
   analyzing means for analyzing the waveforms of all of said electrical signals to determine their conformity with predetermined waveform characteristics, whereby those electrical signals having waveforms representative of true korotkoff sounds are separated from those electrical signals which do not represent true korotkoff sounds.

2. Apparatus as set forth in claim 1, wherein said analyzing means includes:
   means for measuring the amplitudes of said precursor waveforms.

3. Apparatus as set forth in claim 2, wherein said analyzing means includes:
   means for rejecting any precursor waveform which exceeds prescribed amplitude thresholds.

4. Apparatus as set forth in claim 1, wherein said analyzing means includes:
   means for measuring the slopes of said precursor waveforms.

5. Apparatus as set forth in claim 4, wherein said analyzing means includes: means for rejecting any precursor waveform which exceeds prescribed slope thresholds.

6. Apparatus as set forth in claim 1, wherein said analyzing means includes:

means for measuring the slopes of said waveforms of said korotkoff sound electrical signals.

7. Apparatus as set forth in claim 6, wherein said analyzing means further includes:
means for rejecting any korotkoff waveform with a slope magnitude below a prescribed noise threshold.

8. Apparatus as set forth in claim 7, wherein said analyzing means further includes:
means for determining said noise threshold only during those time periods between successive precursor waveforms when no korotkoff waveform is likely to occur.

9. Apparatus as set forth in claim 8, and further including:
means for aborting the measurement process if the magnitude of said noise threshold exceeds a prescribed maximum.

10. Apparatus as set forth in claim 1, wherein said analyzing means includes:
means for measuring the phase of each of said waveforms of said korotkoff sound electrical signals relative to said associated precursor waveform.

11. Apparatus as set forth in claim 10, wherein said measuring means includes:
means for measuring both the peak amplitude of said precursor waveform and the amplitude of said precursor waveform at that point in time where the korotkoff waveform occurs.

12. Apparatus as set forth in claim 11, wherein said measuring means further includes:
means for determining the ratio of both of said amplitudes.

13. Apparatus as set forth in claim 10, and further including:
means for rejecting any korotkoff waveform with a measured phase outside of prescribed threshold limits.

14. Apparatus as set forth in claim 10, wherein said measuring means includes:
means for determining the time of occurrence of said korotkoff waveform relative to the time of occurrence of the peak of said precursor waveform.

15. Apparatus as set forth in claim 10, wherein said measuring means includes:
means for determining the time of occurrence of said korotkoff waveform relative to the time of occurrence of the point of steepest slope on the rising portion of said precursor waveform.

16. Apparatus as set forth in claim 1, wherein said analyzing means includes:
means for locating the korotkoff waveform with a maximum slope magnitude during the rising portion of an associated precursor waveform.

17. Apparatus as set forth in claim 16, wherein said analyzing means includes:
means for scanning both said precursor waveforms and said korotkoff waveforms for a predetermined prior time period upon detection of a prescribed location in said precursor waveform.

18. In an electronic sphygmomanometer, the combination comprising:
first means for detecting korotkoff sounds;
second means, independent of said first means, for detecting pressure waveform kortokoff sound precursor waveforms, each of said precursor waveforms relating solely to the individual korokoff sound with which that precursor is associated;
means for providing said detected korotkoff sounds and said associated korotkoff sound precursor waveforms as two separate streams of electrical signals; and
analysis means for separately analyzing the waveforms of all of said korotkoff sound electrical signals and said associated precursor waveform signals, to selectively determine the conformity of all of said signals with predetermined waveform characteristics and to correlate said korotkoff sound signals with said precursor waveforms, whereby those electrical signals having waveforms representative of true korotkoff sounds are not separated from those electrical signals which do not represent true korotkoff sounds and those electrical signals having waveforms representative of true korotkoff sound precursors are separated from those electrical signals which do not represent true korotkoff sound precursors.

19. A combination as set forth in claim 18, wherein said analysis means evaluates the amplitude of each of said precursor waveform signals.

20. A combination as set forth in claim 18, wherein said analysis means evaluates the slope of each of said precursor waveform signals.

21. A combination as set forth in claim 18, wherein said analysis means evaluates the slope amplitude of each of said korotkoff sound signals.

22. A combination as set forth in claim 18, wherein each of said associated precursor waveforms is a blood pressure pulse waveform produced during each cardiac cycle.

23. A combination as set forth in claim 18, wherein said analysis means analyzes the amplitude of a plurality of portions of said precursor waveforms.

24. A combination as set forth in claim 18, wherein said analysis means analyzes the phase of said korotkoff sound signal relative to said associated precursor waveform.

25. A combination as set forth in claim 18, wherein said analysis means analyzes the slope amplitude of said korotkoff sound signal relative to a prescribed amplitude threshold.

26. A combination as set forth in claim 18, wherein said analysis means analyzes the slope amplitude and phase of each of said korotkoff sound signals.

27. A combination as set forth in claim 18, wherein said analysis means analyzes the slope amplitude of said korotkoff sound waveform and the phase of said korotkoff sound waveform relative to said korotkoff sound precursor waveform.

28. A sphygmomanometer as set forth in claim 18, wherein said analysis means measures the conformity of said input electrical signals relating to said korotkoff sounds with predetermined waveform characteristics of a first class of generalized waveforms.

29. An electronic sphygmomanometer as set forth in claim 28, wherein said analysis means also measures the conformity of said input electrical signals relating to said associated korotkoff sound precursors with predetermined characteristics of a second class of specialized waveforms.

30. A combination as set forth in claim 29, wherein said analysis means measures the phase of said korotkoff sound relative to said korotkoff sound precursor.

31. In an electronic sphygmomanometer for analyzing korotkoff sounds produced by an auscultation blood pressure measuring process and associated blood pressure korotkoff sound precursor waveforms, the combination comprising:

first means for providing said korotkoff sounds and said associated korotkoff sound precursor waveforms as separate input electrical signals from separate sources, each of said korotkoff sound precursor waveforms relating solely to and being correlated with the individual korotkoff sound signal with which that precursor is associated;

second means for analyzing the waveforms of all of said input electrical signals representing said korotkoff sounds to selectively determine their conformity with predetermined waveform characteristics;

third means for analyzing the waveforms of all of said input electrical signals relating to said associated korotkoff sound precursor waveforms to determine selectively their conformity with predetermined waveform characteristics;

fourth means for analyzing and correlating the waveforms of all of said input electrical signals relating to said korotkoff sounds and said associated korotkoff sound precursors to selectively determine their conformity with each other; and fifth means responsive to said second means, said third means and said fourth means for selectively producing output electrical signals in correlaton only with those input electrical signals corresponding to true korotkoff sounds and true korotkoff sound precursors, whereby those input electrical signals representing true korotkoff sounds and true korotkoff sound precursors are separated from artifact and noise signals.

32. In an electronic sphygmomanometer, the combination comprising:

means for providing, from a first source, detected korotkoff sounds as electrical signals;

means for providing, from a second source, associated pressure waveform korotkoff sound precursors as electrical signals, each of said korotkoff sound precursors relating solely to the individual korotkoff sound signal with which that precursor is associated; and means for analyzing the waveforms of all of said electrical signals to determine their conformity with predetermined waveform characteristics, so that those electrical signals having waveform representative of true korotkoff sounds and true korotkoff sound precursors are separated from those electrical signals which do not represent true korotkoff sounds and associated korotkoff sound precursors, whereby systolic and diastolic blood pressure may be determined.

33. A combination as set forth in claim 32, and further comprising:

means for determining heart rate from said korotkoff sound precursors.

34. An electronic sphygmomanometer, comprising:

input means for providing korotkoff sounds from a first source and associated pressure waveform korotkoff sound precursors from a second source as separate input electrical signals, each of said korotkoff sound precursors relating solely to the individual korotkoff sound signal with which the precursor is associated;

waveform analysis means for receiving and analyzing the waveforms of all of said of input electrical signals relating to said korotkoff sounds and associated korotkoff sound precursors to determine selectively the conformity of each individual input electrical signal with predetermined waveform characteristics and to produce an electrical output indicative of the presence or absence of such conformity, as well as the presence and correlation of said input electrical signals relating to said korotkoff sounds with said electrical signals relating to said korotkoff sound precursors; and output means responsive to said electrical output from said waveform analysis means for producing output electrical signals indicative of only those input electrical signals which represent the occurrence of true korotkoff sounds.

35. A combination as set forth in claim 34, wherein said korotkoff sound precursors are blood pressure pulse waveforms produced by successive cardiac cycles.

36. A combination as set forth in claim 34, including means for locating the occurrence of each korotkoff sound signal on the rising slope portion of each associated precursor.

37. An electrical sphygmomanometer, comprising:

first means for providing electrical waveforms from a first source representing korotkoff sounds;

second means for providing electrical waveforms from a second source representing associated pressure waveform korotkoff sound precursors, each of said korotkoff sound precursors relating solely to the individual korotkoff sound signal with which that precursor is associated;

third means for analyzing the slope amplitude of portions of said waveforms representing korotkoff sounds and producing an output representative of the slope magnitude and occurrence of those waveforms;

fourth means for determining the slope and amplitude of said waveforms representing associated korotkoff sound precursors;

fifth means for determining the phase of said waveforms representing korotkoff sounds relative to said waveforms representing said associated korotkoff sound precursors;

sixth means for providing an electrical output representative of the occurrence of true korotkoff sounds, in response to the analysis by said third means, said fourth means and said fifth means; and seventh means for anlayzing the electrical output of said sixth means to determine blood pressure.

38. A sphygmomanometer as set forth in claim 37, wherein said fifth means includes:

means for measuring both peak amplitude of said precursor waveform and the amplitude of said precursor waveform at the point in time where said korotkoff waveform occurs.

39. A sphygmomanometer as set forth in claim 37, wherein said fifth means includes:

means for determining time of occurrence of said korotkoff waveform relative to the time of occurrence of the peak of said precursor waveform.

40. A sphygmomanometer as set forth in claim 37, wherein said fifth means includes:

means for determining the time of occurrence of said korotkoff waveform relative to the time of occurrence of the point of steepest slope on the rising portion of said precursor waveform.

41. A sphygmomanometer as set forth in claim 37, wherein said fifth means includes:

means for rejecting any korotkoff waveform with a measured phase outside of prescribed threshold limits.

42. A sphygmomanometer as set forth in claim 37, and further including:
means for scanning both said precursor waveforms and said korotkoff waveforms for a predetermined prior time period upon detection of a prescribed location in said pecursor waveform.

43. A sphygmomanometer as set forth in claim 37, and further including:
means for rejecting any korotkoff waveform with a slope magnitude below a prescribed noise threshold.

44. A sphygmomanometer as set forth in claim 43, and further including:
means for determining said noise threshold only during those periods between successive precursor waveforms when no korotkoff waveform is likely to occur.

45. In an electronic sphygmomanometer for analyzing korotkoff sounds produced by an auscultation blood pressure measuring process and associated korotkoff sound precursors, the combination comprising:
first means for providing korotkoff sounds from a first source and associated pressure waveform korotkoff sound precursors from a second source as separate input electrical signals, each of said korotkoff sound precursors relating solely to the individual korotkoff sound signal with which that precursor is associated;
second means for pre-screening selectively said input electrical signals from said first means relating to said korotkoff sounds for the presence of said input electrical signals relating to associated korotkoff sound precursors, and producing output electrical signals representing those input electrical signals corresponding to the occurrence of true korotkoff events; and
third means for analyzing the output electrical signals from said second means to determine blood pressure.

46. An electronic sphygmomanometer comprising:
first means for providing from a first source electrical waveforms representing korotkoff sounds and from a second source electrical waveforms representing blood pressure signals defining associated pressure waveform korotkoff sound precursors, each of said korotkoff sound precursors relating solely to the individual korotkoff sound signal with which that precursor is associated;
second means for analyzing selectively portions of said waveforms representing said korotkoff sounds;
third means for analyzing selectively portions of said waveforms representing associated korotkoff sound precursors;
fourth means for determining selectively the presence of specified korotkoff sound precursors by the correlation of said electrical waveforms with prescribed waveform characteristics to produce an electrical output representing only true korotkoff events as distinguished from artifacts and noise signals.

47. In an electronic sphygmomanometer, the combination comprising:
means for converting detected korotkoff sounds and associated pressure waveform korotkoff precursors to electrical signals; and
analysis means for analyzing the waveforms of all said electrical signals to determine their conformity with predetermined waveform characteristics and to locate each korotkoff sound on the rising slope portion of the associated korotkoff precursor, whereby those electrical signals having waveforms representative of true korotkoff sounds are separated from those electrical signals which do not represent true korotkoff sounds.

48. A combination as set forth in claim 47, wherein said analysis means produces output electrical signals proportional in amplitude to the slope of those input electrical signals representing true korotkoff sounds.

49. A combination as set forth in claim 47, wherein said analysis means analyzes the amplitude of portions of said precursors.

50. A combination as set forth in claim 47, wherein said analysis means analyzes the slope of portions of said precursors.

51. A combination as set forth in claim 47, wherein said analysis means analyzes the phase of each korotkoff sound relative to its associated precursor.

52. In an electronic sphygmomanometer, the combination comprising:
first signal source means for detecting korotkoff sounds and differentiating said sounds to provide a stream of korotkoff sound signals;
second signal source means, independent of said first means, for detecting cardiac cycle blood pressure pulses as korotkoff sound precursor pressure waveforms, each of said precursor waveforms relating solely to the individual korotkoff sound signal with which that precursor is associated;
means for providing said korotkoff sound signals and said associated korotkoff sound precursors as two separate streams of electrical signals;
analyzer means for separately analyzing the waveforms of all of said korotkoff sound electrical signals and said associated precursor waveforms, to selectively determine the conformity of each individual korotkoff sound signal and each individual precursor waveform with predetermined waveform characteristics and to correlate each genuine korotkoff sound signal with its associated precursor waveform, whereby those electrical signals having waveforms representative of true korotkoff sounds are separated from those electrical signals which do not represent true korotkoff sounds and those electrical signals having waveforms representative of true korotkoff sound precursors are separated from those electrical signals which do not represent true korotkoff sound precursors; and
means for determining blood pressure from said true korotkoff sounds.

53. A combination as set forth in claim 52, wherein said analysis means analyzes the amplitude of portions of each of said precursor waveforms relative to predetermined baseline thresholds.

54. A combination as set forth in claim 52, wherein said analysis means analyzes the slope of the rising portions of each of said precursor waveforms to determine the location of maximum positive slope.

55. A combination as set forth in claim 52, wherein said analysis means analyzes the slope amplitude of portions of each of said precursor waveforms relative to prescribed thresholds.

56. A combination as set forth in claim 52, wherein said analysis means analyzes the slope amplitude of each of said korotkoff sound signals and the phase of each korotkoff sound signal relative to the rising positive slope portion of its associated precursor waveform.

57. In an electronic sphygmomanometer, the combination comprising:
means for inflating a cuff;
means for deflating said cuff;
means for monitoring for the presence of noise signals during deflation of said cuff; and
means for temporarily arresting said deflation in response to detection of excessive noise signals.

58. A combination as set forth in claim 57, and further comprising:
means for terminating said deflation and dumping the pressure in said cuff in response to persistence of excessive noise signals beyond a prescribed time limit.

59. A method of blood pressure measurement, comprising the steps of:
converting detected korotkoff sounds and associated blood pressure pulse precursors from separate sources to separate waveform signals; and
analyzing the individual waveforms of all of said waveform signals to determine their conformity with predetermined waveform characteristics including correlation of said korotkoff waveform signals with said pressure pulse waveform signals, whereby those waveforms representative of true korotkoff sounds are separated from those waveforms which do not represent true korotkoff sounds.

60. A method as set forth in claim 59, wherein said analyzing step includes:
measuring the amplitude of said precursor waveform.

61. A method as set forth in claim 60, wherein said analyzing step includes:
rejecting any precursor waveform which exceeds prescribed amplitude thresholds.

62. A method as set forth in claim 59, wherein said analyzing step includes:
measuring the slope of said precursor waveform.

63. A method as set forth in claim 62, wherein said analyzing step includes:
rejecting any precursor waveform which exceeds prescribed slope thresholds.

64. A method as set forth in claim 59, wherein said analyzing step includes:
measuring the slope of said korotkoff waveform.

65. A method as set forth in claim 64, wherein said analyzing step further includes:
rejecting any korotkoff waveform with a slope magnitude below a prescribed noise level.

66. A method as set forth in claim 65, wherein said analyzing step further includes:
determining said noise threshold only during those time periods between successive precursor waveforms when no korotkoff waveform is likely to occur.

67. A method as set forth in claim 66, and further including:
aborting the measurement process if the magnitude of said noise threshold exceeds a prescribed maximum.

68. A method as set forth in claim 59, wherein said analyzing step includes:
measuring the phase of said korotkoff waveform relative to said precursor waveform.

69. A method as set forth in claim 68, wherein said measuring step includes:
measuring both the peak amplitude of said precursor waveform and the amplitude of said precursor waveform at the point in time where said korotkoff waveform occurs.

70. A method as set forth in claim 69, wherein said measuring step further includes:
determining the ratio of both of said amplitudes.

71. A method as set forth in claim 68, and further including:
rejecting any korotkoff waveform with a measured phase outside of prescribed threshold limits.

72. A method as set forth in claim 71, wherein said measuring step includes:
measuring the time of occurrence of said korotkoff waveform relative to the time of occurrence of the peak of said precursor waveform.

73. A method as set forth in claim 71, wherein said measuring step includes:
measuring the time of occurrence of said korotkoff waveform relative to the time of occurrence of the point of steepest slope on the rising portion of said precursor waveform.

74. A method as set forth in claim 73, wherein said measuring step includes:
storing the data relating to said korotkoff waveform signals and said pressure pulse waveform signals for subsequent analysis;
validating korotkoff sound precursors from the stored data to provide validated data; and
scanning back over said validated data to determine said phase.

75. A method as set forth in claim 69, wherein said analyzing step includes:
locating the korotkoff waveform with a maximum slope magnitude during the rising portion of an associated precursor waveform.

76. A method as set forth in claim 59, wherein said analyzing step includes:
scanning both said precursor waveforms and said korotkoff waveforms for a predetermined prior time period upon detection of a prescribed location in said precursor waveform.

77. In a method of blood pressure measurement, the steps comprising:
inflating a cuff on the arm of a patient;
deflating said cuff;
monitoring for the presence of noise signals during said deflation; and
arresting said deflation temporarily in response to detection of excessive noise signals.

78. A method as set forth in claim 77, and further comprising the step of:
reinstituting deflation of said cuff if said noise signals diminish sufficiently within a prescribed time limit after initial detection.

79. A method as set forth in claim 77, and further comprising the steps of:
terminating said deflation and dumping the pressure in said cuff in response to persistence of said excessive noise signals beyond a prescribed time limit after initial detection.

80. In a method of blood pressure measurement, the combination comprising:
generating a pulse stream representing blood pressure waveforms which are precursors to korotkoff sound signals;

generating a pulse stream representing said korotkoff sound signals;
generating a noise threshold for said korotkoff signals only during selected time periods between successive precursors when said korotkoff signals are not likely to occur.

81. In a method wherein a korotkoff pulse stream is to be analyzed in the determination of blood pressure, the steps comprising:
generating a pulse stream representing korokoff sound signals;
generating a corresponding pulse stream representing associated pressure waveform korotkoff sound precursors;
locating the first pair of adjacent korotkoff signals above a maximum amplitude threshold adjacent either extreme end of the blood pressure spectrum; and
establishing as a blood pressure limit the first korotkoff sound signal below said threshold encountered in proceeding away from said pair of korotkoff signals in the direction of the selected extreme end of said pressure spectrum.

82. In a method wherein a korotkoff pulse stream is to be analyzed in the determination of blood pressure, the steps comprising:
generating a pulse stream representing korotkoff sound signals in the blood pressure domain;
generating a corresponding pulse stream representing associated blood pressure waveform korotkoff sound precursors in the blood pressure domain;
locating the first pair of adjacent korotkoff signals above a minimum amplitude threshold adjacent either extreme end of the blood pressure spectrum;
extrapolating the amplitudes of said pair of korotkoff signals to determine an extreme value of blood pressure in the direction of the selected extreme end of said pressure spectrum; and
establishing said extreme value as a blood pressure limit if said value is spaced from said pair of korotkoff signals by no more than the average pressure change per pulse period between successive precursors.

83. In a method wherein a korotkoff pulse stream is to analyzed in the determination of blood pressure, the steps comprising:
generating a pulse stream representing korotkoff sound signals in the blood pressure domain;
generating a corresponding pulse stream representing associated blood pressure waveform korotkoff sound precursors in the blood pressure domain;
locating the first pair of adjacent korotkoff signals above a minimum amplitude threshold adjacent either extreme end of the blood pressure spectrum;
extrapolating the amplitudes of said pair of korotkoff signals to determine an extreme value of blood pressure in the direction of the selected extreme end of said pressure spectrum; and
establishing as a blood pressure limit beyond said pair of korotkoff signals toward said selected extreme end of said pressure spectrum an additional pressure equal to the average pressure change per pulse period between successive precursors, if said extreme value yields a pressure value spaced from said pair of korotkoff signals by more than said average pressure change.

84. In a method of blood pressure measurement, the steps comprising:
providing as electrical input, from a first source, signals representing korotoff sound waveforms;
providing as electrical input, from a second source, separate from said first source, signals representing associated korotkoff sound precursor pressure waveforms, each of said korotkoff sound precursor waveforms relating solely to the individual korotkoff sound signal waveform with which that precursor is associated;
analyzing the waveforms of said signals representing korotkoff sounds;
analyzing the waveforms of said signals relating to associated korotkoff sound precursors;
analyzing the waveforms of all of said signals to determine selectively the presence of specified korotkoff sound precursors and the conformity of such precursors with said korotkoff sounds, whereby those waveforms representative of true korotkoff sounds are separated from those waveforms which do not represent true korotkoff sounds.

85. A method as set forth in claim 84, wherein said analyzing steps include:
measuring the amplitude of said precursor waveform.

86. A method as set forth in claim 85, wherein said analyzing steps further include:
rejecting any precursor waveform which exceeds prescribed amplitude thresholds.

87. A method as forth in claim 84, wherein said analyzing steps include:
measuring the slope of said precursor waveform.

88. A method as set forth in claim 87, wherein said analyzing steps further include:
rejecting any precursor waveform which exceeds prescribed slope thresholds.

89. A method as set forth in claim 84, wherein said analyzing steps include:
measuring the slope of said korotkoff waveform.

90. A method as set forth in claim 89, wherein said analyzing steps further include:
rejecting any korotkoff waveform with a slope magnitude below a prescribed noise threshold.

91. A method as set forth in claim 90, wherein said analyzing steps further include:
determining said noise threshold only during those time periods between successive precursor waveforms when no korotkoff waveform is likely to occur.

92. A method as set forth in claim 91, and further including:
aborting the measurement process if the magnitude of said noise threshold exceeds a prescribed maximum.

93. A method as set forth in claim 84, wherein said analyzing steps include:
measuring the phase of said korotkoff waveform relative to said precursor waveform.

94. A method as set forth in claim 93, wherein said measuring step includes:
measuring both the peak amplitude of said precursor waveform and the amplitude of said precursor waveform at that point in time where said korotkoff waveform occurs.

95. A method as set forth in claim 94, wherein said measuring step further includes:
determining the ratio of both of said amplitudes.

96. A method as set forth in claim 94, and further including:

rejecting any korotkoff waveform with a measured phase outside of prescribed threshold limits.

97. A method as set forth in claim 96, wherein said measuring step includes:

measuring the time of occurrence of said korotkoff waveform relative to the time of occurrence of the peak of said precursor waveform.

98. A method as set forth in claim 96, wherein said measuring step includes:

measuring the time of occurrence of said korotkoff waveform relative to the time of occurence of steepest slope on the rising portion of said precursor waveform.

99. A method as set forth in claim 84, wherein said analyzing steps include:

locating the korotkoff waveform with a maximum slope magnitude during the rising portion of an associated precursor waveform.

100. A method as set forth in claim 84, wherein said analyzing steps include:

scanning both said precursor waveforms and said korotkoff waveforms for a predetermined prior time period upon detection of a prescribed location in said precursor waveform.

* * * * *